US007981654B2

(12) United States Patent
Vehmaanperä et al.

(10) Patent No.: US 7,981,654 B2
(45) Date of Patent: Jul. 19, 2011

(54) CELLULASES AND THEIR USES

(75) Inventors: Jari Vehmaanperä, Klaukkala (FI);
Terhi Puranen, Nurmijärvi (FI); Leena Valtakari, Rajamäki (FI); Jarno Kallio, Järvenpää (FI); Marika Alapuranen, Tuusula (FI); Marja Paloheimo, Vantaa (FI); Pentti Ojapalo, Tuusula (FI)

(73) Assignee: AB Enzymes Oy, Rajamäki (FI)

( * ) Notice: Subject to any disclaimer, the term of this patent is extended or adjusted under 35 U.S.C. 154(b) by 0 days.

(21) Appl. No.: 12/760,744

(22) Filed: Apr. 15, 2010

(65) Prior Publication Data
US 2010/0204080 A1    Aug. 12, 2010

Related U.S. Application Data

(62) Division of application No. 11/119,526, filed on Apr. 29, 2005, now Pat. No. 7,741,093.

(51) Int. Cl.
*C12N 9/42* (2006.01)
*C12N 9/00* (2006.01)
*C02F 3/34* (2006.01)
*D06M 16/00* (2006.01)
*C11D 3/384* (2006.01)
*C11D 3/00* (2006.01)
*C11D 1/00* (2006.01)
*C07H 21/04* (2006.01)
*D06M 11/00* (2006.01)

(52) U.S. Cl. ........ 435/209; 435/183; 435/262; 435/263; 510/114; 510/300; 510/374; 510/392; 510/531; 510/535; 536/23.4; 536/23.7; 8/115.51; 8/116.1

(58) Field of Classification Search .................. 435/209, 435/183, 262, 263; 510/114, 300, 374, 392, 510/531, 535; 536/23.4, 23.7; 8/115.51, 8/116.1
See application file for complete search history.

(56) References Cited

U.S. PATENT DOCUMENTS

| 3,664,961 A | 5/1972 | Norris |
| 5,433,750 A | 7/1995 | Gradinger et al. |
| 5,443,750 A | 8/1995 | Convents et al. |
| 5,770,418 A | 6/1998 | Yaver et al. |
| 5,792,641 A | 8/1998 | Schuelein et al. |
| 5,837,515 A | 11/1998 | Suominen et al. |
| 5,843,745 A | 12/1998 | Berka et al. |
| 5,989,899 A | 11/1999 | Bower et al. |
| 6,015,783 A * | 1/2000 | von der Osten et al. ...... 510/392 |
| 6,184,019 B1 | 2/2001 | Miettinen-Oinonen et al. |

FOREIGN PATENT DOCUMENTS

| EP | 0 238 216 | 9/1987 |
| EP | 0 244 234 | 11/1987 |
| EP | 0 663 950 | 7/1995 |
| WO | 91/17244 | 11/1991 |
| WO | 94/07998 | 4/1994 |
| WO | 95/33386 | 12/1995 |
| WO | 96/29397 | 9/1996 |
| WO | 97/14804 | 4/1997 |
| WO | 97/43409 | 11/1997 |
| WO | 98/08940 | 3/1998 |
| WO | 98/12307 | 3/1998 |
| WO | 2004/016760 | 2/2004 |

OTHER PUBLICATIONS

Supplementary European Search Report for corresponding EP 06 72 5936, Jun. 19, 2009.
Lowry et al., "Protein measurement with the Folin phenol reagent," J. Biol. Chem., 193:265-275 (1951).
Laemmli, "Cleavage of structural proteins during the assembly of the head of bacteriophage T4," Nature, 227:680-685 (1970).
Bailey and Nevalainen, "Induction, isolation and testing of stable *Trichoderma reesei* mutants with improved production of solubilizing cellulose," Enz. Microbiol. Technol., 3: 153-157 (1981).
Penttilä et al., "A versatile transformation system for the cellulolytic filamentous fungus *Trichoderma reesei*," Gene, 61:155-164 (1987).
Malardier et al., "Cloning of the nitrate reductase gene (niaD) of *Aspergillus nidulans* and its use for transformation of *Fusarium oxysporum*," Gene, 15:147-156 (1989).
Azevedo et al., "Cloning, sequencing and homologies of the cbh-1 (exoglucanase) gene of *Humicola grisea* var. *Thermoidea*," J. Gen. Microbiol., 136: 2569-2576, (1990).
Aho et al., "Monoclonal antibodies against core and cellulose-binding domains of *Trichoderma reesei* cellobiohydrolases I and II and endoglucanase I," Eur. J. Biochem., 200:643-649 (1991).
Henrissat, "A classification of glycosyl hydrolases based on amino acid sequence similarities," Biochem. J., 280: 309-316 (1991).
Henrissat and Bairoch, "New families in the classification of glycosyl hydrolases based on amino acid sequence similarities," Biochem. J., 293:781-788 (1993).
Joutsjoki et al., "Transformation of *Trichoderma reesei* with the *Hormoconis resinae* glucoamylase P (gamP) gene: production of a heterologous glucoamylase by *Trichoderma reesei*," Curr. Genet., 24:223-228 (1993).
Karhunen et al., "High frequency one-step gene replacement in *Trichoderma reesei*. I. Endoglucanase I overproduction," Mol. Gen. Genet., 241:515-522 (1993).
Srisodsuk et al., "Role of the interdomain linker peptide of *Trichoderma reesei* cellobiohydrolase I in its interaction with crystalline cellulose," J. Biol. Chem., 268:20756-20761 (1993).
Saloheimo et al., "A novel, small endoglucanase gene, egl5, from *Trichoderma reesei* isolated by expression in yeast," Mol. Microbiol., 13:219-228 (1994).
Linder et al., "Identification of functionally important amino acids in the cellulose-binding domain of *Trichoderma reesei* cellobiohydrolase I," Protein Science, 4:1056-1064 (1995).

(Continued)

*Primary Examiner* — Ganapathirama Raghu
(74) *Attorney, Agent, or Firm* — Banner & Witcoff, Ltd.

(57) ABSTRACT

The present invention provides novel cellulase fusion proteins, preparations of cellulase fusion proteins and compositions of cellulase fusion proteins. The present invention further provides cellulase expression vectors, host cells expressing cellulase and methods for preparing such vectors and cells. Uses of cellulases, cellulase preparations and cellulase compositions in the textile, detergent, pulp and paper industries are also provided.

24 Claims, 17 Drawing Sheets

OTHER PUBLICATIONS

Srisodsuk et al., "*Trichoderma reesei* cellobiohydrolase I with an endoglucanase cellulose-binding domain: action on bacterial microcrystalline cellulose," J. Biotech.,57:49-57 (1997).

Kim et al., "Functional Analysis of a Hybrid Endoglucanase of Bacterial Origin Having a Cellulose Binding Domain from a Fungal Exoglucanase," Applied Biochem. Biotech., 75:193-204 (1998).

Gustavsson, Malin, et al., "Stable linker peptides for a cellulose-binding domain-lipase fusion protein expressed in *Pichia pastoris*," Protein Engineering, May 31, 2001 (revised), pp. 711-715, vol. 14 No. 9, Oxford University Press. (XP009118009).

Hong et al., "Cloning of a gene encoding thermostable cellobiohydrolase from *Thermoascus aurantiacus* and its expression in yeast," Appl. Microbiol. Biotechnol., 63:42-50 (2003).

Miettinen-Oinonen et al., "Three cellulases from *Melanoarpus albomyces* with applications in the textile industry," Enz. Microbiol. Technol. 34:332-341 (2004).

Haakana et al., "Cloning of cellulase genes from *Melanocarpus albomyces* and their efficient expression in *Trichoderma reesei*," Enz. Microbiol. Technol., 34: 159-167 (2004).

Witkowski et al., Conversion of b-ketoacyl synthase to a malonyl decarboxylase by replacement of the active-site cysteine with glutamine. Biochemistry, 1999, vol. 38: 11643-11650.

Seffernick et al., Melamine deaminase and Atrazine chlorohydrolase: 98 percent identical but functionally different. J. Bacteriol., 2001, vol. 183 (8): 2405-2410.

Guo et al., Protein tolerance to random amino acid change. PNAS., 2004, vol. 101 (25): 9205-9210.

Broun et al., Catalytic plasticity of fatty acid modification enzymes underlying chemical diversity of plant lipids. Science, 1998, vol. 282: 1315-1317.

\* cited by examiner

A)

cbh1 prom    cbh1 term    cbh1 3´ flanking

20K+CBD gene    amdS gene

B)

20K+CBD fusion protein:

M. albomyces        T. reesei CBHI
        20K                           Linker    CBD pALK1434: D G G F A V F K A P S G S T G <u>N P S</u>...$T^1$ Q ... Y Y S Q C L pALK1435: D G G F A V F K A P S <u>G G N</u>...$T^1$ Q ... Y Y S Q C L

A)

B)

20K+CBD fusion protein:

```
            M. albomyces           T. reesei CBHI
            20K              Junction      Linker    CBD
pALK1768:   D G G F A F G P I G S T G N P S...T¹ Q ... Y Y S Q C L pALK1769:   D G G F W G E I G S T G N P S...T¹ Q ... Y Y S Q C L pALK1770:   D G G F P A V Q I P S S T G N P S...T¹ Q ... Y Y S Q C L pALK1775:   D G G F A W G E I G S T G N P S...T¹ Q ... Y Y S Q C L
```

A)

B)

20K+CBD$_{mut}$ fusion protein:

| M. albomyces | | *T. reesei* CBHI | |
| 20K | Junction | Linker | CBD |

D G G F  P A V Q I P S S T G  <u>N P S</u>...T$^1$ Q S H Y...N P Y$^{31}$ Y$^{32}$ S Q C L pALK1877:  N P A$^{31}$ Y$^{32}$ S Q C L
pALK1878:  N P Y$^{31}$ A$^{32}$ S Q C L
pALK1879:  N P W$^{31}$ Y$^{32}$ S Q C L
pALK1880:  N P A$^{31}$ A$^{32}$ S Q C L

Catalytic        Linker                                    CBD
Domain
                 434         444              460
..FGPIGSTG NPSGGNPPGGNPPGTTTTRRPATTTGSSPGP *TQSHYGQ*..
          |         |               |
          |  ΔG-444 |               |
          |                         |
          |  ΔG-460                 |

B)

20K+CBD linker deletions:

*M. albomyces*                 *T. reesei* CBHI
        20K     Junction    Linker              CBD pALK1893:DGGF PAVQIPSS TGNPSTTTTRRPATTTGSSPGP$T^1$Q...P $Y^{31}$ $Y^{32}$ S Q C L pALK1896:DGGF PAVQIPSS TGNPSP $T^1$Q...P $Y^{31}$ $Y^{32}$ S Q C L pALK1899:DGGF PAVQIPSS TGNPSTTTTRRPATTTGSSPGP$T^1$Q...P $A^{31}$ $A^{32}$ S Q C L pALK1952:DGGF PAVQIPSS TGNPSP $T^1$Q...P $A^{31}$ $A^{32}$ S Q C L

A)

B)

Melanocarpus albomyces 50K fusion protein:

| *M. albomyces* | *T. reesei* CBHI |
|---|---|
| 50K | Linker   CBD |

N L R W G E I G S T G <u>N P S</u> ...T¹ Q S H Y...N P Y Y S Q C L

A)

B)

*Melanocarpus albomyces* 50KB fusion protein:

*M. albomyces*　　　　T. reesei CBHI
50KB　　　　　　　　Linker　CBD

N I R F G P I G S T G <u>N P S</u> ...T$^1$ Q S H Y...N P Y Y S Q C L

A)

B)

*Thermoascus aurantiacus* CBHI+CBD fusion protein:

```
T. aurantiacus        T. reesei CBHI
CBHI          Junction  Linker   CBD

N I K V G P I G S T G  N P S...T¹ Q S H Y...N P Y Y S Q C L
```

Fig 17
A
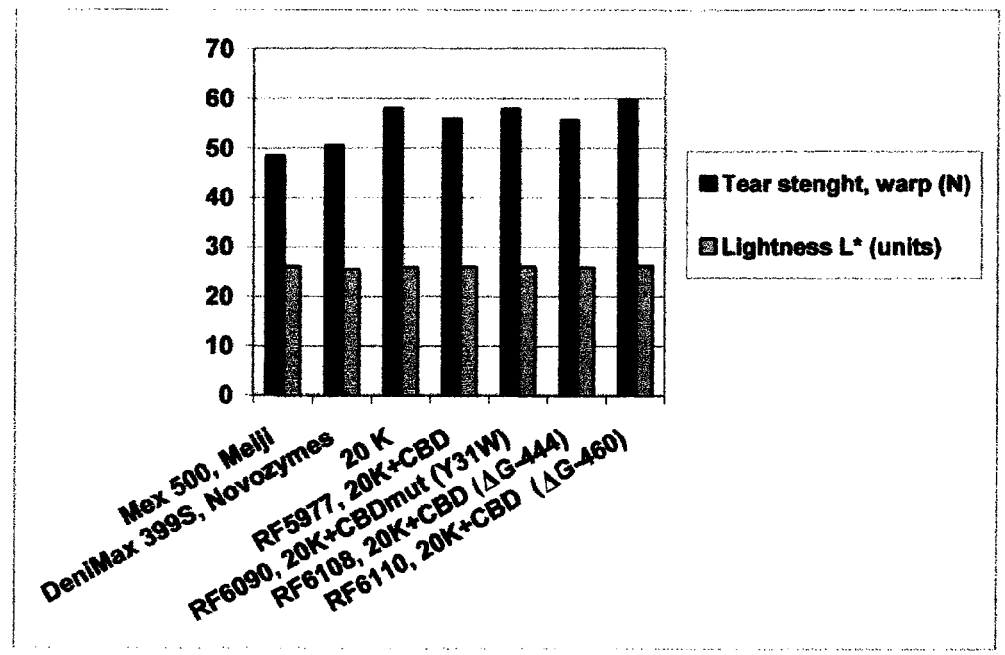
B
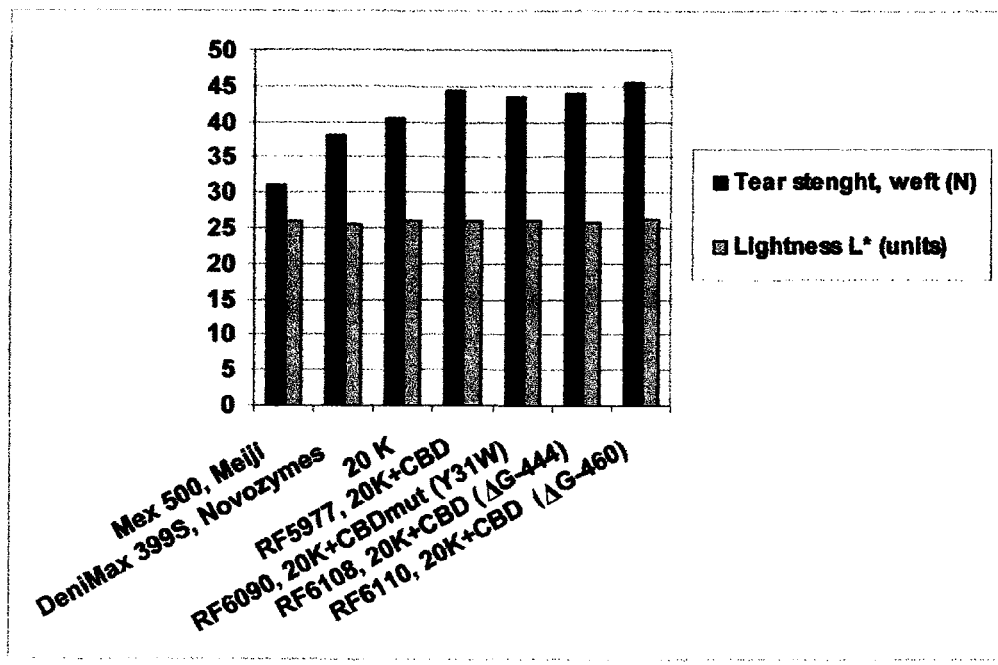

CELLULASES AND THEIR USES

RELATED APPLICATIONS

This application is a divisional of U.S. patent application Ser. No. 11/119,526 filed on Apr. 29, 2005, now U.S. Pat. No. 7,741,093, and is hereby incorporated herein by reference in its entirety for all purposes.

FIELD

The present invention relates to novel cellulase fusion proteins, preparations and compositions containing these cellulase fusion proteins, expression vectors, host cells and methods for their preparation and uses of the cellulases, preparations and compositions in the textile, detergent and pulp and paper industries.

BACKGROUND

Cellulose is a linear polysaccharide of glucose residues connected by β-1,4 linkages. In nature, cellulose is usually associated with lignin together with hemicelluloses, such as xylans and glucomannans. Cellulolytic enzymes hydrolyze cellulose and are produced by a wide variety of bacteria and fungi. Cellulases are industrially important enzymes with a current annual market value of about 190 million US $. In the textile industry, cellulases are used in denim finishing to create a fashionable stone washed appearance in denim cloths in a biostoning process, and they are also used, for instance, to clean fuzz and prevent formation of pills on the surface of cotton garments. In detergent industry cellulases are used to brighten colors and to prevent graying and pilling of garments. Cellulases are further used in food industry and animal feed manufacturing, and they have a great potential in the pulp and paper industry, for instance, in deinking to release ink from fiber surfaces and in improving pulp drainage. The wide spectrum of industrial uses for cellulases has established a need for commercial cellulase products containing different cellulase components and functioning optimally in different pH and temperature ranges.

The practical use of cellulases is hampered by the nature of the known cellulases, which are often mixtures of cellulases having a variety of activities and substrate specificities. For this reason, efforts have been made to obtain cellulases having only the desired activities. The unique properties of each cellulase make some more suitable for certain purposes than others. While the enzymes differ in a number of ways, one of the most important differences is the pH optimum. Neutral cellulases are most active in the pH range 6-8 and alkaline cellulases in the pH range 7.5-10, whereas acid cellulases, having the pH optimum at pH 4.5-5.5, show very low activity levels at higher pH values. Neutral and acid cellulases are especially useful in the textile industry. In fabric treatment cellulases attack the chains of cellulose molecules that form the cotton fibers, thereby affecting the characteristics of the fabric.

In textile industry "stone washed" look or an abraded look has been denim producers' interest in recent years. Traditional stone washing with pumice stones reduces the strength of fabric and burdens the laundering apparatuses. The trend has been towards enzymatic denim finishing processes and cellulases have replaced or are being used together with pumice stones to give the fabric its desired "worn" look. Controlled enzyme treatment results in less damage to the garments and machines and eliminates the need for disposal of stones.

Cellulases applied in denim treatment are usually divided into two main groups: acid and neutral cellulases. Acid cellulases typically operate at pH 4.5-5.5 and the neutral cellulases in the range of pH 6-8. Acid cellulases used in biostoning mainly originate from *Trichoderma reesei* (sexual form *Hypocrea jecorina*) and the neutral cellulases come from a variety of fungi, including genera of *Melanocarpus, Humicola, Thielavia, Myceliophthora, Fusarium, Acremonium,* and *Chrysosporium* (Haakana et al. 2004). *T. reesei* enzymes include, e.g., cellulases from the glycoside family 5 (endoglucanase II, EGII), family 7 (cellobiohydrolase I, CBHI) and family 12 (endoglucanase III, EGIII; Ward et al. 1993), and the neutral cellulases, most often endoglucanases, from family 45 and family 7 (Henrissat, 1991; Henrissat and Bairoch, 1993).

Cellulases comprise a catalytic domain/core (CD) expressing cellulase activity. In addition to the catalytic domain the cellulase molecule may comprise one or more cellulose binding domains (CBDs), also named as carbohydrate binding domains/modules (CBD/CBM), which can be located either at the N- or C-terminus of the catalytic domain. CBDs have carbohydrate-binding activity and they mediate the binding of the cellulase to crystalline cellulose but have little or no effect on cellulase hydrolytic activity of the enzyme on soluble substrates. These two domains are typically connected via a flexible and highly glycosylated linker region.

Cellulases that attack primarily on the surface of the fiber are especially useful in stone washing of denim dyed with Indigo dye, as the dye is located on the surface of the fiber. When used to treat cotton fabric, neutral cellulases generally require a longer washing time than the acid cellulases. However, neutral cellulases have less aggressive action on cotton than acid cellulases, and do not affect on the strength of the fabric as much as acid cellulases. Neutral cellulases have a broader pH profile and thus the pH increase that occurs during biostoning has little effect on the activity of neutral cellulase enzymes. However, since cellulase treatments also have undesirable effects, such as fiber damage and strength loss, a suitable balance between the desired and unwanted effects has to be sought.

WO97/14804, which is incorporated herein by reference, discloses three novel neutral cellulases of *Melanocarpus* origin, which are especially useful in the textile and detergent industry. Specifically a 20 kDa endoglucanase (Cel45A), a 50 kDa endoglucanase (Cel7A), and a 50 kDa cellobiohydrolase (Cel7B) are described. These cellulases designated herein as "20K-cellulase", "50K-cellulase", and "50K cellulase B", respectively, are derived from *Melanocarpus albomyces* and show good stone washing effects.

Since there is an existing demand, especially in the textile and detergent industry, for further improved cellulases, it has been suggested that improvements in cellulases could be obtained by forming fusion proteins. Also in WO97/14804 fusion protein constructs of 20K-cellulase, 50K-cellulase, and 50K cellulase B with, for instance, *Trichoderma reesei* cellulase, hemicellulase or mannase or functional domains thereof, are generally suggested. Further, in order to create new properties for the disclosed cellulases, fusions of the disclosed cellulases with domains, such as cellulose binding domain (CBD), preferably with its linker, are suggested. However, no specific examples are given, nor are described the new properties aimed to.

Cellulase fusion proteins are additionally known, for instance, from WO96/29397, which discloses endoglucanases formed by a fusion between endoglucanases from *Myceliophthora thermophila*, from *Macrophomina phaseo-* lina and from *Crinipellis scabella* and the CBD/linker from *Humicola insolens*. Said endoglucanases in their natural form do not have a CBD/linker.

EP 663 950 discloses cellulase variants, especially *Humicola insolens* 43 kDa cellulase variants, wherein the cellulase may include a linking region from another microorganism species, for instance for providing improved properties, such as improved resistance to anionic surfactants, to oxidation or to bleaching agents.

However, there is a continuous need for improved cellulases that also are less harmful to the fiber in textile industry and in other fields, where cellulases traditionally are used. In particular, there is a continuous need for more efficient cellulases to improve the process economics.

The present invention aims to meet this need.

BRIEF DESCRIPTION

An object of the present invention is to provide novel cellulase fusion proteins having improved hydrolytic properties for use in textile industry, especially in stone washing denim, and for use in detergent compositions as well as in other fields. The novel cellulase fusion proteins of the invention are active at neutral and alkaline pH values, they have highly improved washing performance in textile biofinishing and biostoning applications and in detergent applications, and yet they do not compromise the strength of fabrics. With the improved efficiency of the cellulase fusion proteins of the invention, the manufacturing process of the enzymes is significantly more economical. Additional advantages are achieved also in terms of logistics and the storage of the enzyme products, when smaller amounts of the enzyme product are needed.

A further object of the present invention is to provide polynucleotides encoding the novel cellulase fusion proteins of the present inventions.

A further object of the present invention is to provide novel expression plasmids or vectors containing such polynucleotides, useful for the production of the novel cellulase fusion proteins of the present invention, and novel hosts transformed with said expression plasmids.

A further object of the present invention is to provide enzyme preparations, which contain one or more novel cellulase fusion proteins having improved hydrolytic properties.

A still further object of the present invention is to provide methods of using the enzyme preparations and the cellulase fusion proteins for finishing of textiles, especially for biostoning of denim.

A still further object of the present invention is to provide means for the use of the enzyme preparations of the invention in detergent compositions.

The present invention relates to a novel cellulase fusion protein comprising

A. an optionally modified first amino acid sequence of a cellulase core derived from one species, and B. an optionally modified second amino acid sequence of a linker and/or cellulose binding domain (CBD) derived from another species, wherein a junction region has been introduced between said first amino acid sequence and said second amino acid sequence, whereby a stable fusion protein is obtained.

Preferably, the junction region has the following general formula:

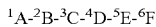

wherein
$^1$A is selected from a group consisting of Gly, Ala, Leu, Pro, Ile, and Val; preferably $^1$A is Gly or Val, most preferably Gly;
$^2$B is selected from a group consisting of Gly, Ala, Leu, Pro, Ile, Phe, Val, Glu, Asp, Gln, and Asn; preferably $^2$B is Pro, Gln, or Glu;
$^3$C is selected from a group consisting of Gly, Ala, Lys, Leu, Pro, Ile, Val, Ser, and Thr; preferably $^3$C is Ile;
$^4$D is selected from a group consisting of Gly, Ala, Leu, Pro, Ile, and Val; preferably $^4$D is Gly or Pro;
$^5$E is selected from a group consisting of Ser, Pro and Thr; preferably $^5$E is Ser; and
$^6$F is selected from a group consisting of Ser, Thr or is absent, preferably $^6$F is Ser or is absent; wherein $^1$A is attached at the C-terminal amino acid sequence of the cellulase core and $^6$F is attached at the N-terminal amino acid sequence of the linker and/or domain (CBD).

The present invention further relates to an expression vector comprising a first polynucleotide sequence encoding an optionally modified first amino acid sequence of a cellulase core derived from one species, and a second polynucleotide sequence encoding an optionally modified second amino acid sequence of a linker and/or cellulose binding domain (CBD) derived from another species, and a polynucleotide encoding a junction region connecting said first and second polynucleotide sequences, said polynucleotide sequences encoding the respective amino acid sequences of the cellulase fusion proteins of the invention.

The present invention further relates to novel hosts transformed with the vectors of the invention, especially hosts that are capable of high level expression of the cellulase fusion protein of the invention.

The present invention further relates to an enzyme preparation, which contains one or more cellulase fusion proteins of the invention.

The present invention further relates to a method for using the enzyme preparations of the invention for the finishing of textiles, especially for biostoning of denim.

The present invention further relates to the use of the enzyme preparations of the invention in detergent compositions.

BRIEF DESCRIPTION OF THE DRAWINGS

FIG. 12A Amino acid sequence of the interdomain linker peptide of *T. reesei* CBHI (Cel7A) (SEQ ID NO:79). The amino acids contained in the linker region are underlined. ΔG-444 and ΔG-460 represent the linker deletion of residues 434-444 and 434-460, respectively. FIG. 12B. Amino acid sequence of a junction point at which *Melanocarpus albomyces* 20K (Cel45A) protein is fused to truncated linker peptide of *Trichoderma reesei* CBHI (Cel7A) followed by the intact or mutated cellulose-binding domain (CBD) in the pALK1893, pALK1896, pALK1899 and pALK1952 expression cassettes (See SEQ ID NOs: 75, 76, 77, 78). The amino acids contained in the linker region are underlined, and the amino acid sequence of the CBD region is marked by italics. The first amino acid and the tyrosine residues or their substitutions in the CBD region are indicated by superscript numbers.

FIG. 17. Effect of the 20K+CBD fusion proteins and corresponding commercial enzyme preparations on the strength of the denim fabric. FIG. 17A. Tear strength (N), warp. FIG. 17B. Tear strength (N), weft.

DETAILED DESCRIPTION

Figure 1:
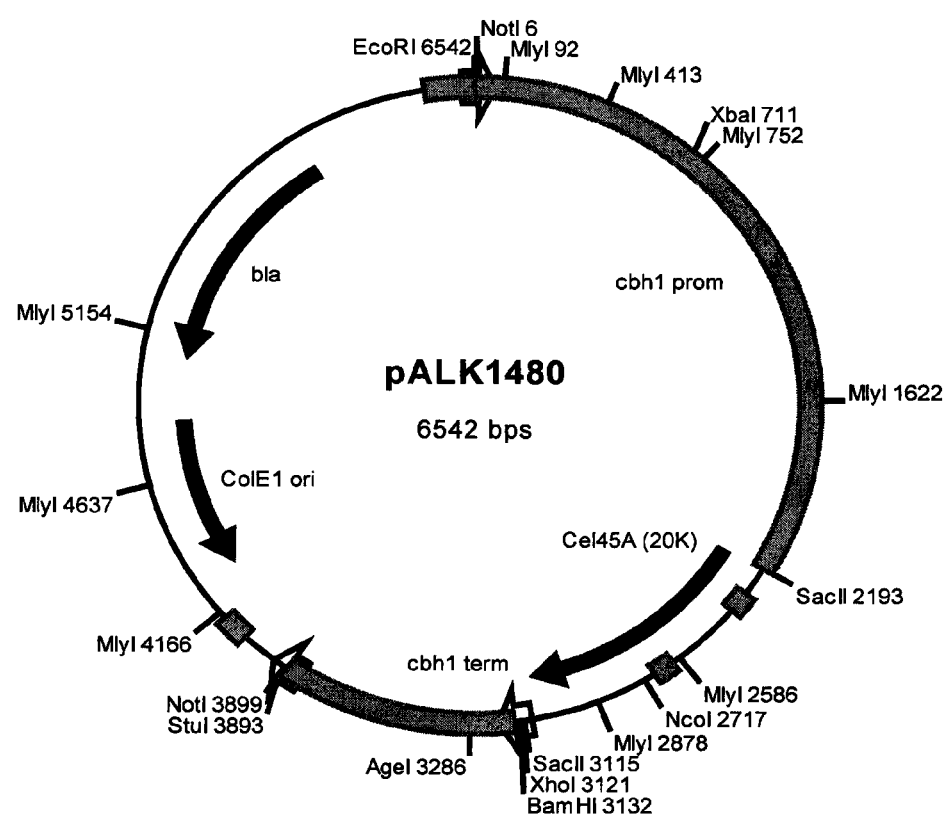
FIG. 1 is the schematic map of the plasmid pALK1480.

The present invention is based on efforts to further improve neutral cellulases, in particular those described in WO97/14804, aiming at reducing the loss of the strength of the fabric in the enzyme treatment. In some applications the 20K cellulase has shown undesirable properties in relation to fiber strength, possibly due to the small size. The simple hypothesis was that an increase in the size of the enzyme would decrease the ability of the enzyme to penetrate into the fibers, thereby weakening the fibers to a smaller extent, i.e., the enzyme would be less aggressive. To do this the fusion protein approach suggested in WO97/14804 was used, and fusions constructs containing a neutral cellulase core of a *Melanocarpus* species and a tail consisting of a linker/CBD of an acid cellobiohydrolase I of *T. reesei* were designed. Surprisingly, however, contrary to the suggestions of the prior art, fully stable fusion protein constructs could not be obtained, but the fusion partners separated from each other in the culture conditions. This was presumably due to the presence of protease(s).

To produce stable fusion proteins, one approach was to design novel junction constructs having no adjacent hydrophobic amino acids (e.g., V, I, L, F, and W) in order to prevent cleavage by aspartylproteases. However, although the constructs produced fusion proteins, some degradation was occasionally observed.

Based on the alignment of neutral cellulases naturally containing a linker/CBD tail, further constructs were produced and finally these constructs proved to be most stable and most useful for further testing. In addition, fusion constructs were designed which carried mutations in the CBD resulting in reduced or minimal affinity or adsorption to cellulose (Linder et al. 1995).

The novel constructs produced improved strength properties, as was the aim. Surprisingly, the stable cellulase fusion proteins additionally showed unexpected improvement in washing performance, and were as high as even six times as efficient as their "parent" cellulases. However, the production yields maintained at about the same level. This means that only one sixth of the amount of the cellulase activity presently needed is enough for achieving the same washing performance of the prior art cellulase. This produces considerable savings in the production step, and also in the logistics and storage, thereby decreasing the environmental burden. Also the undesired effects of the cellulase preparations are reduced, thereby bringing further savings for the final users of the enzyme product. Considering that about 2 billion pairs of denim jeans are produced annually, and most of them are finished with cellulase, the advantage is highly significant.

Accordingly, the present invention provides a novel cellulase fusion protein comprising A. an optionally modified first amino acid sequence of a cellulase core derived from one species, and B. an optionally modified second amino acid sequence of a linker and/or cellulose binding domain (CBD) derived from another species, wherein a junction region has been introduced between said first amino acid sequence and said second amino acid sequence, whereby a stable fusion protein is obtained.

In a preferred embodiment of the invention the junction region has the following general formula:

$^1$A-$^2$B-$^3$C-$^4$D-$^5$E-$^6$F wherein $^1$A is selected from a group consisting of Gly, Ala, Leu, Pro, Ile, and Val; preferably $^1$A is Gly or Val, most preferably Gly;

$^2$B is selected from a group consisting of Gly, Ala, Leu, Pro, Ile, Phe, Val, Glu, Asp, Gln, and Asn; preferably $^2$B is Pro, Gln, or Glu;

$^3$C is selected from a group consisting of Gly, Ala, Lys, Leu, Pro, Ile, Val, Ser, and Thr; preferably $^3$C is Ile;

$^4$D is selected from a group consisting of Gly, Ala, Leu, Pro, Ile, and Val; preferably $^4$D is Gly or Pro;

$^5$E is selected from a group consisting of Ser, Pro and Thr; preferably $^5$E is Ser; and $^6$F is selected from a group consisting of Ser, Thr or is absent, preferably $^6$F is Ser or is absent; wherein $^1$A is attached at the C-terminal amino acid sequence of the cellulase core and $^6$F is attached at the N-terminal amino acid sequence of the linker and/or domain (CBD).

In a specially preferred embodiment of the invention the junction region has the following general formula:

$^1$Gly-$^2$B-$^3$Ile-$^4$D-$^5$Ser-$^6$F   (SEQ ID NO: 51)

wherein
$^2$B is Pro, Gln, or Glu;
$^4$D is Gly or Pro;

$^5$E is Ser; and
$^6$F is Ser or is absent.

In another specially preferred embodiment of the invention the junction region has the following general formula:

$^1$Val-$^2$Gln-$^3$Ile-$^4$Pro-$^5$Ser-$^6$Ser.   (SEQ ID NO: 52)

In another specially preferred embodiment of the invention the junction region has the following general formula:

$^1$Gly-$^2$Glu-$^3$Ile-$^4$Gly-$^5$Ser.   (SEQ ID NO: 53)

In another specially preferred embodiment of the invention the junction region has the following general formula:

$^1$Gly-$^2$Pro-$^3$Ile-$^4$Gly-$^5$Ser.   (SEQ ID NO: 54)

In a preferred embodiment of the invention the first amino acid sequence is from a neutral cellulase and the second amino acid sequence is from an acid cellulase.

In another preferred embodiment of the invention the first amino acid sequence is from a cellulase of family 45 (Cel 45) and the second amino acid sequence is from cellulase of family 7 (Cel 7).

As used in the present context the expression "cellulase core" or "core" means the catalytic domain/core (CD) of an enzyme expressing cellulase activity. Such a catalytic domain may be in its naturally occurring form (i.e., intact) or, preferably, is modified as defined below. The expressions "derivative" and functional variant denote polypeptides expressing the same cellulase activity but including modifications as defined below.

In the present context conventional one-letter amino acid codes and three-letter amino acid codes are used. Thus, A and Ala denote alanine, R and Arg denote arginine, N and Asn denote asparagine, D and Asp denote aspartic acid, Cys and C denote cysteine, E and Glu denote glutamic acid, Q and Gln denote glutamine, G and Gly denote glycine, H and His denote histidine, I and Ile denote isoleucine, L and Leu denote leucine, K and Lys denote lysine, M and Met denote methionine, F and Phe denote phenylalanine, P and Pro denote proline, S and Ser denote serine, T and Thr denote threonine, W and Trp denote tryptophan, Y and Tyr denote tyrosine, and V and Val denote valine. In addition to naturally occurring L-amino acids, D-amino acids could be used.

In the cellulase fusion proteins of the invention, the neutral cellulase is preferably of fungal origin. The neutral cellulase can be derived from genera of *Melanocarpus, Humicola, Thielavia, Myceliophthora, Fusarium, Acremonium, Chrysosporium, Thermoascus, Scopulariopsis, Myriococcum, Talaromyces,* or *Chaetomium*. Specifically preferred are *Melanocarpus* sp, with *Melanocarpus albomyces* being especially preferred. The acid cellulase used in the cellulase fusion proteins of the invention originate from *Trichoderma* sp. or *Hypocrea*, especially from *Trichoderma reesei*.

In a specifically preferred embodiment of the invention the first amino acid sequence is 20 K cellulase of *Melanocarpus albomyces* of SEQ ID. NO: 2 or a derivative thereof, and the second amino acid sequence is the linker and/or CBD of *Trichoderma reesei* cellobiohydrolase I of SEQ ID. NO: 4 or a derivative thereof.

In one preferred embodiment of the invention the cellulase fusion proteins contain modifications in cellulase core and/or in the linker and/or CBD. As used in the present context the expression "modified" refers to mutations, such as a deletion, insertion, or substitution of one or more amino acids, or other modifications, such as glycosylations. Examples of such mutations include the substitution of conserved tyrosine residues at positions 31 (corresponding tyrosine Y492 of the mature polypeptide) and/or 32 (corresponding tyrosine Y493 of the mature polypeptide) with an aliphatic amino acid, preferably with alanine, and/or with an aromatic amino acid, such as tryptophan, of CBD of *Trichoderma reesei* CBHI as described by Linder et al., 1995. Further examples of such mutations include interlinker mutations of *Trichoderma reesei* CBHI as described by Srisodsuk et al., 1993, such as deletions of amino acids from position 434 to 444 and from position 434 to 460 of the mature *Trichoderma* CBHI sequence. Further examples of such mutations include the deletion of Ala at position 207, the deletion of Val at position 208, the substitution of Phe209Trp, and insertion of Pro after position 206 in 20 K cellulase sequence of *Melanocarpus albomyces* of SEQ ID. NO: 2.

The cellulase fusion proteins of the invention are stable. In the context of the present invention the expression "stable cellulase fusion protein" means that at least 20%, preferably at least 40%, more preferably at least 70%, most preferably 90%-100%, of the produced cellulase fusion protein contains uncleaved junction region between the amino acid sequences during the fermentation. This means that 20%-100%, preferably 40%-100%, more preferably 70%-100% of the produced cellulase have the first and the second amino acid sequence fused together. The expression "stable cellulase fusion protein" additionally means that the cellulase fusion protein preparation may be stable as such or has been stabilized by, e.g., heat treatment or adjusting pH or by adding stabilizers or agents reducing protease activity or by separating the fusion protein from the culture. The heat treatment in the present context means a treatment at temperature, which allows the fusion protein in the preparation to be maintained adequately stable. The heat treatment can be, e.g., a treatment at pH 6.0 at 65° C. for 60 to 70 minutes.

In the present context the expression "intact fusion protein" means that the junction between the first and the second amino acid sequence in the fusion protein of the invention remains unbroken, although there may or may not appear terminal degradation in said sequences.

In one preferred embodiment of the cellulase fusion protein of the invention, the first amino acid sequence is a *Melanocarpus albomyces* 20K sequence having SEQ ID NO: 2 or a functional variant thereof. In another preferred embodiment of the first amino acid sequence is *Melanocarpus albomyces* 50K sequence having SEQ ID NO: 6 or a functional variant thereof. In another preferred embodiment of the first amino acid sequence is *Melanocarpus albomyces* 50KB sequence having SEQ ID NO: 8 or a functional variant thereof. In another preferred embodiment of the first amino acid sequence is *Thermoascus aurantiacus* CBHI sequence having SEQ ID NO: 10 or a functional variant thereof. In yet one preferred embodiment of the cellulase fusion protein of the invention the second amino acid sequence is the linker and cellulase binding domain sequence having SEQ ID NO: 4 of *Trichoderma reesei* cellobiohydrolase I or a functional variant thereof.

Thus in a highly preferred embodiment of the cellulase fusion protein of the invention, the first amino acid sequence of cellulase core is selected from SEQ ID. NO: 37, 38, 39, 40, 41, 42, and 43, especially SEQ ID. NO: 39, and the second amino acid sequence of a linker and/or CBD sequence is selected from SEQ ID. NO: 44, 45, 46, 47, 48, 49, and 50. In a special embodiment of the invention, the first amino acid sequence of cellulase core is SEQ ID. NO: 39 and the second amino acid sequence of a linker and/or CBD sequence is SEQ ID. NO: 47, 49, or 50.

The present invention further relates to an expression vector comprising a first polynucleotide sequence encoding an optionally modified first amino acid sequence of a cellulase core derived from one species, and a second polynucleotide sequence encoding an optionally modified second amino acid sequence of a linker and/or cellulose binding domain (CBD) derived from another species, and a polynucleotide encoding a specific junction region connecting said first and second polynucleotide sequences, said polynucleotide sequences encoding the respective amino acid sequences as specifically defined above.

The present invention further relates to cellulase preparations containing one or more cellulase fusion proteins of the invention alone or together with additional enzymes and additives according to the special application in question.

The present invention further relates to the uses of and methods for using the cellulase fusion protein preparations of the invention for purposes specifically disclosed below.

The cellulase fusion protein preparations of the invention are especially useful in the textile and detergent industry. These cellulases show highly improved abrasion effect and visible and measurable increase of lightness. They show acceptable backstaining and good as well as focused contrast in biostoning. They are useful in the textile industry for biofinishing of fabrics or garments, e.g., depilling, defuzzing, color clarification, harshness reduction, creation of different finishes (for example, a 'peach skin,' 'worn out,' 'sand washed,' or 'antique look' effect) and for biofinishing of yarn, for example, reduction of hairiness and improvement of smoothness. Additional uses include the use in detergent compositions to improve fabric care properties by antipilling, antigraying, color clarification and softening, and to improve textile cleaning effect, for instance soil removal.

As used in the present context the expression "biostoning" of fabric or garment means the use of enzymes in place of, or in addition to, pumice stones for the treatment of fabric or garment, especially denim.

As used in the present context the expression "biofinishing" refers to the use of enzymes in a controlled hydrolysis of cellulosic fibers in order to modify the fabric or yarn surface in a manner that prevents permanently pilling, improves fabric handle like softness and smoothness, clears the surface structure by reducing fuzzing, which results in clarification of colors, improves the drapability of the fabric, improves moisture absorbability, which may improve also the dyeability.

As used in the present context the expression "backstaining" refers to the tendency of released dye to redeposit on the surface of the fabric fibers.

As used in the present context the expression "detergent" refers to a cleansing agent that can contain surface active agents (anionic, non-ionic, cationic and ampholytic surfactants), builders and other optional ingredients such as anti-redeposition and soil suspension agents, optical brighteners, bleaching agents, dyes and pigments and hydrolases. Suitable listing of the contents of detergents is given in U.S. Pat. No. 5,433,750, a suitable list of surfactants is given in U.S. Pat. No. 3,664,961.

By an amino acid sequence that is an "equivalent" or a "derivative" of a specific amino acid sequence is meant an amino acid sequence that is not identical to the specific amino acid sequence, but rather contains at least some amino acid changes (deletions, substitutions, inversions, insertions, etc) that do not essentially affect the biological activity of the protein as compared to a similar activity of the specific amino acid sequence, when used for a given application.

The biological activity of a cellulase is its catalytic activity, and/or its ability to bind to cellulosic material.

An expression vector is a cloning plasmid or vector capable of expressing DNA encoding the cellulase fusion proteins of the invention after transformation into a desired host. When a fungal host is used, the gene of interest is preferably provided to a fungal host as part of a cloning or expression vehicle that integrates into the fungal chromosome, or allows the gene of interest to integrate into the host chromosome, or as an autonomously replicating plasmid. Sequences that are part of the cloning vehicle or expression vehicle may also be integrated with said DNA during the integration process. In addition, in fungi the expression vector or parts thereof can be targeted into predetermined loci.

The DNA encoding the fusion proteins of the invention is also preferably placed under the control of (i.e., operably linked to) certain control sequences such as promoter sequences provided by the vector (which integrate with the gene of interest). Alternatively, the control sequences can be those at the insertion site.

The expression control sequences of an expression vector will vary depending on whether the vector is designed to express a certain gene in a prokaryotic or in a eukaryotic host (for example, a shuttle vector may provide a gene for selection in bacterial hosts). Expression control sequences can contain transcriptional regulatory elements such as promoters, enhancer elements, and transcriptional termination sequences, and/or translational regulatory elements, such as translational initiation and termination sites.

A polynucleotide molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. Two DNA sequences (such as a promoter region sequence linked to the 5' end of the protein encoding sequence) are said to be operably linked if function of promoter results in the transcription.

The vectors of the invention may further comprise other operably linked regulatory elements such as enhancer sequences.

In a preferred embodiment, genetically stable transformants are constructed whereby the DNA encoding the cellulase fusion proteins of the invention is integrated into the host chromosome by transformation with a vector, which harbors sequences promoting integration of said vector into the chromosome.

Cells that have stably integrated DNA encoding the cellulase fusion proteins of the invention into their chromosomes are selected by also introducing one or more markers, homologous or heterologous, which allow for selection of host cells which contain the expression vector in the chromosome, for example the marker may provide biocide resistance, e.g., resistance to antibiotics, or heavy metals, such as copper, or markers complementing an auxotrophic mutation in the host chromosome, and the like. The selectable marker gene can either be directly linked to the DNA gene sequences to be expressed, or introduced into the same cell by co-transformation.

Once the vector or DNA sequence of the invention containing the construct(s) is prepared for expression, the DNA construct(s) is introduced into an appropriate host cell by any of a variety of suitable means, including transformation as known in the art. After the introduction of the vector, recipient cells are grown in a selective medium, which selects for the growth of transformed cells.

Suitable expression and production host systems are for example the production system developed for the fungus host *Trichoderma* (EP 244 234), or *Aspergillus* production system, such as *A. oryzae* or *A. niger* (WO 9708325 and WO 9533386, U.S. Pat. Nos. 5,843,745, 5,770,418), or the production system developed for *Fusarium*, such as *F. oxysporum* (Malardier et al., 1989). Suitable production systems developed for bacteria are a production system developed for *Bacillus*, for example *B. subtilis* or for *E. coli*, or for actinomycete *Streptomyces*. Suitable production systems developed for yeasts are systems developed for *Saccharomyces, Shizosaccharomyces* or *Pichia pastoris*. Production systems in some other microbes or in mammalian cells or in plants are also possible.

Expression of the cloned gene sequence(s) results in the production of the desired protein, or in the production of a fragment of this protein. This expression can take place in a continuous manner in the transformed cells, or in a controlled manner.

Fragments are understood to be parts of nucleic acid molecules long enough to code for the described protein or a biologically active fragment thereof. The term "derivative" means in this context that the nucleotide sequences of these molecules differ from the sequences of the above-described nucleic acid molecules in one or more positions and are highly homologous to said sequence. Homology is understood to refer to a sequence identity of at least 40%, particularly an identity of at least 60%, preferably more than 80% and still more preferably more than 90%. The deviations from the nucleic acid molecules described above can be the result of deletion, substitution, insertion, addition or combination. Homology furthermore means that the respective nucleotide sequences or encoded proteins are functionally and/or structurally equivalent.

As used in the present context the expressions "enzyme preparation" and "cellulase preparation" refers to any enzyme product, which contains at least one cellulase fusion protein. Thus, such an enzyme preparation may be a spent culture medium or filtrate containing one or more cellulase fusion proteins or one or more cellulase fusion proteins and other enzymes, an isolated cellulase fusion protein or a mixture of one or more cellulase fusion proteins or a mixture of one or more cellulase fusion proteins and one or more other enzymes. In addition to the cellulase fusion protein activity, such a preparation may contain additives, such as stabilizers, buffers, preservatives, surfactants and/or culture medium components. Preferred additives are such, which are commonly used in enzyme preparations intended for the application, where the enzyme preparation is used. The enzyme preparation may be in the form of liquid, powder or granulate.

By "spent culture medium" is here meant the culture medium of the host comprising the produced enzymes. Preferably the host cells are separated from the said medium after the production.

The enzyme preparation may comprise one or more cellulase fusion proteins of the present invention or other cellulase enzymes together with one or more cellulase fusion proteins of the present invention. For example, cellulase fusion proteins having different properties may be combined to make the enzyme preparation more useful for different conditions.

To obtain the enzyme preparations of the invention, the hosts having the desired properties (that is, hosts capable of expressing economically feasible quantities of the cellulase fusion proteins of the invention) are cultivated under suitable conditions, the desired enzymes are secreted from the hosts into the culture medium, and the enzyme preparation is recovered from said culture medium by methods known in the art.

The enzyme preparation may comprise in addition to cellulase fusion protein, one or more other enzymes, which may be for example amylases, laccases and/or peroxidases. Alternatively, before, during or after the treatment with the cellulase fusion protein of the present invention, another enzyme treatment may be carried out. The enzyme treatment may comprise, for example, one or more amylase treatments, one or more cellulase treatments and/or one or more peroxidase and/or laccase treatments. Which other enzymes are included to the enzyme preparation or are used in the enzyme treatment, depends on the application.

The enzyme preparation can be the culture medium with or without the native or transformed host cells, or is recovered from the same by the application of methods well known in the art. However, because the cellulase fusion proteins of the invention are secreted into the culture media and display activity in the ambient conditions of the cellulolytic liquor, it is an advantage of the invention that the enzyme preparations of the invention may be utilized directly from the culture medium with no further purification. If desired, such preparations may be lyophilized or the enzymatic activity otherwise concentrated and/or stabilized for storage. The enzyme preparations of the invention are very economical to provide and use because (1) the enzymes may be used in a crude form; isolation of a specific enzyme from the culture medium is unnecessary and (2) because the enzymes are secreted into the culture medium, only the culture medium need be recovered to obtain the desired enzyme preparation; there is no need to extract an enzyme from the hosts. Preferably the host for such production is *Trichoderma*, and especially *T. reesei*.

The enzyme preparations of the invention may be provided as a liquid or as a solid, for example, in a dried powder or granular or liquid form, especially non-dusting granules, or a stabilized liquid, or the enzyme preparation may be otherwise concentrated or stabilized for storage or use. It is envisioned that enzyme preparations containing one or more of the neutral cellulases of the invention can be further enriched or made partially or completely deficient in specific enzymatic activities, so as to satisfy the requirements of a specific utility in various applications e.g., in the textile industry. A mixture of enzyme activities secreted by a host and especially a fungus, can be chosen to be advantageous in a particular industrial application, for example biostoning.

The enzyme preparations of the invention can be adjusted to satisfy the requirements of specific needs in various applications in the textile, detergent or the pulp and paper industry.

Blends may be prepared with other macromolecules that are not necessarily all produced from the same host (for example, other enzymes such as endoglucanases, proteases, lipases, peroxidases, oxidases or amylases) or chemicals that may enhance the performance, stability, or buffering of the desired enzyme preparation. Non-dusting granules may be coated. Liquid enzyme preparations can be stabilized by adding a polyol such as propylene glycol, a sugar or sugar alcohol, lactic acid or boric acid, or sodium chloride, according to established methods.

Protected forms of the enzymes of the invention may be prepared as described in EP 238,216.

The enzyme preparations of the invention can contain a surfactant which can be anionic, non-ionic, cationic, amphoteric or a mixture of these types, especially when used as a detergent composition, Useful detergent compositions are described e.g., in WO 94/07998, U.S. Pat. Nos. 5,443,750 and 3,664,961.

If required, a desired enzyme may be further purified in accordance with conventional conditions, such as extraction, precipitation, chromatography, affinity chromatography, electrophoresis, or the like.

The enzyme preparations of this invention are especially useful in textile industry preferably in biostoning and in biofinishing or in detergent industry. Other useful areas are in pulp and paper industry.

Stone washing has three steps: desizing, abrasion and aftertreatment. The first step, desizing process is normally the first wet treatment of jeans and means the removal of starch or other sizing agents applied usually to the warp yarns to prevent damage during the weaving process. Alpha-amylases are used to remove starch-based size for improved and uniform wet processing. After desizing the jeans are normally rinsed with water or continued directly with the abrasion step.

The second step, abrasion, can be performed with enzymes or pumice stones or both. In all cases mechanical action is needed to remove the dye, and the treatment is usually carried out in washing machines, like drum washers. The term "abraded" means herein the appearance of denim fabric when it has been treated by cellulase enzymes or stones, or both. As a result of uneven dye removal there are contrasts between dyed areas and areas from which dye has been removed. Synonymous expressions are "stone washed look" or "worn look". In enzymatic stone washing, or biostoning, abrasion with pumice stones is completely or partially eliminated and cellulase is added to facilitate the abrasion of Indigo dye from the fiber surface. The cellulase treatment may be done using neutral or acid cellulases or both. If a fabric is not cellulase treated or stone washed, the appearance of the fabric is said to be "dull", since the fashionable contrasts would be missing. When more faded effect is desired, bleaching using chemical agents and/or enzymatic methods such as laccase treatment can be carried out.

Abrasion is generally followed by the third step, aftertreatment, that includes washing and rinsing steps during which detergents, optical brighteners or softeners may be used. After the enzymatic treatment the reaction must be stopped in order to prevent damage of the treated materials, for example by temperature and/or pH inactivation, the latter comprising a thorough rinsing and/or detergent wash-off. This ensures that the mechanical strength of the fiber is not further compromised by the continued presence of the enzyme.

By "denim" is meant, in connection of this invention, denim fabric, usually denim garments, particularly jeans. Advantageously the denim is Indigo dyed denim. Denim can also be treated with Indigo, with derivatives of Indigo or denim dyed with Indigo together with some other dye, for example Indigo-dyed denim with sulphur bottom.

Treatment with a cellulase(s) can completely replace treatment with pumice stones (for example, 1 kg commercial enzyme vs. 100 kg stones). However, cellulase treatment can be combined with pumice stone treatment when it is desired to produce a heavily abraded finish. A peach skin effect in which a fine protruding hair-like covering is created is also achieved by a wash combining a neutral cellulase with pumice stones. The cellulases of this invention are especially useful to provide abraded look and to minimize backstaining in biostoning.

Biostoning is preferably performed from about pH 4.5-9.5, and most preferably between pH 6.0-8.0. The temperature of the reaction can range from about 40-80° C., preferably between 50-70° C., and more preferably between 55-65° C., and most preferably at 60° C. The liquor ratio (the ratio of the volume of liquid per weight of fabric) may range from about 2:1-30:1 preferably 4:1-15:1, and most preferably 5:1-10:1. The enzyme dosage can range from about 5-8000 NCU/g fabric, preferably 20-3000 NCU/g fabric and most preferably 30-1500 NCU/g fabric. The treatment time can range between 15 min-4 h, more preferably 20 min-90 min and most preferably 30 min-60 min. It should be emphasized that the enzyme dosage depends greatly on the type of the fabrics, machinery, process conditions (pH, temperature, liquor ratio, treatment time, denim load, process scale) and type of enzyme preparation and like. If desired, pumice stones can be used in combination with the fusion cellulase proteins. The enzyme dosage required will then be significantly lower. A person skilled in art is capable in defining suitable dosages and conditions.

The cellulase fusion proteins of the invention are useful in the textile industry for biofinishing of fabrics or garments e.g., depilling, defuzzing, color clarification, harshness reduction, the creation of different finishes (for example, a 'peach skin,' 'wornout,' 'sand washed,' or 'antique look' effect) and biofinishing of yarn (for example reduction of hairiness, improvement of smoothness). The cellulase fusion proteins of this invention can be used in biofinishing in acid and in neutral conditions.

The cellulase fusion proteins of this invention are useful in detergent compositions to improve fabric care properties by antipilling, antigraying, color clarification and softening, and to improve textile cleaning effect, for instance soil removal.

The textile material that is treated with the enzyme preparations of the invention may be manufactured of natural cellulose containing fibers or manmade cellulose containing fibers or mixtures thereof. Examples of natural cellulosics are cotton, linen, hemp, jute and ramie. Examples of manmade cellulosics are viscose, cellulose acetate, cellulose triacetate, rayon, cupro and lyocell. The above-mentioned cellulosics can also be employed as blends of synthetic fibers such as polyester, polyamide or acrylic fibers. The textile material may be yarn or knitted or woven or formed by any other means.

The cellulases of the invention, besides being especially useful for the treatment of fabric, are useful in general in any area requiring cellulase activity.

In the pulp and paper industry, neutral cellulases can be used, for example, in deinking of different recycled papers and paperboards having neutral or alkaline pH, in improving the fiber quality, or increasing the drainage in paper manufacture. Other examples include the removal of printing paste thickener and excess dye after textile printing, and as a treatment for animal feed. For example, if the intended application is improvement of the strength of the mechanical pulp, then the enzyme preparations of the invention may provide one or more of these proteins so as to enhance or facilitate the ability of cellulose fibers to bind together. In a similar manner, in the application of pulp refining, the cellulase fusion protein preparations of the invention may provide one or more of these proteins at a level that enhance or facilitate such swelling. Of the fusion proteins of the invention especially suitable for pulp applications are those with a *Melanocarpus albomyces* 50KB or *Thermoascus aurantiacus* CBHI core.

The cellulase fusion proteins of the present invention provide unexpected advantages when used in textile industry and especially in biostoning. The cellulase fusion proteins of the invention are considerably more efficient than the cellulases of prior art. In biostoning at least two-fold, usually at least three-fold and even six-fold lower dosages in terms of neutral cellulase activity units dosed on the weight of the fabric could be used, without impairing the strength of the fabric. In other words, up to six times higher performance is achieved by using the cellulase fusion proteins of the present invention. Since the production-yield of the cellulase fusion proteins of the invention corresponds to that of the known 20K cellulase, the overall production efficiency is significantly improved. This can be directly proportioned to great savings in the amounts of the enzyme needed: the possibility to use reduced amounts of the enzyme offers a considerable economical value in terms of both the manufacture and use, including the logistics.

The invention is described in more detail in the following examples, which are not be interpreted to narrow the scope of the invention but only to clarify the use of the invention.

Example 1

Construction of the Expression Vectors for 20K+CBD Fusion Proteins

Standard molecular biology methods were used in the isolation, purification and enzyme treatments of DNA (plasmids, DNA fragments), in polymerase chain reactions (PCR), in *E. coli* transformations, etc. The basic methods used are described in the standard molecular biology handbooks, e.g., Sambrook et al. (1989) and Sambrook and Russell (2001).

Plasmids constructs were designed to join the *Melanocarpus albomyces* 20K (Cel45A, AC#AJ515703; SEQ ID. NO: 1) coding sequence with the coding sequence of the linker and CBD of the *Trichoderma reesei* CBHI (AC#AR088330; Srisodsuk et al. 1993; SEQ ID. NO: 3). Altogether six different junctions were designed as described in Table 1.

For constructs #1 and #2 set forth in Table 1, a unique NruI site was introduced at the end of the 20K coding sequence. This site enables direct fusion after the codon for the serine #213 of the mature 20K with any DNA fragment with a blunt end. A PCR reaction was run with the primers 20K_Nco (SEQ ID NO: 11) and 20K_NruXho (SEQ ID NO: 14) with the plasmid pALK1480 (FIG. 1) as the template using the program A (Table 3). pALK1480 has the genomic copy of the *M. albomyces* cel45A (encoding the Cel45A or 20K) inserted under the *T. reesei* cbh1 promoter as an exact fusion and having the cbh1 terminator downstream the gene in the pUC19 vector (New England Biolabs, Inc., USA). The PCR reaction mixture contained 1× DyNAzyme™ EXT reaction buffer (Finnzymes, Finland), 8 mM $Mg^{2+}$ (the final concentration adjusted with added $MgCl_2$), 0.2 mM dNTPs, 0.5 µM of each primer, 1.0 units of DyNAzyme™ EXT DNA polymerase (Finnzymes, Finland), and approximately 50 ng/100 µl of the template. The PCR product was digested with NcoI and XhoI restriction enzymes and the fragment was isolated from the agarose gel after electrophoresis. The similarly cut and isolated 6.1 kb fragment of pALK1480 was ligated with the PCR fragment, and transformed into *E. coli* XL1-Blue (Stratagene, USA). The plasmid DNA was isolated from the transformants, and one suitable candidate was verified by sequencing. The resulting plasmid was designated as pALK1429.

Figure 2:
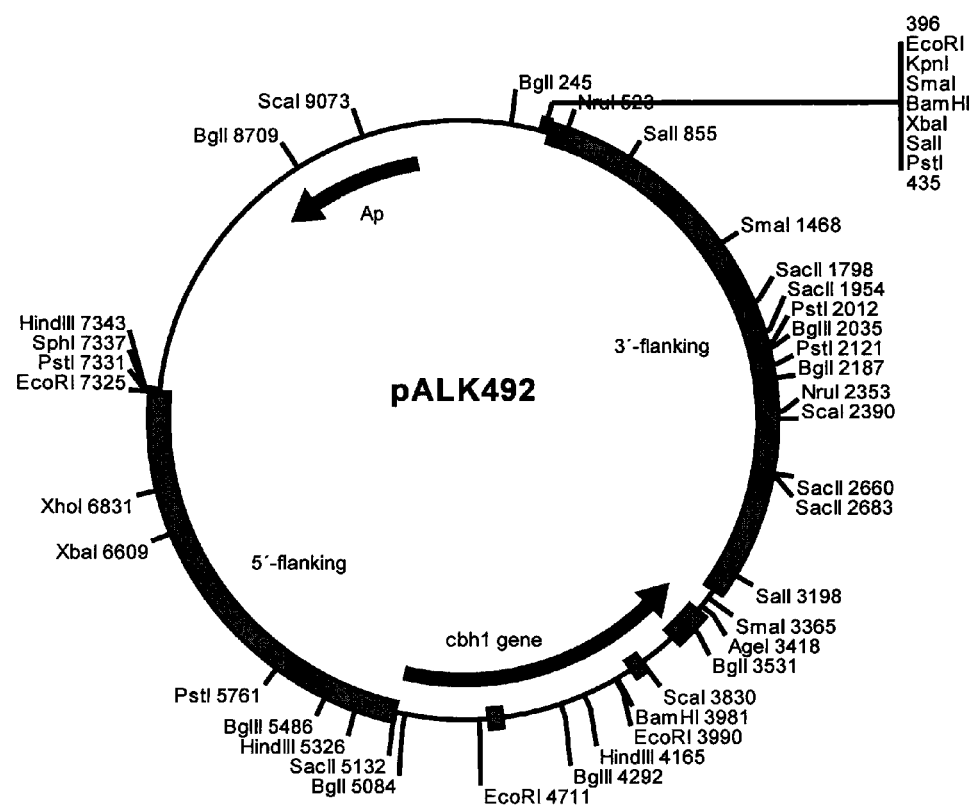
FIG. 2 is the schematic map of the plasmid pALK492.

PCR reactions were performed separately as above with primer pairs 1_BamMly (SEQ ID NO: 16)+XhoAge (SEQ ID NO: 15) and 2_BamMly (SEQ ID NO: 17)+XhoAge (SEQ ID NO: 15) with pALK492 as the template (FIG. 2), and the resulting PCR products, containing the linker and CBD, were digested with MlyI (producing a blunt end just before the desired first codon of the coding sequence of the linker and CBD) and AgeI. pALK492 carries about 6.9 kb PstI fragment of *T. reesei* QM6a chromosomal DNA harboring the cbh1/cel7A gene subcloned into the PstI site of pUC19. pALK1429 obtained above was digested with NruI and AgeI, and the vector part was isolated and ligated separately with the two digested PCR products obtained above, and transformed into *E. coli* XL1-Blue. Plasmid DNAs were isolated, verified by sequencing and the resulting plasmids were designated as pALK1430 (carrying the 1_BamMly+XhoAge PCR product as an insert) and as pALK1431 (carrying the 2_BamMly+XhoAge PCR product as an insert).

TABLE 1

Different junctions constructed between the *Melanocarpus albomyces* 20K and the *Trichoderma reesei* CBHI linker + CBD.

| Construct # | Core-linker junctions | 20K-core template pALK1480 5' primer | 20K-core template pALK1480 3' primer | linker + CBD template pALK492 5' primer | linker + CBD template pALK492 3' primer | Plasmid constructions |
|---|---|---|---|---|---|---|
| 1 | ...hddggfavfkaps.-gstgn... (SEQ ID NO: 55) | 20K_NcoI | 20K-NruXho_GPI | 1_BamMly_oligo | XhoAge_oligo | pALK1434 <- pALK1430 <- pALK1429 |
| 2 | ...hddggfavfkaps.-ggnppg... (SEQ ID NO: 56) | 20K_NcoI | 20K-NruXho_GPI | 2_BamMly_oligo | XhoAge_oligo | pALK1435 <- pALK1431 <- pALK1429 |
| 3 | ...hddggfa.fGPIgs-tgn... (SEQ ID NO: 57) | 20K_NcoI_2 | 20K-NruXho_GPI | 3_BamMly_oligo | XhoAge_oligo | pALK1768 <- pALK1764 <- pALK1758 |
| 4 | ...hddggfWGEIgs-tgn... (SEQ ID NO: 58) | 20K_NcoI_3 | 20K-NruXho_WGEI | 3_BamMly_oligo | XhoAge_oligo | pALK1769 <- pALK1765 <- pALK1759 |
| 5 G | ...hddggfPavQIPSs-tgn... (SEQ ID NO: 59) | 20K_NcoI_2 | 20K-NruXho_PavQIPS | 3_BamMly_oligo | XhoAge_oligo | pALK1770 <- pALK1766 <- pALK1760 |
| 6 | ...hddggfaWGEIgs-tgn... (SEQ ID NO: 60) | 20K_NcoI_3 | 20K-NruXho_WGEI-2 | 3_BamMly_oligo | XhoAge_oligo | pALK1775 <- pALK1774 <- pALK1773 |

In second column, the leftmost part is the *Melanocarpus* derived sequence and the rightmost is the *Trichoderma* derived sequence. Lower cases indicate original sequences, upper cases indicate the modified sequence, period (.) indicate a deleted amino acid and a hyphen indicates the junction point joined by ligating the relevant plasmids. First amino acid of the *Melanocarpus* sequence is histidine #201 of the mature sequence and in constructs #1, #3, #4 and #6 the first amino acid of the *Trichoderma* sequence is glycine #427, in construct #2 glycine #434 and in construct #5 serine #428 of the mature sequence.

TABLE 2

Primers used

| Primer | Length nts | Sequence | Sequence ID NO: |
|---|---|---|---|
| 20K_Nco | 27 | 5'-TACGCCATGGTCGTCCAGTCGACCAGC | 11 |
| 20K_Nco_2 | 35 | 5'-TACGCCATGGTCGTCCAGTCGACCAGCACGGGCGG | 12 |
| 20K_Nco_3 | 46 | 5'-TACGCCATGGTCGTCCAGTCGACCAGCACGGGCGGCGACCTCGGCA | 13 |
| 20K_NruXho | 40 | 5'-CGTACTCGAGTCATCGCGAGGGGGCCTTGAAGACGGCGAA | 14 |
| XhoAge | 30 | 5'-TGACTCGAGACCGGTGCGTCAGGCTTTCGC | 15 |
| 1_BamMly | 34 | 5'-TAGGATCCGAGTCCCATTGGCAGCACCGGCAACC | 16 |
| 2_BamMly | 36 | 5'-TAGGATCCGAGTCCTAGCGGCGGCAACCCTCCCGGC | 17 |
| 3_BamMly | 34 | 5'-TAGGATCCGAGTCCCATTACCGGCAACCCTAGCG | 18 |
| 20K-NruXho_GPI | 55 | 5'-CGTACTCGAGTCATCGCGAGCCGATGGGGCCGAAGGCGAAGCCGCCGTCGTCGTG | 19 |
| 20K-NruXho_WGEI | 52 | 5'-CGTACTCGAGTCATCGCGAGCCGATCTCGCCCCAGAAGCCGCCGTCGTCGTG | 20 |
| 20K-NruXho_PavQIPS | 58 | 5'CGTACTCGAGTCATCGCGACGAGGGGATCTGGACGGCGGGAAGCCGCCGTCGTCGTG | 21 |
| 20K-NruXho_WGEI-2 | 52 | 5'-CGTACTCGAGTCATCGCGAGCCGATCTCGCCCCAGGCGAAGCCGCCGTCGTC | 22 |
| 50KB_NruIXhoI | 37 | 5'-TCGTCTCGAGTCGCGATGGGGCCGAAGCGGATGTTGG | 23 |

TABLE 2-continued

Primers used

| Primer | Length nts | Sequence | Sequence ID NO: |
|---|---|---|---|
| 50KB_SphI | 31 | 5'-GGAGGGCATGCCCAACAGCAGCGAGATCACC | 24 |
| 2_50K_NruISpeI | 38 | 5'-CGGCACTAGTTCGCGACCCGATCTCGCCCCAGCGCAGG | 25 |
| 50K_XhoI | 26 | 5' CGCCGAGGGCCGGCTCGAGAGCATCC | 26 |

TABLE 3

PCR reaction programs used

| Step | Program A | B | C | D |
|---|---|---|---|---|
| 1 | 95° C. 5 min | 95° C. 5 min | 98° C. 1 min | 98° C. 1 min |
| 2 | 95° C. 1 min | 95° C. 1 min | 98° C. 30 s | 98° C. 30 s |
| 3 | 55° C. 1 min | 60° C. 1 min | 72° C. 1 min | 65° C. 30 s |
| 4 | 72° C. 1 min | 72° C. 1 min | GOTO 2 29x | 72° C. 1 min |
| 5 | GOTO 2 24x | GOTO 2 24x | 72° C. 10 min | GOTO 2 29x |
| 6 | 4° C. HOLD | 72° C. 1 min | 4° C. HOLD | 72° C. 10 min |
| 7 | | 4° C. HOLD | | 4° C. HOLD |

Figure 3:
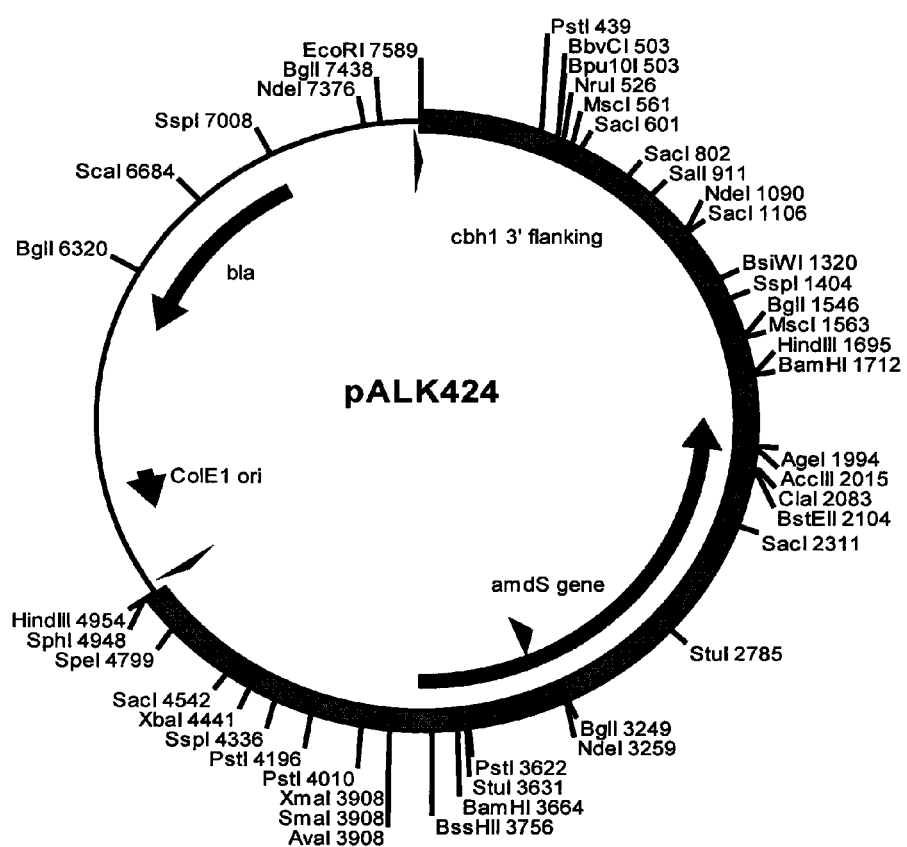
FIG. 3 is the schematic map of the plasmid pALK424.

The amdS marker and *T. reesei* cbh1 3' flanking region were inserted into vectors pALK1430 and pALK1431 as follows: pALK424 (U.S. Pat. No. 5,837,51; FIG. 3) was cut with EcoRI and SpeI, the resulting 4.8 kb fragment was made blunt by the Klenow fill-in reaction, and ligated separately with plasmids pALK1430 and pALK1431 cut with StuI, respectively, and transformed into *E. coli* XL1-Blue. The plasmid DNAs were isolated and the desired orientation of the inserts was checked by digestion with appropriate restriction enzymes. The verified plasmids were designated as pALK1434 (insert from pALK1430) and pALK1435 (insert from pALK1431), respectively (Table 1).

For constructs #3, #4, #5 and #6 set forth in Table 1a different approach was taken. The coding sequence of the 20K and the different modified junction points (Table 1) were designed to end at the serine endocing codon, which forms a part of the added NruI site. For all these constructs the same insert was used to provide the coding sequence of the major part of the linker and CBD. The latter was constructed as follows. A PCR reaction was performed with the reaction mixture described above (except without added $Mg^{2+}$) and using the primer pair 3_BamMly (SEQ ID NO: 18) and Xho-Age (SEQ ID NO: 15) and pALK492 DNA as the template. The program B in Table 3 was used. The resulting PCR product was digested with BamHI and XhoI, isolated and ligated with the similarly cut vector part of pBluescript II KS+ (Stratagene, USA), and transformed into *E. coli* XL1 Blue. The plasmid DNA was isolated, checked by digestion with appropriate restriction enzymes and verified by sequencing. One plasmid candidate with the desired sequence was chosen and designated as pALK1767.

For construct #3 in Table 1a PCR reaction was performed using the primer pair 20K_Nco_2 (SEQ ID NO: 12) and 20K-NruXho_GPI (SEQ ID NO: 19) and pALK1480 DNA as the template. Two reaction mixtures were used: one with the composition described above for the construction of pALK1767, and the other with added DMSO to 3% (v/v). These two reaction mixtures were split, and run with programs C and D in Table 3. All reactions produced DNA fragments of expected size, and the preparations were combined and digested with NcoI and XhoI. The DNA fragment were isolated and ligated with a similarly cut and isolated 6.1 kb fragment of pALK1480, and transformed into *E. coli* XL1 Blue. The plasmid DNA was isolated, checked by digestion with appropriate restriction enzymes and verified by sequencing. One plasmid candidate with the desired sequence was chosen and designated as pALK1758.

For construct #4 in Table 1a PCR reaction was performed using the primer pair 20K_Nco_3 (SEQ ID NO: 13) and 20K-NruXho_WGEI (SEQ ID NO: 20) and pALK1480 DNA as the template. The PCR reaction mixture contained 1× Phusion™ GC reaction buffer (Finnzymes, Finland), 0.2 mM dNTPs, 0.5 µM of each primer, 3% (v/v) DMSO and 1.0 units of Phusion™ DNA polymerase (Finnzymes, Finland) and approximately 70 ng/100 µl of the template. The reaction mixture was split, and run with programs C and D in Table 3. Both reactions produced DNA fragments of expected size, and the preparations were combined and digested with NcoI and XhoI. The DNA fragment was isolated and ligated with a similarly cut and isolated 6.1 kb fragment of pALK1480, and transformed into *E. coli* XL1 Blue. The plasmid DNA were isolated, checked by digestion with appropriate restriction enzymes and verified by sequencing. One plasmid candidate with the desired sequence was chosen and designated as pALK1759.

For construct #5 in Table 1a PCR reaction was performed using the primer pair 20K_Nco_2 (SEQ ID. NO: 12) and 20K-NruXho_PavQIPS (SEQ ID. NO: 21) and pALK1480 DNA as the template. Two reaction mixtures were used: one with the composition described above for the construction of pALK1759, and the other without the DMSO. These two reaction mixtures were split, and run with programs C and D in Table 3. All reactions produced DNA fragments of expected size, and the preparations were combined and digested with NcoI and XhoI. The DNA fragment was isolated and ligated with the similarly cut and isolated 6.1 kb fragment of pALK1480, and transformed into *E. coli* XL1 Blue. The plasmid DNAs were isolated, checked by digestion with appropriate restriction enzymes and verified by sequencing. One plasmid candidate was chosen and designated as pALK1760; it had acquired a mutation in the unique XhoI site, but this posed no problem for further subcloning.

For construct #6 in Table 1a PCR reaction was performed using the primer pair 20K_Nco_3 (SEQ ID. NO: 13) and 20K-NruXho_WGEI-2 (SEQ ID. NO: 22) and pALK1480 DNA as the template (70 ng/100 µl). The same reaction mixture composition was used as for the construction of plasmid pALK1767, and it was run with the program C in Table 3. The preparation was digested with NcoI and XhoI. The DNA fragment was isolated and ligated with a similarly cut and isolated 6.1 kb fragment of pALK1480, and transformed into *E. coli* XL1 Blue. The plasmid DNAs were isolated, checked by digestion with appropriate restriction enzymes and verified by sequencing. One plasmid candidate was chosen and designated as pALK1773.

Plasmids pALK1758, pALK1759, pALK1760 and pALK1773 were separately cut with NruI and AgeI, and the vector parts were isolated. Each preparation was ligated with a 235 by fragment isolated from pALK1767 after MlyI and AgeI digestion, and each ligation mixture was transformed separately into E. coli XL10-Gold. The plasmid DNAs were isolated, checked by digestion with appropriate restriction enzymes and verified by sequencing. The verified plasmids were designated as pALK1764, pALK1765, pALK1766, and pALK1774, respectively (Table 1).

Figure 10:
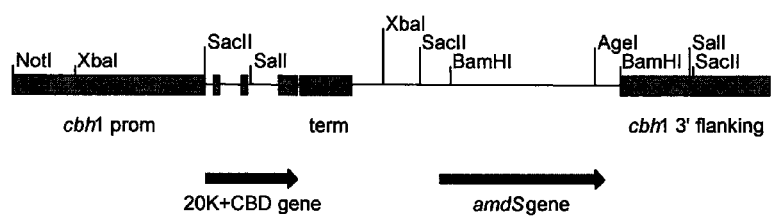
FIG. 10A. The expression cassette used in the transformation of *Trichoderma reesei* protoplasts for producing the 20K+CBD fusion proteins. The 20K+CBD gene was under the control of the cbh1 (cel7A) promoter (cbh1 prom) and termination of transcription was ensured by using the cbh1 terminator sequence (term). The amdS gene (amdS) and the cbhI 3' flanking region (cbhI 3' flanking) were included.
FIG. 10B. Amino acid sequence of a junction point at which *Melanocarpus albomyces* 20K (Cel45A) protein is fused to linker peptide of *Trichoderma reesei* CBHI (Cel7A) followed by the cellulose-binding domain (CBD) in pALK1768, pALK1769, pALK1770 and pALK1775 plasmids (See SEQ ID NOs: 64, 65, 66, 67). The amino acids contained in the linker region are underlined, and the amino acid sequence of the CBD region is marked by italics (SEQ ID NO:63). The first amino acid in the CBD region is indicated by superscript numbers.

The amdS marker and *T. reesei* cbh1 3' flanking region were inserted into vectors pALK1764, pALK1765, pALK1766, and pALK1774 as follows: pALK424 was cut with EcoR1 and Spe1, the resulting 4.8 kb fragment was made blunt by the Klenow fill-in reaction, and ligated separately with plasmids pALK1764, pALK1765, pALK1766, and pALK1774 cut with StuI, respectively, and transformed into E. coli XL10-Gold. Plasmid DNAs were isolated and the desired orientation of the inserts was checked by digestion of appropriate restriction enzymes. The verified plasmids were designated as pALK1768, pALK1769, pALK1770, and pALK1775, respectively (Table 1) (FIG. 10).

Example 2

Production of the Fusion 20K+CBD Proteins in *T. reesei*

8.7 kb linear expression cassettes from the plasmids pALK1434 and pALK1435 were isolated from the vector backbone after EcoRI digestion and transformed to *T. reesei* A47 protoplasts. The transformations were performed as described in Pentla et al. (1987) with the modifications described in Karhunen et al. (1993) selecting with acetamide as the sole nitrogen source. The transformants were purified on selection plates through single conidia prior to sporulating them on PD (Potato Dextrose Agar).

The 20K+CBD production of the transformants was analysed from the culture supernatants of the shake flask cultivations (50 ml). The transformants were grown for 7 days in a complex cellulase-inducing medium (Joutsjoki et al. 1993) buffered with 5% $KH_2PO_4$ at pH 5.5. The enzyme activity of the fusion protein was measured as the release of reducing sugars from carboxymethylcellulose (3% CMC) at 50° C. in 50 mM Hepes buffer pH 7.0 in 10 min (NCU activity, nkat; Bailey and Nevalainen, 1981; Haakana et al., 2004). NCU activities of the best producing transformants are presented in Table 4. The genotypes of the chosen transformants were confirmed by using Southern blots, in which several genomic digests were included and the respective expression cassette was used as a probe. The 20K+CBD protein was detected from the culture supernatants using the polyclonal antibodies raised against the purified *Melanocarpus albomyces* 20K neutral cellulase (Haakana et al. 2004) and the ProtoBlot Western blot AP system (Promega). The Western blot analyses showed that the fusion 20K+CBD enzymes were produced mainly as stable fusion proteins in *T. reesei*.

TABLE 4

NCU activities of the selected 20K + CBD transformants from shake flask cultivations.

| Transformant | Construction No. | RF Number | Neutral cellulase activity, NCU/ml | Endogenous cellulase phenotype |
|---|---|---|---|---|
| A47/pALK1434/#20 | #1 | RF5580 | 3278 | CBHI− |
| A47/pALK1434/#23 | #1 | RF5581 | 2091 | (CBHI+) |
| A47/pALK1434/#37 | #1 | RF5582 | 2330 | CBHI− |
| A47/pALK1435/#3 | #2 | RF5583 | 3624 | CBHI− |
| A47/pALK1435/#7 | #2 | RF5584 | 3211 | CBHI− |
| A47/pALK1435/#11 | #2 | RF5585 | 1172 | (CBHI+) |
| A47/pALK1435/#14 | #2 | RF5586 | 3152 | CBHI− |

In Table 4, the construction number refers to Table 1; RF number refers to that the transformants were named as RF strains.

The possible targeting of the expression cassette to the cbh1 (cel7A) locus was screened as a CBHI-negative phenotype by Western blot. The detection of the CBHI protein was performed using the monoclonal antibodies CI-258 or CI-261 (Aho et al., 1991) and the ProtoBlot Western blot AP system (Promega, USA). The genotypes of the chosen transformants were confirmed by using Southern blots, in which several genomic digests were included and the respective expression cassette was used as a probe.

8.7 kb linear expression cassettes from the plasmids pALK1768, pALK1769, pALK1770, and pALK1775 prepared in Example 1 were isolated from the vector backbone after EcoRI digestion and transformed to *T. reesei* RF5796 and RF5798 protoplasts (both strains originating from the strain QM6a (Bailey and Nevalainen, 1981) and having the phenotype CBHI− CBHII− EGI− EGII− for the endogenous *T. reesei* cellulases) selecting with acetamide as the sole nitrogen source. The transformants were purified on selection plates through single conidia prior to sporulating them on PD.

The 20K+CBD production of the transformants was analyzed from the culture supernatants of the shake flask cultivations (50 ml). The transformants were grown for 7 days in a complex cellulase-inducing medium (Joutsjoki et al. 1993) buffered with 5% $KH_2PO_4$ at pH 5.5. The NCU activity of the produced 20K+CBD fusion proteins was then assayed as described above. NCU activities of the selected transformants are presented in Table 5. The genotypes of the chosen transformants were confirmed by using Southern blots in which several genomic digests were included and the respective expression cassette was used as a probe. The 20K+CBD protein was detected from the culture supernatants using the polyclonal antibodies raised against the purified *M. albomyces* 20K neutral cellulase (Haakana et al. 2004) and the ProtoBlot Western blot AP system (Promega, USA). The Western blot analyses showed that the fusion 20K+CBD enzyme was produced by the transformants. Some cultures showed also a band reacting with the anti-20K antiserum, and having the mobility of the wild type 20K protein, indicating that possibly some cleavage of the linker+CBD had taken place during the cultivation. The 20K+CBD fusion protein produced by the pALK1770 transformants was chosen further studies due to its stability.

TABLE 5

NCU activities of the selected 20K + CBD transformants from shake flask cultivations.

| Transformant | Construction No. | RF number | Neutral cellulase activity, NCU/ml |
|---|---|---|---|
| RF5796/pALK1768/#6 | #3 | RF5966 | 3622 |
| RF5796/pALK1768/#7 | #3 | RF5967 | 1316 |
| RF5796/pALK1768/#9 | #3 | RF6035 | 6605 |
| RF5798/pALK1768/#11 | #3 | RF5970 | 1525 |
| RF5798/pALK1768/#17 | #3 | RF5971 | 2885 |
| RF5798/pALK1768/#20 | #3 | RF5972 | 2598 |
| RF5796/pALK1769/#7 | #4 | RF5968 | 4344 |
| RF5796/pALK1769/#10 | #4 | RF5969 | 4858 |
| RF5796/pALK1769/#11 | #4 | RF6036 | 6145 |
| RF5798/pALK1769/#4 | #4 | RF5973 | 4505 |
| RF5798/pALK1769/#8 | #4 | RF5974 | 4895 |
| RF5796/pALK1770/#13 | #5 | RF5975 | 3073 |
| RF5796/pALK1770/#17 | #5 | RF5976 | 2256 |
| RF5796/pALK1770/#22 | #5 | RF5977 | 2107 |
| RF5798/pALK1770/#10 | #5 | RF5978 | 1907 |
| RF5798/pALK1770/#14 | #5 | RF5979 | 3661 |
| RF5796/pALK1775/#8 | #6 | RF6078 | 2431 |
| RF5796/pALK1775/#13 | #6 | RF6079 | 3505 |
| RF5796/pALK1775/#21 | #6 | RF6080 | 2541 |
| RF5798/pALK1775/#22 | #6 | RF6081 | 1697 |
| RF5798/pALK1775/#29 | #6 | RF6082 | 3096 |

TABLE 6

Reverse PCR primers designed for amplifying mutated CBD products.

| Primer | Length (nts) | Sequence, reverse | Amino acid substitution | Sequence Id. No |
|---|---|---|---|---|
| XhoAge_Y31A | 69 | 5'-TGACTCGAGACCGGTGCGTCAGGCTTTCGCACGGAGCTTTACAGGCACT GAGAGTAGGCAGGGTTCAGG | Y31A | SEQ ID. NO: 27 |
| XhoAge_Y32A | 69 | 5'-TGACTCGAGACCGGTGCGTCAGGCTTTCGCACGGAGCTTTACAGGCACT GAGAGGCGTAAGGGTTCAGG | Y32A | SEQ ID. NO: 28 |
| XhoAge_Y31W | 69 | 5'-TGACTCGAGACCGGTGCGTCAGGCTTTCGCACGGAGCTTTACAGGCACT GAGAGTACCAAGGGTTCAGG | Y31W | SEQ ID. NO: 29 |
| XhoAge_Y31A-Y32A | 69 | 5'-TGACTCGAGACCGGTGCGTCAGGCTTTCGCACGGAGCTTTACAGGCA CTGAGAGGCGGCAGGGTTCAGG | Y31A_Y32A | SEQ ID. NO: 30 |

In Table 5, the construction number refers to Table 1; RF number refers to that the transformants were named as RF strains.

*T. reesei* strains RF5582, RF5583, RF6036, RF5977, and RF5978 were grown in a bioreactor for applications tests. Some preparations were heat treated (pH 6.0, 65° C., 60-70 min) in order to inactivate any remaining *T. reesei* endogenous enzyme activity. The 20K+CBD is relatively heat stable (Miettinen-Oinonen et al. 2004), and does not denature during the treatment.

Example 3

Production of the Fusion 20K+CBD Affinity Mutant Proteins in *T. reesei*

*Melanocarpus albomyces* 20K (cel45A, AC#AJ515703) enzyme was fused to the cellulose-binding domain (CBD) of *Trichoderma reesei* CBHI, in which the conserved tyrosine residues at positions 31 (corresponding to Y492 of the mature polypeptide) and/or 32 (corresponding to Y493 of the mature polypeptide) were mutated to alanine as described by Linder et al., 1995. In addition, the tyrosine residue at position 31 was replaced by tryptophan, an amino acid naturally found in the CBD region of e.g., *Humicola grisea* CBHI (Azevedo et al., 1990) and *T. reesei* EGV (Cel45A, Saloheimo et al., 1994). The mutated CBDs were constructed by PCR, and the amino acid substitutions of Y31A, Y32A, Y31W and Y31A_Y32A were included in the cellulose-binding domain of *T. reesei* CBHI (numbering according to amino acid sequence of CBD). In all constructs, the forward primer 3_BamMly: 5'-TAGGATCCGAGTCCCATTACCG-GCAACCCTAGCG-3' (SEQ ID. NO: 18) was used. The reverse primers used for the amplification of different $CBD_{mut}$ products are described in Table 6. The PCR reaction mixtures contained 1×PfuUltra™ HF reaction buffer (Stratagene, USA) providing 2 mM $Mg^{2+}$ concentration, 0.2 mM dNTPs, 2 µM of each primer and 1.5 units of PfuUltra™ HF DNA polymerase (Stratagene, USA) and approximately 45 ng of pALK492 plasmid as a template. The pALK492 (FIG. 2) plasmid contains the *T. reesei* cbh1 gene. The conditions for the PCR reactions were the following: 2 min initial denaturation at 95° C., followed by 30 cycles of 1 min at 95° C., 1 min annealing at 65° C. (±5° C. gradient), 2 min extension at 72° C. and a final extension at 72° C. for 10 min.

Figure 6:
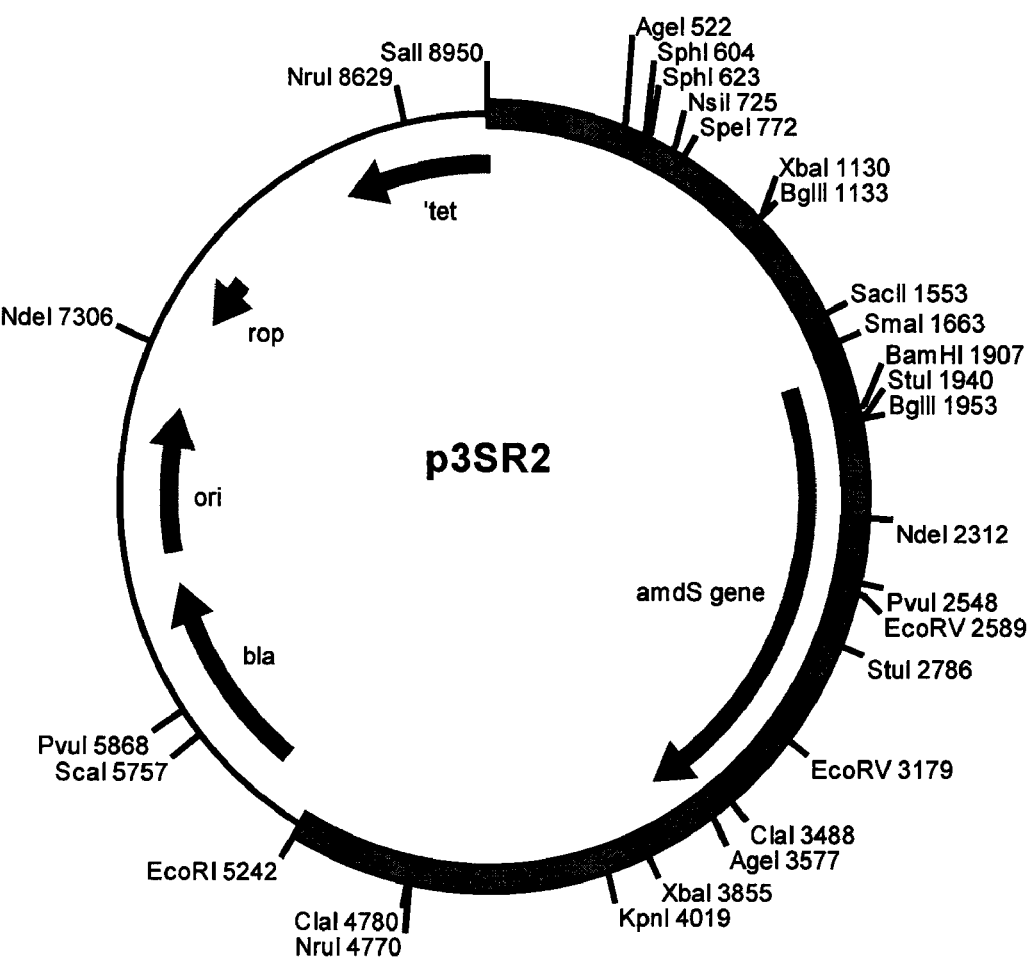
FIG. 6 is the schematic map of the plasmid p3SR2.
Figure 11:
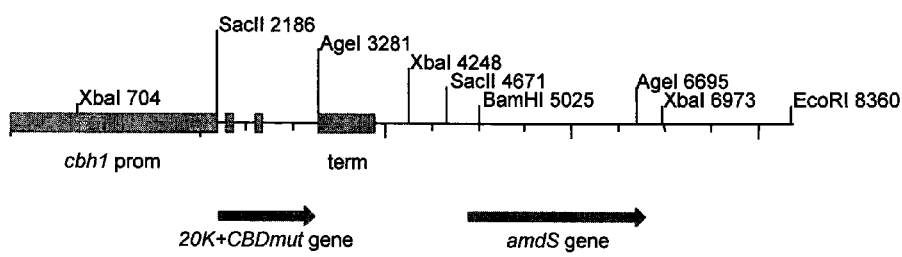
FIG. 11A. The expression cassette used in the transformation of *Trichoderma reesei* protoplasts for producing the 20K+CBD$_{mut}$ fusion proteins. The 20K+CBD$_{mut}$ gene was under the control of the cbh1 (cel7A) promoter (cbh1 prom) and termination of transcription was ensured by using the cbh1 terminator sequence (term). The amdS gene was included as a transformation marker.
FIG. 11B. Amino acid sequence of a junction point at which *Melanocarpus albomyces* 20K (Cel45A) protein is fused to linker peptide of *Trichoderma reesei* CBHI (Cel7A) followed by the cellulose-binding domain (CBD) (See SEQ ID NOs: 68, 69, 70). The amino acid substitutions in the CBD region of the pALK1877-pALK1880 expression cassettes are also presented (See SEQ ID NOs: 71, 72, 73, 74). The amino acids contained in the linker region are underlined, and the amino acid sequence of the CBD region is marked by italics. The first amino acid and the tyrosine residues or their substitutions in the CBD region are indicated by superscript numbers.

All primer combinations produced the specific DNA fragment in PCR reactions at annealing temperature of 60° C. The PCR products were isolated from these reactions, digested with XhoI and BamHI restriction enzymes and then cloned to pBluescript II KS+ (Stratagene, USA). The plasmids obtained were named as pALK1884 (Y31A mutation), pALK1885 (Y32A mutation), pALK1886 (Y31W mutation) and pALK1887 (Y31A_Y32A mutations). The PCR fragments in the plasmids were confirmed by sequencing. The MlyI and AgeI digested inserts of the plasmids pALK1884 to pALK1887 were further ligated to a NruI and AgeI digested pALK1760 vector fragment containing the full-length *Melanocarpus albomyces* 20K gene fused to the *T. reesei* cbh1 (cel7A) promoter and terminator. The C-terminal part of the 20K gene in pALK1760 was modified so that ligation of the CBD fragment produced a junction point of PAVQIPSS (construct #5), which was shown to result in a stable fusion product in *T. reesei* as described in Examples 1 and 2. At the final step, the amdS marker was added as a blunt-ended SpeI-EcoRI fragment (4.5 kb) of p3SR2 plasmid (FIG. 6) to obtain expression plasmids of pALK1877 (Y31A mutation), pALK1878 (Y32A mutation), pALK1879 (Y31W mutation), and pALK1880 (Y31A_Y32A mutation) for production of fusion 20K+$CBD_{mut}$ enzymes in *T. reesei*. The amino acid sequences of the 20K protein fusion to linker peptide followed by the mutated CBD region are presented in FIG. 11B. The expression plasmids were confirmed by sequencing, and the 8.4 kb linear expression cassettes (FIG. 11A) were isolated from the vector backbone after NotI digestion and were transformed to *T. reesei* RF5796 protoplasts. The transformations were performed in Penttilä et al. (1987) with the modifications described in Karhunen et al. (1993), selecting with acetamide as a sole nitrogen source. The transformants were purified on selection plates through single conidia prior to sporulating them on PD.

The 20K+CBD$_{mut}$ production of the transformants was analysed from the culture supernatants of the shake flask cultivations (50 ml). The transformants were grown for 7 days in a complex cellulase-inducing medium (Joutsjoki et al. 1993) buffered with 5% $KH_2PO_4$ at pH 5.5. The enzyme activity of the fusion protein was measured as the release of reducing sugars from carboxymethylcellulose (3% CMC) at 50° C. in 50 mM Hepes buffer pH 7.0 in 10 min (NCU activity, nkat; Bailey and Nevalainen, 1981; Haakana et al., 2004). NCU activities of the best producing transformants are presented in Table 7. The genotypes of the chosen transformants were confirmed by using Southern blots in which several genomic digests were included and the respective expression cassette was used as a probe. The 20K+CBD$_{mut}$ protein was detected from the culture supernatants using polyclonal antibodies raised against the purified *Melanocarpus albomyces* 20K neutral cellulase (Haakana et al. 2004) and the ProtoBlot Western blot AP system (Promega). The Western blot analyses showed that the fusion 20K+CBD$_{mut}$ enzymes were produced as stable fusion proteins in *T. reesei*.

TABLE 7

NCU activities of the selected 20K + CBD$_{mut}$ transformants from shake flask cultivation

| Transformant | Amino acid substitution | RF number | Neutral cellulase activity, NCU/ml |
|---|---|---|---|
| pALK1877/#26 | Y31A | RF6084 | 3658 |
| pALK1877/#34 | Y31A | RF6085 | 2447 |
| pALK1878/#02 | Y32A | RF6086 | 3434 |
| pALK1878/#13 | Y32A | RF6088 | 2915 |
| pALK1879/#13 | Y31W | RF6090 | 2545 |
| pALK1879/#24 | Y31W | RF6091 | 3452 |
| pALK1880/#06 | Y31A_Y32A | RF6092 | 3415 |
| pALK1880/#25 | Y31A_Y32A | RF6094 | 2727 |

RF number refers to that the transformants were named as RF strains.

The strains RF6084 to RF6086, RF6088, RF6090 to RF6092 and RF6094 were fermented to obtain material for the application tests (see EXAMPLES 9-11).

Example 4

Production of the Fusion 20K+CBD Linker Deletion Proteins in *T. reesei*

*Melanocarpus albomyces* 20K enzyme was fused to the cellulose-binding domain (=CBD) of *Trichoderma reesei* CBHI, which was further modified by introducing deletions to the interdomain linker peptide. Linker deletions were designed according to Srisodsuk et al., 1993. Deletion of amino acids from position 434 to 444 (Mutant ΔG-444) of the mature polypeptide removes approximately one-third of the linker including the glycine- and proline-rich repeated sequence but leaving all the putative O-glycosylation sites intact. Deletion of residues from position 434 to 460 (Mutant ΔG-460) removes practically all of the linker (FIG. 12A). Additional 20K+CBD linker deletions having an affinity double mutation of Y31A_Y32A in the CBD region were also constructed.

PCR reactions were performed to introduce the deletions to linker peptide as well as the amino acid substitution to the CBD region. The PCR amplifications were done as described in Example 3, except that the annealing temperature of 60° C. (±5° C. gradient) was used. The forward primers

```
                                             (SEQ ID. NO: 31)
5'-TAGGATCCGAGTCCCATTACCGGCAACCCTAGCACCACCACCA-

CCCGCCGCCCAGCC-3'
and
                                             (SEQ ID. NO: 32)
5'-TAGGATCCGAGTCCCATTACCGGCAACCCTAGCCC-

TACCCAGTCTCACTACGGCCAGTGC-3'
``` were used for synthesizing the linker deletions of ΔG-444 and ΔG-460, respectively. Correspondingly, the reverse primer

```
                                             (SEQ ID. NO: 33)
5'-TGACTCGAGACCGGTGCGTCAGGCTTTCGCACGGAGCTTTACAGG-3
``` was used to amplify the intact CBD region of the *T. reesei* CBHI. The Y31A_Y32A mutation to the CBD region was generated with the reverse primer

```
                                             (SEQ ID. NO: 30)
5'-TGACTCGAGACCGGTGCGTCAGGCTTTCGCACGGAGCTT-

TACAGGCACTGAGAGGCGGCAGGGTTCAGG-3'
```

All primer combinations produced the specific DNA fragment in PCR reactions from 55.2° C. to 65.0° C. range of annealing temperatures. Expression plasmids pALK1893 (ΔG-444 deletion), pALK1896 (ΔG-460 deletion), pALK1899 (ΔG-444 deletion, Y31A_Y32A mutation), and pALK1952 (ΔG-460 deletion, Y31A_Y32A mutation) were constructed as described in Example 3. The amino acid sequences of the 20K protein fusion to truncated linker peptide followed by the intact or mutated CBD are presented in FIG. 12B. The 8.3 kb linear expression cassettes were isolated from the vector backbone after EcoRI digestion and were transformed to *T. reesei* RF5796 protoplasts. Transformation, transformant purification, shake flask cultivations, activity measurements, Southern blot hybridizations, and Western blot analyses were performed as described in Example 3.

TABLE 8

NCU activities of the selected 20K + CBD linker deletion transformants from shake flask cultivation

| Transformant | Linker Deletion/ Amino acid substitution | RF number | Neutral cellulase activity, NCU/ml |
|---|---|---|---|
| pALK1893/#08 | ΔG-444 | RF6107 | 1182 |
| pALK1893/#10 | ΔG-444 | RF6108 | 2058 |
| pALK1896/#05 | ΔG-460 | RF6110 | 2576 |
| pALK1896/#07 | ΔG-460 | RF6111 | 2628 |
| pALK1899/#07 | ΔG-444, Y31A_Y32A | RF6112 | 1947 |
| pALK1899/#20 | ΔG-444, Y31A_Y32A | RF6114 | 2462 |

TABLE 8-continued

NCU activities of the selected 20K + CBD linker deletion
transformants from shake flask cultivation

| Transformant | Linker Deletion/ Amino acid substitution | RF number | Neutral cellulase activity, NCU/ml |
|---|---|---|---|
| pALK1952/#01 | ΔG-460, Y31A__Y32A | RF6115 | 2428 |
| pALK1952/#17 | ΔG-460, Y31A__Y32A | RF6116 | 1738 |

RF number refers to that the transformants were named as RF strains.

The selected strains RF6107, RF6108, RF6110 to RF6112, and RF6114 to RF6116 were fermented to obtain material for the application tests (Examples 9 to 11). The Western blot analyses showed that the fusion 20K+CBD linker deletion enzymes were produced as stable fusion proteins in *T. reesei*.

Example 5

Production of the Recombinant *Melanocarpus albomyces* 50K+CBD Fusion Protein in *T. reesei*

Figure 4:
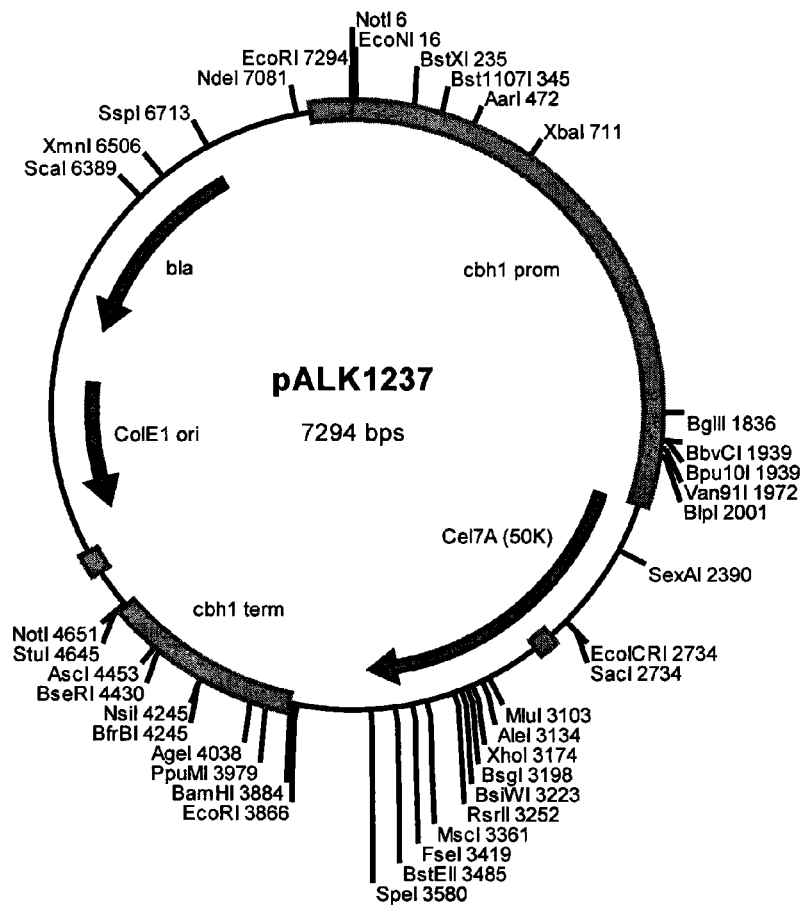
FIG. 4 is the schematic map of the plasmid pALK1237.

Plasmid constructs were designed to join the *Melanocarpus albomyces* 50K (cel7A, AC#AJ515704) coding sequence with the linker region and cellulose binding domain (CBD) of the *T. reesei* CBHI (cel7A, AC#AR088330; Srisodsuk et al. 1993). Plasmid pALK1237 (FIG. 4), which is a basis for the new constructs, contains the cel7A gene under control of *T. reesei* cbh1 promoter as an exact fusion.

Figure 13:
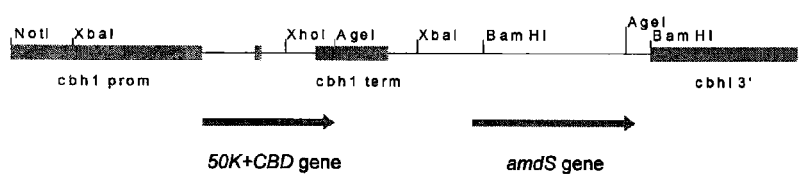
FIG. 13A. The expression cassette used in transformation of *Trichoderma reesei* protoplasts for production of the 50K+CBD fusion protein. The 50K+CBD gene is under control of *T. reesei* cbhI promoter (cbhI prom) and transcription termination is ensured with the addition of the cbhI terminator (term). The amdS gene (amdS) and the cbhI 3' flanking region (cbhI 3') are included.
FIG. 13B. Amino acid sequence of the junction point of the *M. albomyces* 50K linked to the *T. reesei* CBHI linker+CBD (See SEQ ID NOs: 80, 81, 82). The amino acids contained in the linker region are underlined, and the amino acid sequence of the CBD region is marked by italics. The first amino acid in the CBD region is indicated by superscript numbers.

First, a unique NruI restriction site was introduced near the C-terminus of the 50K coding sequence. This enables direct fusion of any blunt-ended DNA after amino acid S393 of the mature 50K polypeptide (FIG. 13B). A PCR reaction was performed with primers 2_50K_NruISpeI (5' CGGCACTAGTTCGCGACCCGATCTCGCCCCAGCGCAGG 3'; SEQ ID. NO: 25) and 50K_XhoI (5' CGCCGAGGGCCGGCTCGAGAGCATCC 3'; SEQ ID. NO: 26) using pALK1237 as a template. The PCR reaction contained 1× DyNAzyme™ EXT reaction buffer (Finnzymes, Finland), 0.25 mM dNTPs, 0.5 μM of each primer, 2.0 units of DyNAzyme™ EXT DNA polymerase (Finnzymes, Finland) and approximately 50 ng/100 μl of pALK1237 template DNA. The conditions for PCR amplification was as follows: 5 min initial denaturation at 96° C., followed by 25 cycles of 15 s at 96° C., 60 s annealing at 56° C. or 61° C., 60 s extension at 72° C., and a final extension at 72° C. for 10 min. The PCR product was digested with XhoI and SpeI restriction enzymes and purified from the agarose gel. The purified PCR fragment was ligated into the 6.9 kb XhoI-SpeI restriction fragment of plasmid pALK1237 and transformed into *E. coli* XL1-Blue (Stratagene, USA). Plasmid DNA was isolated from the transformants and three candidates were verified by sequencing. The selected clone was designated as pALK1703.

The *T. reesei* CBHI linker+CBD was amplified by PCR with primers 3_BamMly_50 (5' TTGGATCCGAGTCGCAGCACCGGCAACCCTAGCG 3'; SEQ ID. NO: 36) and XhoAge (5' TGACTCGAGACCGGTGCGTCAGGCTTTCGC 3'; SEQ ID. NO: 15) using pALK492 as a template. The PCR reaction conditions were as described above, except that the extension time in the amplification reaction was 90 s. The PCR product was digested with MlyI and AgeI enzymes and purified from the agarose gel. The linker+CBD containing PCR fragment was ligated into the 6.8 kb AgeI-NruI restriction fragment of pALK1703 and transformed into *E. coli* XL1-Blue (Stratagene, USA). Transformants were analyzed as described above and a suitable clone was designated as pALK1704.

To enable selection of *T. reesei* transformants the amdS marker gene and the *T. reesei* cbhI 3' flanking region was inserted into the vector plasmid pALK1704. A 4.8 kb EcoRI-SpeI restriction fragment of pALK424 (U.S. Pat. No. 5,837,515) was isolated and the fragment ends were filled-in with Klenow enzyme. The blunt-ended amdS marker fragment was ligated into the StuI digested pALK1704 and transformed into *E. coli* XL1-Blue (Stratagene, USA). Plasmid DNA was isolated from transformants and the desired orientation of the insert was verified by restriction enzyme digestion. The selected transformant was designated as pALK1708.

A 9.2 kb linear expression cassette (FIG. 13A) from pALK1708 backbone was isolated by EcoRI digestion, transformed into *T. reesei* RF5636 protoplasts (derived from the strain QM6a; Bailey and Nevalainen, 1981), and transformants selected with acetamide as sole nitrogen source. The host strain lacks three major endogenous cellulases: CBHII (Cel6A), EGI (Cel7B) and EGII (Cel5A). Transformation was performed according to Penttilä et al. (1987) with modifications described by Karhunen et al. (1993). Transformants were purified on selection plates through single conidia prior to sporulating them on PD.

The production of 50K+CBD fusion protein of the transformants was analyzed from the culture supernatants of shake flask cultivations (50 ml). Transformants were grown for 7 days in a complex cellulose-inducing medium (Joutsjoki et al. 1993) buffered with 5% KH$_2$PO$_4$ at pH 5.5. The enzyme activity of the fusion protein was measured as the release of reducing sugars from carboxymethylcellulose (3% CMC) at 50° C. in 50 mM Hepes buffer pH 7.0 (NCU activity; Bailey and Nevalainen 1981; Haakana et al. 2004). The activity of the transformants varied from 2035 to 3633 NCU/ml. The 50K+CBD protein was detected from the culture supernatants by ProtoBlot Western blot AP system (Promega) using polyclonal antibodies raised against the purified *Melanocarpus albomyces* 50K neutral cellulase (Haakana et al. 2004). The Western blot analysis showed that the 50K+CBD fusion protein produced from *T. reesei* is stable. The genotypes of the chosen transformants were analysed by Southern blotting using the expression cassette as a probe. The possible targeting of the expression cassette to the cbhI locus was also verified by Western blotting using monoclonal CBHI antibodies (CI-261, Aho et al. 1991) to detect CBHI protein.

Example 6

Production of the Recombinant *Melanocarpus albomyces* 50KB+CBD Fusion Protein in *T. reesei*

Figure 5:
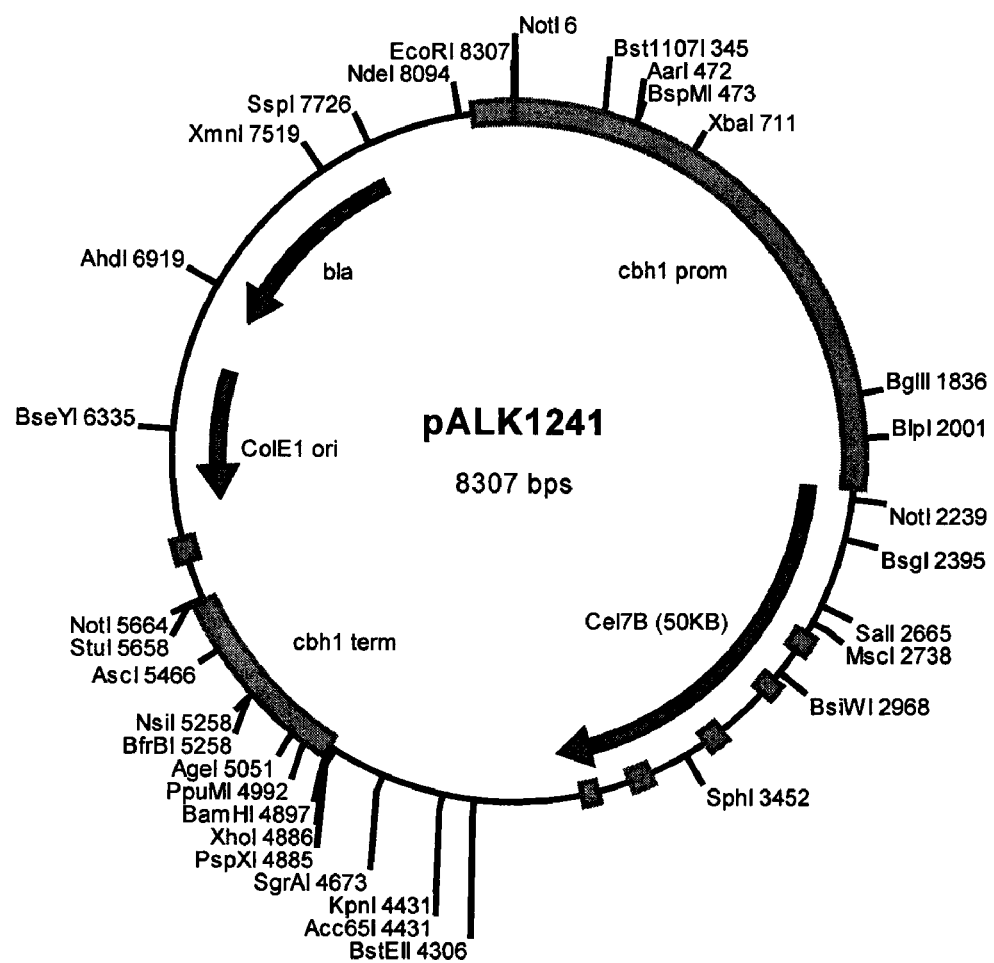
FIG. 5 is the schematic map of the plasmid pALK1241.

Plasmid constructs were designed to join the *Melanocarpus albomyces* 50KB (cel7B, AC#AJ515705) coding sequence with the linker region and cellulose binding domain (CBD) of the *T. reesei* CBHI (cel7A, AC#AR088330; Srisodsuk et al. 1993). Plasmid pALK1241 (FIG. 5), which is a basis for the new constructs, contains the cel7B gene under control of *T. reesei* cbh1 promoter as an exact fusion.

Figure 14:
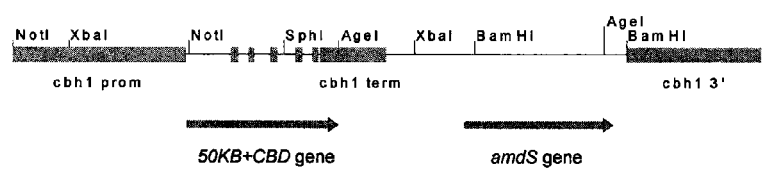
FIG. 14A. The expression cassette used in transformation of *Trichoderma reesei* protoplasts for production of the 50KB+CBD fusion protein. The 50KB+CBD gene is under control of *T. reesei* cbhI promoter (cbhI prom) and transcription termination is ensured with the addition of the cbhI terminator (term). The amdS gene (amdS) and the cbhI 3' flanking region (cbhI 3') are included.
FIG. 14B. Amino acid sequence of the junction point of the *M. albomyces* 50KB linked to the *T. reesei* CBHI linker+CBD (See SEQ ID NOs: 81, 82, 83). The amino acids contained in the linker region are underlined, and the amino acid sequence of the CBD region is marked by italics. The first amino acid in the CBD region is indicated by superscript numbers.

First, a unique NruI restriction site was introduced near the C-terminus of the 50KB coding sequence. This enables direct fusion of any blunt-ended DNA after amino acid S426 of the mature 50KB polypeptide (FIG. 14B). A PCR reaction was performed with primers 50KB_NruIXhoI (5' TCGTCTCGAGTCGCGATGGGCCGAAGCGGATGTTGG 3'; SEQ ID. NO: 23) and 50KB_SphI (5' GGAGGGCATGCCCAACAGCAGCGAGATCACC 3'; SEQ ID. NO: 24) using pALK1241 as a template. The PCR reaction contained 1× DyNAzyme™ EXT reaction buffer (Finnzymes, Finland), 0.25 mM dNTPs, 0.5 µM of each primer, 2.0 units of DyNAzyme™ EXT DNA polymerase (Finnzymes, Finland) and approximately 50 ng/100 µl of pALK1241 template DNA. The conditions for PCR amplification was as follows: 5 min initial denaturation at 96° C., followed by 25 cycles of 15 s at 96° C., 60 s annealing at 56° C. or 60° C., 60 s extension at 72° C., and a final extension at 72° C. for 5 min. The PCR product was digested with XhoI and SphI restriction enzymes and purified from the agarose gel. The purified PCR fragment was ligated into the 6.9 kb XhoI-SphI restriction fragment of plasmid pALK1241 and transformed into *E. coli* XL 1-Blue (Stratagene, USA). Plasmid DNA was isolated from the transformants and one candidate was verified by sequencing. The selected clone was designated as pALK1705.

The *T. reesei* CBHI linker+CBD was amplified by PCR with primers 3_BamMly_50 (5' TTGGATCCGAGTCGC AGCACCGGCAACCCTAGCG 3'; SEQ ID. NO: 18) and XhoAge (5' TGACTCGAGACCGGTGCGTCAG-GCTTTCGC 3'; SEQ ID NO:15) using pALK492 as a template. The PCR reaction conditions were as described above, except that the extension time in the amplification reaction was 90 s. The PCR product was digested with MlyI and AgeI enzymes and purified from the agarose gel. The linker+CBD containing PCR fragment was ligated into the 7.2 kb AgeI-NruI restriction fragment of pALK1705 and transformed into *E. coli* XL 1-Blue (Stratagene, USA). Transformants were analyzed as described above and a suitable clone was designated as pALK1706.

To enable selection of *T. reesei* transformants the amdS marker gene and the *T. reesei* cbhI 3' flanking region were inserted into the vector plasmid pALK1706. A 4.8 kb EcoRI-SpeI restriction fragment of pALK424 (U.S. Pat. No. 5,837,515) was isolated and the fragment ends were filled-in with Klenow enzyme. The blunt-ended amdS marker fragment was ligated into the StuI digested pALK1706 and transformed into *E. coli* XLI-Blue (Stratagene, USA). Plasmid DNA was isolated from transformants and the desired orientation of the insert was verified by restriction enzyme digestion. The selected transformant was designated as pALK1709.

A 9.6 kb linear expression cassette (FIG. 14A) from pALK1709 backbone was isolated by EcoRI digestion, transformed into *T. reesei* RF5636 protoplasts, and transformants selected with acetamide as sole nitrogen source. The host strain lacks three major endogenous cellulases: CBHII (Cel6A), EGI (Cel7B) and EGII (Cel5A). Transformation was performed according to Penttilä et al. (1987) with modifications described by Karhunen et al. (1993). Transformants were purified on selection plates through single conidia prior to sporulating them on PD.

The production of 50KB+CBD fusion protein of the transformants was analyzed from the culture supernatants of shake flask cultivations (50 ml). Transformants were grown for 7 days in a complex cellulose-inducing medium (Joutsjoki et al. 1993) buffered with 5% $KH_2PO_4$ at pH 5.5. The cellobiohydrolase activity of the fusion protein was measured using 4-methylumbelliferyl-β-D-lactoside substrate (MUL activity; van Tilbeurgh et al. 1988). The 50KB+CBD protein was detected from the culture supernatants by ProtoBlot Western blot AP system (Promega) using polyclonal antibodies raised against the purified *Melanocarpus albomyces* 50KB cellulase (Haakana et al. 2004). In Western blot analysis no wild type 50KB protein was detected showing that the 50KB+CBD fusion protein produced from *T. reesei* is stable. The genotypes of the chosen transformants were analysed by Southern blotting using the expression cassette as a probe. The possible targeting of the expression cassette to the cbhI locus was also verified by Western blotting using monoclonal CBHI antibodies (CI-261, Aho et al. 1991) to detect CBHI protein.

Example 7

Production of the Recombinant *Thermoascus aurantiacus* CBHI+CBD Fusion Proteins in *T. reesei*

*Thermoascus aurantiacus* CBHI (AC#AF478686, Hong et al., 2003; SEQ ID. NO: 9) was fused to linker and CBD of *Trichoderma reesei* CBHI (AC#AR088330, Srisodsuk et al. 1993; SEQ ID. NO: 3). First, the coding sequence of the linker and the CBD of *T. reesei* CBHI was synthesized by PCR using following primers:

```
                             (forward sequence, SEQ ID. NO: 34)
5'-TTAAACATATGTTATCTACTCCAACATCAAGGTCGGACCCATTGGC A-GCACCGGCAACCCTAGCGGC-3'
and
                             (reverse sequence, SEQ ID. NO: 35)
5'-TATATGCGGCCGCACCGGTGCGTCAGGCTTTCGCACGGAGCTTT

ACAGGC-3'.
```

Figure 7:
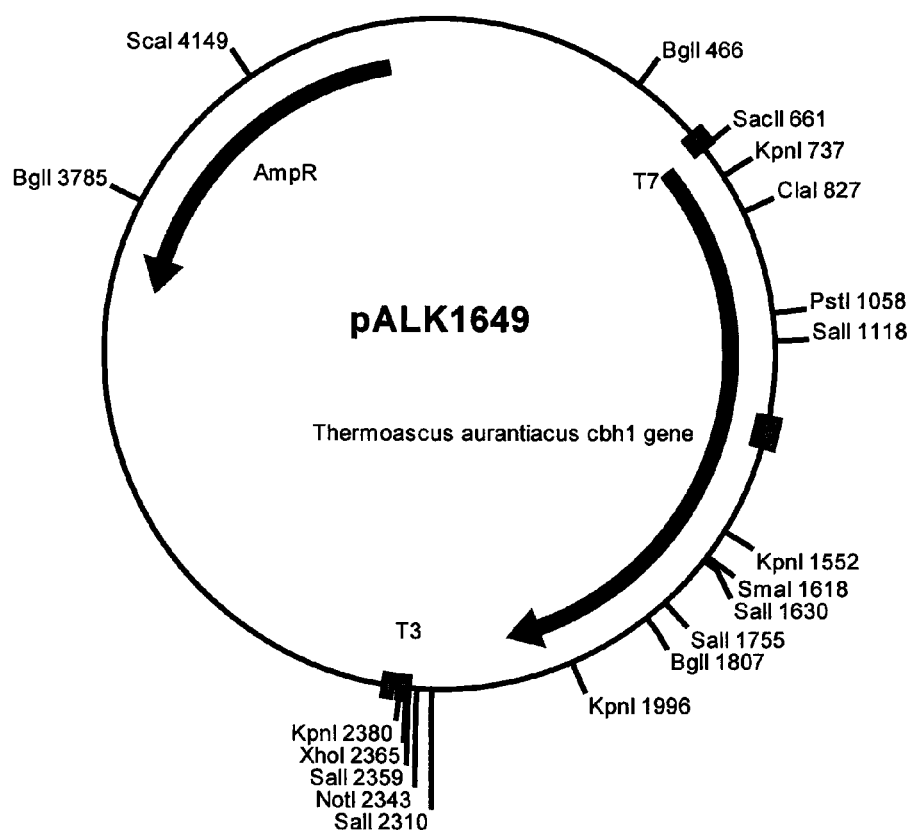
FIG. 7 is the schematic map of the plasmid pALK1649.
Figure 8:
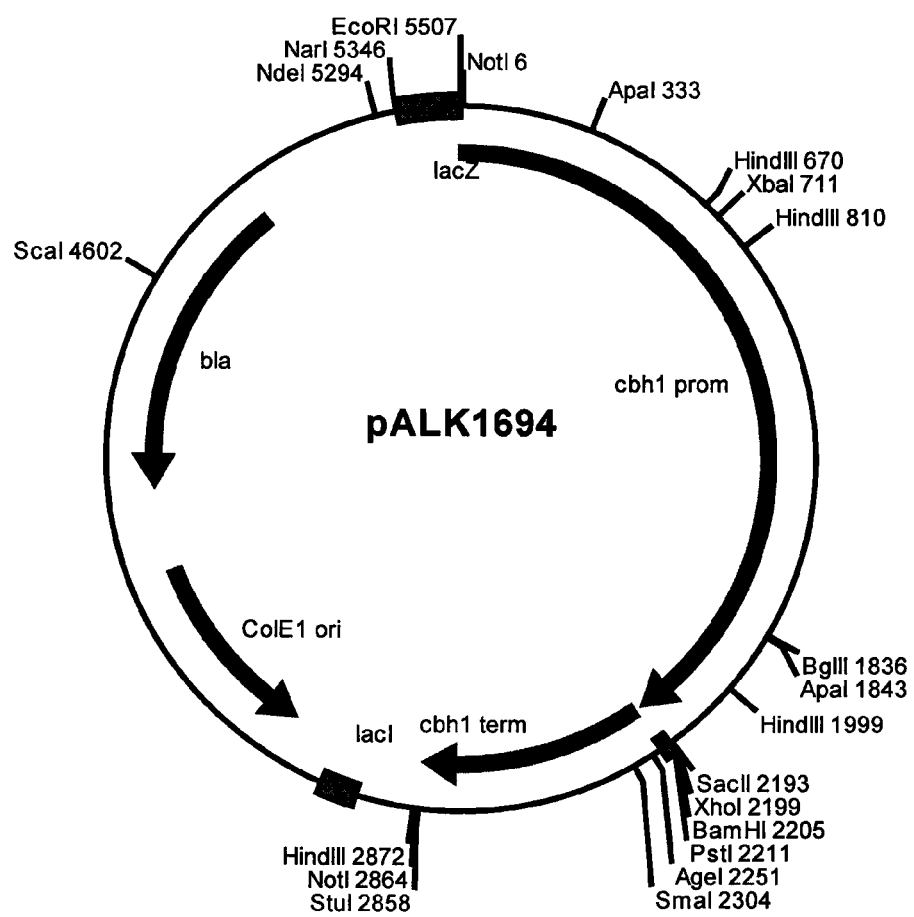
FIG. 8 is the schematic map of the plasmid pALK1694.
Figure 9:
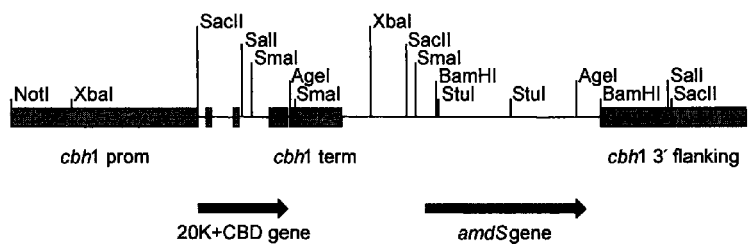
FIG. 9A. The expression cassette used in the transformation of *Trichoderma reesei* protoplasts for producing the 20K+CBD fusion proteins. The 20K+CBD gene was under the control of the cbh1 (cel7A) promoter (cbh1 prom) and termination of transcription was ensured by using the cbh1 terminator sequence (term). The amdS gene (amdS) and the cbhI 3' flanking region (cbhI 3' flanking) were included.
FIG. 9B. Amino acid sequence of a junction point at which *Melanocarpus albomyces* 20K (Cel45A) protein is fused to linker peptide of *Trichoderma reesei* CBHI (Cel7A) followed by the cellulose-binding domain (CBD) in pALK1434 and pALK1435 plasmids (See SEQ ID NOs: 61, 62, 63). The amino acids contained in the linker region are underlined, and the amino acid sequence of the CBD region is marked by italics. The first amino acid in the CBD region is indicated by superscript numbers.
Figure 15:
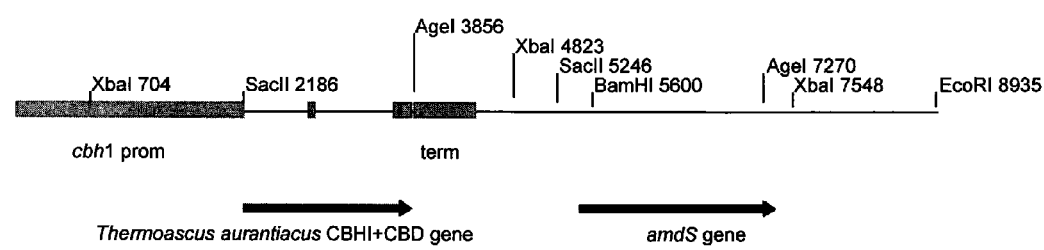
FIG. 15A. The expression cassette used in the transformation of *Trichoderma reesei* protoplasts for producing the recombinant *Thermoascus aurantiacus* CBHI+CBD fusion proteins. The CBHI+CBD gene was under the control of the cbh1 (cel7A) promoter (cbh1 prom) and termination of transcription was ensured by using the cbh1 terminator sequence (term). The amdS gene was included as a transformation marker.
FIG. 15B. Amino acid sequence of a junction point at which *Thermoascus aurantiacus* CBHI protein is fused to linker peptide of *Trichoderma reesei* CBHI followed by the cellulose-binding domain (CBD) (See SEQ ID NOs: 81, 82, 84). The amino acids contained in the linker region are underlined, and the amino acid sequence of the CBD region is marked by italics. The first amino acid in the CBD region is indicated by superscript numbers.

The PCR reaction mixture contained 1× DyNAzyme™ EXT reaction buffer (Finnzymes, Finland), 15 mM $Mg^{2+}$, 0.2 mM dNTPs, 2 µM of each primer, 0.6 units of DyNAzyme™ EXT DNA polymerase (Finnzymes, Finland), and approximately 75 ng/30 µl of the pALK492 template. The pALK492 plasmid contains the *T. reesei* cbh1 (cel7A) gene. The conditions for the PCR reaction were the following: 2 min initial denaturation at 98° C., followed by 30 cycles of 30 sec at 98° C., 30 sec annealing at 68° C. (±4° C. gradient), 30 sec extension at 72° C. and a final extension at 72° C. for 10 min. The specific DNA fragment in PCR reaction was obtained at annealing temperature range from 64° C. to 68.5° C. The synthesized CBD fragment, containing also 3'-terminal nucleotide sequence of *Thermoascus aurantiacus* cbh1 gene, was digested NdeI and NotI restriction enzymes and the fragment was isolated from the agarose gel after electrophoresis. Thereafter, the isolated PCR fragment was ligated to the NdeI and NotI digested pALK1649 (FIG. 7) vector fragment containing the full-length *Thermoascus aurantiacus* cbh1 gene. The plasmid obtained was named as pALK1888, and the PCR amplified fragment in the plasmid was confirmed by sequencing. As a result of fusion, the C-terminal part of the *Thermoascus aurantiacus* CBHI in the pALK1888 plasmid contains a junction point of GPIGST (FIG. 15B). The SacII and AgeI digested insert of the plasmid pALK1888 was ligated to SacII and AgeI digested pALK1694 (FIG. 8) vector fragment, which results to *Thermoascus aurantiacus* CBHI+CBD fusion to *T. reesei* cbh1 (cel7A) promoter (an exact fusion) and terminator. At the final step, the amdS marker fragment was added, as described in Example 3, to obtain expression plasmid of pALK1890 for production of recombinant *Thermoascus aurantiacus* CBHI+CBD fusion enzyme in *T. reesei*. The amino acid sequence of the *Thermoascus aurantiacus* CBHI protein fusion to linker peptide followed by the CBD region of *T. reesei* CBHI is presented in FIG. 15B.

The expression plasmid was confirmed by restriction enzyme digestions, and the 8.9 kb linear expression cassette (FIG. 15A) was isolated from the vector backbone after NotI digestion and was transformed to *T. reesei* RF5796 protoplasts. The transformations were performed as in Penttilä et al. (1987) with the modifications described in Karhunen et al. (1993). The transformants were purified on selection plates through single conidia prior to sporulating them on PD.

*Thermoascus aurantiacus* CBHI+CBD production of the transformants was analyzed from the culture supernatants of the shake flask cultivations (50 ml). The transformants were grown for 7 days in a complex cellulase-inducing medium (Joutsjoki et al. 1993) buffered with 5% $KH_2PO_4$ at pH 5.5. The cellobiohydrolase activity was assayed using 4-methylumbelliferyl-β-D-lactoside (MUL) substrate according to van Tilbeurgh et al., 1988. The genotypes of the chosen transformants were confirmed by using Southern blots in which several genomic digests were included and the expression cassette was used as a probe. The SDS-PAGE analyses showed that the recombinant *Thermoascus aurantiacus* CBHI+CBD enzyme was produced as stable fusion protein in *T. reesei*.

Example 8

Performance of the Fusion 20K+CBD Protein Preparations in Denim Finishing/Biostoning 20K+CBD fusion proteins produced using *Trichoderma* as host as described in Example 2 were tested for their ability in biostoning of denim to create abraded look similar to that provided by pumice stones. A commercial 20K preparation efficient in denim finishing was used for comparison.

English jeans made of Indigo dyed denim twill with sulphur bottom were used as test material after desizing with ECOSTONE® A200 alpha-amylase. Warp and weft yarns of the fabric were ring spun. The cellulase treatments were performed with Electrolux's Wascator FOM 71 CLS washer extractor under conditions described in Table 9.

TABLE 9

Test conditions used in the cellulase treatments.
Process parameter

| | |
|---|---|
| Denim load | 1.3 kg |
| Water | 19 l |
| Buffer/pH control (pH 6.5) | 31.6 g $Na_2HPO_4 \cdot H_2O$ |
| | 10.5 g Citric acid |
| Time | 55 min |
| Temperature | 60° C. |
| Cellulase dosage | 250-3000 NCU/g fabric |

Enzymes were dosed as neutral cellulase activity units (NCU) per the weight of the fabric. The cellulase enzyme was inactivated after draining by raising the pH above 11 by adding 5 g of NaOH (10 min, 40° C.) and rinsing three times. The jeans were dried in a tumbler. Two pairs of jeans were used in each test.

The biostoning effect/abrasion level was evaluated by measuring the color as reflectance values with Minolta CM 2500 or CM 1000 spectrophotometer using L*a*b* color space coordinates (illuminant D65/2°). The color from the face side and the reverse side of denim (data not shown) was measured after desizing (i.e. before the cellulase treatment) and after the cellulase treatment. Each measurement was the average of approximately 40 measurements. Two pairs of jeans were used in each test and the final result is the average of them. Lightness or increase of lightness after enzyme treatment was used for evaluation of abrasion effect (performance or biostoning effect). The results are shown in Tables 10 and 11, where bolding is used to highlight the similar abrasion levels and equivalent dosages. Treatments with 20K or without any enzyme were used for comparison. Some of preparations (Table 11) had been heat treated (pH 6.0, 65° C., 60 to 70 min) in order to inactivate any remaining *T. reesei* endogenous enzyme activity and/or in order to test the effect of heat treatment on the stability of the enzyme.

TABLE 10

Color measurements of the face side of denim treated with 20K + CBD fusion proteins

| Strain No. | Enzyme | NCU/g fabric | Before cellulase treatment L* | b* | After cellulase treatment L* | b* | Increase of L* |
|---|---|---|---|---|---|---|---|
| — | No enzyme | 0 | 16.77 | −9.95 | 18.18 | −12.39 | 1.42 |
| — | 20K[1] | 3000 | 16.80 | −9.70 | 24.00 | −14.71 | 7.20 |
| — | 20K[1] | 1500 | 16.73 | −10.05 | 22.98 | −14.62 | 6.25 |
| RF6036 | 20K + CBD | 500 | 16.41 | −10.14 | 22.80 | −14.19 | 6.40 |
| RF5977 | 20K + CBD | 250 | 16.68 | −9.91 | 22.81 | −14.47 | 6.13 |
| RF5977 | 20K + CBD | 500 | 16.73 | −10.01 | 24.07 | −14.70 | 7.34 |
| RF5977 | 20K + CBD | 1500 | 16.71 | −9.68 | 25.63 | −14.79 | 8.93 |

L* indicates the lightness,
−b* is the blue direction,
+b* is the yellow direction.
[1]Commercial preparation

TABLE 11

Color measurements of the face side of denim treated with heat treated 20K + CBD fusion proteins

| Strain No. | Enzyme | NCU/g fabric | Before cellulase treatment L* | b* | After cellulase treatment L* | B* | Increase of L* |
|---|---|---|---|---|---|---|---|
| — | No enzyme | 0 | 16.77 | −9.95 | 18.18 | −12.39 | 1.42 |
| — | 20K[1] (not heat treated) | 3000 | 16.80 | −9.70 | 24.00 | −14.71 | 7.20 |
| — | 20K[1] (not heat treated) | 1500 | 16.73 | −10.05 | 22.98 | −14.62 | 6.25 |
| RF5206 | 20K CBHI- | 3000 | 16.80 | −10.00 | 22.61 | −14.59 | 5.81 |
| RF5582 | 20K + CBD construct #1, CBHI- | 3000 | 16.83 | −10.01 | 26.39 | −15.13 | 9.56 |
| RF5582 | 20K + CBD-construct #1, CBHI- | 1000 | 16.61 | −9.76 | 23.98 | −14.98 | 7.37 |
| RF5582 | 20K + CBD-construct #1, CBHI- | 500 | 16.70 | −9.93 | 22.75 | −14.75 | 6.05 |
| RF5583 | 20K + CBD-construct #2, CBHI- | 3000 | 16.73 | −9.98 | 24.78 | −14.95 | 8.05 |
| RF5583 | 20K + CBD-construct #2, CBHI- | 1000 | 16.92 | −9.92 | 22.73 | −14.57 | 5.81 |

TABLE 11-continued

Color measurements of the face side of denim treated with heat treated 20K + CBD fusion proteins

| Strain No. | Enzyme | NCU/g fabric | Before cellulase treatment | | After cellulase treatment | | Increase of L* |
|---|---|---|---|---|---|---|---|
| | | | L* | b* | L* | B* | |
| RF5583 | 20K + CBD-construct #2, CBHI- | 500 | 16.62 | −10.03 | 21.76 | −14.37 | 5.14 |
| RF5977 | 20K + CBD-construct #5,[2] | 500 | 16.56 | −9.77 | 23.00 | −14.55 | 6.45 |

Figure 16:
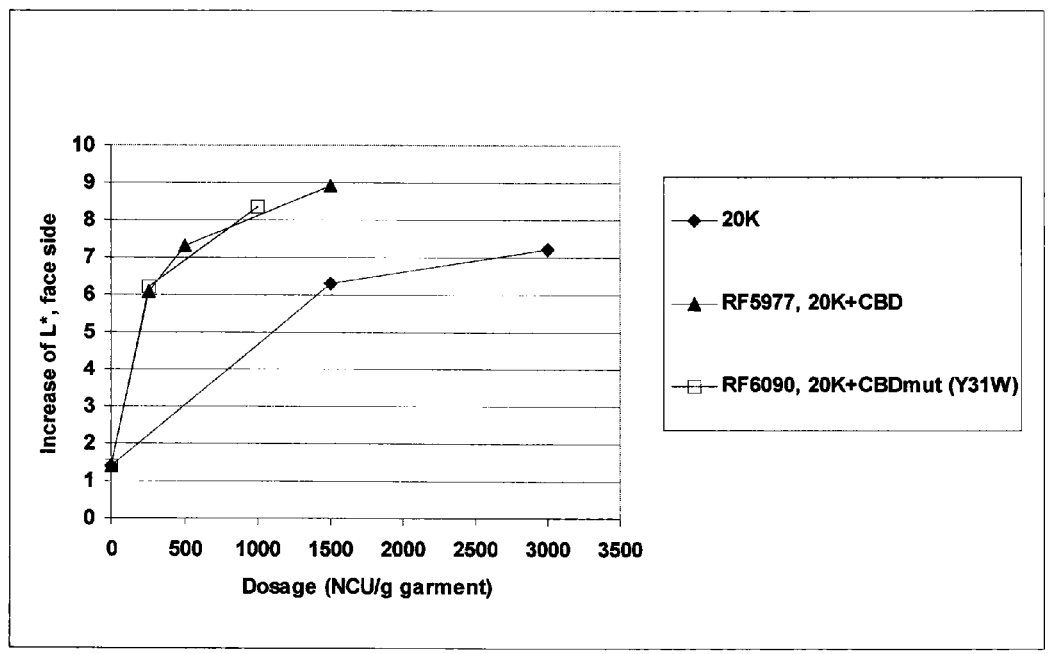
FIG. 16. The performance of strains RF5977 and RF6090 expressing fusion proteins of the invention compared to a commercial 20K preparation in denim treatment. Increase of lightness as a function of enzyme dosage at washing conditions described in Examples 8 and 9.

L* indicates the lightness.
−b* is the blue direction.
+b* is the yellow direction.
[1]Commercial preparation,
[2]CBHI-, CBHII-, EGI-, EGII- Results in Table 10 and FIG. 16 show that the washing performance of the 20K+CBD fusion proteins of the invention in denim treatment was greatly improved compared to 20K strains. With stain RF5977 the enzyme dosage as low as 250 NCU/g fabric could be used to obtain similar abrasion level (lightness L*) to that obtained with the 20K dosage of 1500 NCU/g. Thus a 6 times better washing performance was obtained, and the contrast was good. Also the washing performance obtained with strain RF5978 was similar to that obtained with RF5977.

Heat treatment of the fusion protein preparations seemed to somewhat decrease the stone washing effect, for instance with strain RF5977 a dosage of 500 NCU/g fabric was needed to obtain the same abrasion level as with dosage of 250 NCU/g of not heat treated enzyme preparation (Table 10). Nevertheless, a 3-fold improvement in the washing performance was achieved as compared to a prior art preparation.

Example 9

Performance of Fusion 20K+CBD Affinity Mutant Protein and Fusion 20K+CBD Linker Deletion Protein Preparations in Denim Finishing/Biostoning Fusion 20K+CBD affinity mutant enzymes produced using *Trichoderma* as host described in Example 3 and fusion 20K+ CBD linker deletion proteins produced using *Trichoderma* as host as described in Example 4 were tested for their ability in biostoning of denim. A 20K preparation efficient in denim finishing was used for comparison.

The denim and test systems for biostoning were as in Example 8. Also the effect of the cellulase treatment was evaluated as in Example 8. The results of the biostoning test for exemplary fusion 20K+CBD affinity mutant protein and fusion 20K+CBD linker deletion protein preparations are shown in Table 12.

Strain RF6090 with the Y31W amino acid substitution showed excellent washing performance (ca. 6 times better than 20K) and good contrast. The efficiency of strain RF6090 compared to 20K can clearly be seen also in FIG. 16. The Strain RF6084 with Y31A amino acid substitution was ca. 1.5 times better than 20K. Fusion 20K+CBD$_{mut}$ proteins with a Y32A or Y31A_Y32A amino acid substitution had a lower biostoning effect than 20K. The washing performance of the 20K+CBD linker deletion proteins in denim treatment was greatly improved compared to 20K strain and good contrast was obtained. With strain RF6108 (ΔG-444) the washing performance was at least 6 times better than with 20K and with strain RF6110 (ΔG-460) ca. 3 times better.

TABLE 12

Color measurements of the face side of denim treated with 20K + CBD affinity mutant and fusion 20K + CBD linker deletion proteins

| Strain No. | Enzyme (amino acid substitution) | Activity/ g fabric | Before cellulase treatment | | After cellulose treatment | | Increase of L* |
|---|---|---|---|---|---|---|---|
| | | | L* | B* | L* | B* | |
| — | No enzyme | 0 | 16.77 | −9.95 | 18.18 | −12.39 | 1.42 |
| — | 20K[1] | 3000 | 16.80 | −9.70 | 24.00 | −14.71 | 7.20 |
| — | 20K[1] | 1500 | 16.73 | −10.05 | 22.98 | −14.62 | 6.25 |
| RF6086 | 20K + CBDmut(Y32A) | 1500 | 16.83 | −9.68 | 22.05 | −14.14 | 5.22 |
| RF6086 | 20K + CBDmut(Y32A) | 3000 | 16.68 | −9.76 | 23.30 | −14.40 | 6.62 |
| RF6084 | 20K + CBDmut(Y31A) | 1000 | 16.83 | −9.42 | 23.15 | −14.26 | 6.32 |
| RF6090 | 20K + CBDmut(Y31W) | 250 | 16.79 | −9.32 | 22.99 | −14.24 | 6.21 |
| RF6090 | 20K + CBDmut(Y31W) | 1000 | 16.77 | −9.22 | 25.10 | −14.74 | 8.33 |
| RF6094 | 20K + CBDmut(Y31A_Y32A) | 1500 | 16.78 | −9.30 | 21.66 | −14.02 | 4.89 |
| RF6094 | 20K + CBDmut(Y31A_Y32A) | 3000 | 16.71 | −9.36 | 22.27 | −14.14 | 5.56 |
| — | 20K[1] | 3000 | 16.80 | −9.70 | 24.00 | −14.71 | 7.20 |
| RF6108 | 20K + CBD(ΔG-444) | 250 | 16.65 | −9.59 | 23.62 | −13.97 | 6.97 |
| RF6110 | 20K + CBD(ΔG-460) | 1000 | 16.81 | −9.72 | 24.17 | −14.39 | 7.37 |

L* indicates the lightness.
−b* is the blue direction.
+b* is the yellow direction.
[1]Commercial preparation

Example 10

Effect of the 20K+CBD Fusion Proteins on the Strength of the Denim

Some of the jeans obtained from washing tests with 20K+CBD fusion proteins (Examples 8 and 9) that had similar abrasion level (L*-value ca. 23 or 24 after cellulase treatment) were selected for the strength measurements. The tear strength after treatment with 20K+CBD fusion proteins and control samples were measured by Elmendof method according to standard SFS-EN ISO 13937-1. The specimens were cut both in the warp and weft direction. The results are shown in Table 13.

The cellulase fusion proteins caused essentially same or lower strength loss as 20K, i.e., with some preparations the strength of the fabric remained even higher. The lowest strength loss both in warp and weft direction was obtained with strain RF6108 with linker deletion ΔG-444. Also affinity mutant RF6090 with Y31W amino acid substitution caused less strength loss than 20K. Strain RF5977 had rather similar effect on the strength of the fabric than 20K.

Some of the jeans washed with heat treated fusion protein preparations (Example 8, Table 11) were also selected for tear strength measurements. It was noticed that the strength of the fabric was improved with some heat treated preparations, but because of the reduced washing performance higher dosages had to be used to obtain the same abrasion level.

The effect of the cellulase treatment was evaluated as in Example 8, except 20 color measurements were measured per leg.

Two legs with similar abrasion level (L*-value ca. 26 after cellulase treatment) from each washing test were selected for the strength measurements. The tear strength after treatment with 20K+CBD fusion proteins and control samples were measured as in Example 10. The results are shown in Table 14 and FIGS. 17A and 17B.

The tear strength of weft, which is typically weaker yarn than warp, was higher with fusion proteins of strains RF5977, RF6090, RF6108 and RF6110 than with 20K. With all of the fusion protein strains considerable higher strength both in warp and weft direction was obtained compared to DeniMax 399S and Mex 500. Also 20K strain was less harmful to the strength of the fabric than the other prior art preparations.

TABLE 13

Tear strength measurements of jeans treated with 20K + CBD fusion proteins of the invention

| Strain No. | Enzyme protein | NCU/ g fabric | L* | Warp Tear strenght (N) | (%) | Weft Tear strenght (N) | (%) |
|---|---|---|---|---|---|---|---|
| — | No enzyme | 0 | 1.5 | 62.2 | 100.0 | 46.2 | 100.0 |
| — | 20K[1] | 1500 | 22.9 | 46.3 | 74.4 | 31.9 | 69.0 |
| RF5977 | 20K + CBD | 250 | 22.9 | 48.1 | 77.3 | 32.1 | 69.5 |
| RF6086 | 20K + CBDmut (Y32A) | 3000 | 23.1 | 46.6 | 74.9 | 30 | 64.9 |
| RF6084 | 20K + CBDmut (Y31A) | 1000 | 23.1 | 47.2 | 75.9 | 30.6 | 66.2 |
| RF6090 | 20K + CBDmut (Y31W) | 250 | 23.2 | 48.6 | 78.1 | 34.4 | 74.5 |
| RF6094 | 20K + CBDmut (Y31A_Y32A) | 3000 | 22.3 | 48.4 | 77.8 | 32.9 | 71.2 |
| — | 20K[1] | 3000 | 23.9 | 47.6 | 76.5 | 28.9 | 62.6 |
| RF6108 | 20K + CBD (ΔG-444) | 250 | 23.8 | 54.3 | 87.3 | 35.2 | 76.2 |
| RF6110 | 20K + CBD (ΔG-460) | 1000 | 24.0 | 48.4 | 77.8 | 29.8 | 64.5 |

[1]Commercial preparation

Example 11

Comparison of Selected 20K+CBD Fusion Protein Preparations with Prior Art Enzyme Preparations Best 20K+CBD fusion proteins from Examples 8 and 9 were tested with other type of denim. 20K preparation (Ecostone® NP8500) efficient in denim finishing and two commercially available prior art preparations, DeniMax® 399S from Novozymes and Mex 500 from Meiji, which is the most concentrated solid enzyme preparation commercially available, were used for comparison.

The test system for biostoning was as in Example 8, except the denim load was 1 kg and the liquor ratio therefore slightly higher. Five pieces of denim ("legs") made of Down Under Denim twill (Bradmill Textiles Pty, Australia) were used for each test after desizing. Warp and weft yarns of the fabric were ring spun. Enzymes were dosed as NCU-activity units, so that similar abrasion levels (measured as lightness of the face side of denim after cellulase treatment) were obtained.

TABLE 14

Tear strength measurements of denim treated with 20K + CBD fusion proteins of the invention, 20K and prior art preparations

| Enzyme | Form | L* | Warp Tear strength (N) | Weft Tear strength (N) |
|---|---|---|---|---|
| Ecostone NP8500 | powder | 25.9 | 58.0 | 40.3 |
| RF5977, 20K + CBD | granula | 26.0 | 56.1 | 44.4 |

TABLE 14-continued

Tear strength measurements of denim treated with 20K + CBD fusion proteins of the invention, 20K and prior art preparations

| Enzyme | Form | L* | Warp Tear strength (N) | Weft Tear strength (N) |
|---|---|---|---|---|
| Mex 500, Meiji | powder | 26.1 | 48.4 | 31.1 |
| DeniMax 399S, Novozymes | granula | 25.5 | 50.6 | 38.1 |
| RF6090, 20K + CBD$_{mut}$ (Y31W) | liquid | 26.0 | 57.9 | 43.4 |
| RF6108, 20K + CBD (ΔG-444) | liquid | 25.9 | 55.6 | 43.9 |
| RF6110, 20K + CBD (ΔG-460) | liquid | 26.2 | 59.8 | 45.4 |

L* indicates the lightness of the face side of denim after cellulase treatment

REFERENCES

Aho S, V Olkkonen, T Jalava, M Paloheimo, R Bühler, M-L Niku-Paavola, E H Bamford and M Korhola. 1991. Monoclonal antibodies against core and cellulose-binding domains of *Trichoderma reesei* cellobiohydrolases I and II and endoglucanase I. Eur. J. Biochem. 200:643-649.

Azevedo Mde O, Felipe M S, Astolfi-Filho S, Radford A. 1990. Cloning, sequencing and homologies of the cbh-1 (exoglucanase) gene of *Humicola grisea* var. *thermoidea*. J Gen Microbiol. 136: 2569-2576.

Bailey M J and Nevalainen K M H. 1981. Induction, isolation and testing of stable *Trichoderma reesei* mutants with improved production of solubilizing cellulase. Enz Microbiol Technol. 3: 153-157.

Haakana H, Miettinen-Oinonen A, Joutsjoki V, Mäntylä A, Suominen P, and Vehmaanperä J. 2004. Cloning of cellulase genes from *Melanocarpus albomyces* and their efficient expression in *Trichoderma reesei*. Enz Microbiol Technol. 34: 159-167.

Henrissat B. (1991) A classification of glycosyl hydrolases based on amino acid sequence similarities. Biochem. J. 280: 309-316.

Henrissat B. and Bairoch A. (1993) New families in the classification of glycosyl hydrolases based on amino acid sequence similarities. Biochem. J. 293: 781-788.

Hong J, Tamaki H, Yamamoto K and Kumagai H. 2003. Cloning of a gene encoding thermostable cellobiohydrolase from *Thermoascus aurantiacus* and its expression in yeast. Appl Microbiol Biotechnol 63: 42-50.

Joutsjoki V V, Torkkeli T K, and Nevalainen K M H. 1993. Transformation of *Trichoderma reesei* with the *Hormoconis resinae* glucoamylase P (gamP) gene: production of a heterologous glucoamylase by *Trichoderma reesei*. Curr. Genet. 24:223-228.

Karhunen T, A Mäntylä, K M H Nevalainen, and P L Suominen. 1993. High frequency one-step gene replacement in *Trichoderma reesei*. I. Endoglucanase I overproduction. Mol. Gen. Genet. 241:515-522.

Laemmli U K. 1970. Cleavage of structural proteins during the assembly of the head of bacteriophage T4. Nature 227: 680-685.

Linder M, Mattinen M L, Kontteli M, Lindeberg G, Ståhlberg J, Drakenberg T, Reinikainen T, Pettersson G, Annila A. 1995. Identification of functionally important amino acids in the cellulose-binding domain of *Trichoderma reesei* cellobiohydrolase I. Protein Science 4: 1056-1064.

Lowry O H, N J Roseborough, A L Farr and R J Randall. 1951. Protein measurement with the Folin phenol reagent. J. Biol Chem 193: 265-275.

Malardier L, Daboussi M J, Julien J, Roussel F, Scazzocchio C and Brygoo Y. 1989. Cloning of the nitrate reductase gene (niaD) of *Aspergillus nidulans* and its use for transformation of *Fusarium oxysporum*. Gene 15:147-156.

Miettinen-Oinonen A, Londesborough J, Joutsjoki V, Lantto R and Vehmaanperä, J. 2004. Three cellulases from *Melanoarpus albomyces* with applications in the textile industry. Enz Microbiol Technol. 34: 332-341.

Penttilä M, H Nevalainen, M Rättö, E Salminen, and J Knowles. 1987. A versatile transformation system for the cellulolytic filamentous fungus *Trichoderma reesei*. Gene 61:155-164.

Saloheimo A, Henrissat B, Hoffren A M, Teleman O, Penttilä M. 1994. A novel, small endoglucanase gene, egl5, from *Trichoderma reesei* isolated by expression in yeast. Mol Microbiol 13: 219-228.

Sambrook J, E F Fritsch, and T Maniatis. 1989. Molecular cloning, a laboratory manual. Cold Spring Harbor Laboratory, New York, US.

Sambrook J and D W Russell. 2001. Molecular cloning, a laboratory manual. Cold Spring Harbor Laboratory, New York, US.

Srisodsuk M, Reinikainen T, Penttilä M, Teeri T T. 1993. Role of the interdomain linker peptide of *Trichoderma reesei* cellobiohydrolase I in its interaction with crystalline cellulose. J. Biol. Chem. 268: 20756-20761.

Van Tilbeurgh H, Loonties F, de Bruyne C, Clayssens M 1988. Fluorogenic and chromogenic glycosides as substrates and ligands of carbohydrases. Meth. Enzymol. 160: 45-59.

Ward M, Shan W, Dauberman J, Weiss G, Larenas E, Bower B, Rey M, Clarkson K and Bott R. (1993) Cloning, sequence and preliminary structural analysis of a small, high pI endoglucanase (EGIII) from *Trichoderma reesei*. Proceedings of the second TRICEL symposium on TRICHODERMA REESEI CELLULASES AND OTHER HYDROLASES, Espoo, Finland, 1993, ed. by P. Suominen and T. Reinikainen. Foundation for Biotechnical and Industrial Fermentation Research 8 (1993): 153-158.

The invention claimed is:

1. A cellulase fusion protein comprising:

first amino acid sequence, which is the 20 K cellulase of *Melanocarpus albomyces* of SEQ ID NO:2, or the 20K cellulase of *Melanocarpus albomyces* of SEQ ID NO:2 having at least one modification selected from the group consisting of: deletion of Ala at position 207, deletion of Val at position 208, substitution of Phe209Trp, and insertion of Pro after position 206, or a fragment thereof having cellulase activity, and a second amino acid sequence, which is the linker and cellulose binding domain (CBD) of *Trichoderma reesei* cellobiohydrolase I of SEQ ID NO:4, or the linker and cellulose biding domain (CBD) of *Trichoderma reesei* cellobiohydrolase I of SEQ ID NO: 4 having at least one modification selected from the group consisting of: substitution of tyrosine at position 492 (position 31 of the CBD), 493 (position 32 of the CBD) of the mature *T. reesei* CBHI with an aliphatic or aromatic amino acid, and deletions of amino acids 434 to 444 or 434 to 460 of the mature *T. reesei* CBHI sequence, or a fragment thereof having CBD activity, and a junction region having the following general formula:

$^1$A-$^2$B-$^3$Ile-$^4$D-$^5$Ser-$^6$F    (SEQ ID NO: 85)

wherein $^1$A is Gly or Val;

$^2$B is Pro, Gln, or Glu;

$^4$D is Gly or Pro; and $^6$F is Ser or is absent between said first amino acid sequence and said second amino acid sequence, whereby a stable fusion protein is obtained.

2. The cellulase fusion protein of claim 1, wherein the junction region has the following formula:

$^1$Val-$^2$Gln-$^3$Ile-$^4$Pro-$^5$Ser-$^6$Ser.    (SEQ ID NO: 52)

3. The cellulase fusion protein of claim 1, wherein the junction region has the following formula:

$^1$Gly-$^2$Glu-$^3$Ile-$^4$Gly-$^5$Ser    (SEQ ID NO: 53)

or $^1$Gly-$^2$Pro-$^3$Ile-$^4$Gly-$^5$Ser.    (SEQ ID NO: 54)

4. The cellulase fusion protein of claim 1, wherein said second amino acid sequence is set forth as SEQ ID NO:44.

5. The cellulase fusion protein of claim 1, wherein said first amino acid sequence is set forth as SEQ ID NO:39, said second amino acid sequence is set forth as SEQ ID NO:44, and said junction region has the formula: $^1$Val-$^2$Gln-$^3$Ile-$^4$Pro-$^5$Ser-$^6$Ser (SEQ ID NO: 52).

6. The cellulase fusion protein of claim 1, wherein in said second amino acid sequence at least one of said tyrosine at position 492 (position 31 of the CBD) and 493 (position 32 of the CBD) of the mature *T. reesei* CBHI is substituted with alanine or tryptophan.

7. The cellulase fusion protein of claim 1, wherein in said second amino acid sequence amino acids 434 to 444 or 434 to 460 of the mature *T reesei* CBHI sequence are deleted.

8. The cellulase fusion protein of claim 1, wherein in said first amino acid sequence valine at position 208 of the 20K cellulase sequence of *M albomyces* of SEQ ID. NO: 2 has been deleted.

9. The cellulase fusion protein of claim 1, wherein in said first amino acid sequence alanine at position 207 of the 20K cellulase sequence of *M albomyces* of SEQ ID. NO: 2 has been deleted.

10. The cellulase fusion protein of claim 1, wherein in said first amino acid sequence phenylalanine at position 209 of the 20 K cellulase sequence of *M albomyces* of SEQ ID. NO: 2 has been substituted with Trp.

11. The cellulase fusion protein of claim 1, wherein said first amino acid sequence contains an inserted proline after position 206 in the 20 K cellulase sequence of *M albomyces* of SEQ ID. NO: 2.

12. The cellulase fusion protein of claim 1, wherein said first amino acid sequence is SEQ ID. NO: 39.

13. An enzyme preparation comprising the cellulase fusion protein of claim 1.

14. A process for biostoning which comprises the step of adding the cellulase fusion protein of claim 1 to cotton containing fabric or garments.

15. The process of claim 14, wherein the fabric or garment is denim.

16. A process for biofinishing, which comprises the step of adding the cellulase fusion protein of claim 1 to a textile material.

17. The process of claim 16, wherein the textile material is manufactured of natural cellulose containing fibers or man-made cellulose containing fibers or a mixture thereof.

18. The process of claim 16, wherein the textile material is a blend of synthetic fibers and cellulose containing fibers.

19. A detergent composition comprising the fusion protein of claim 1 and one or more auxiliaries.

20. A method of treating cellulosic fiber containing textile material, wherein said method comprises contacting said textile material with the detergent composition of claim 19.

21. A method for treating wood-derived pulp or fiber, which comprises the step of adding the cellulase fusion protein of claim 1 to wood-derived mechanical or chemical pulp or secondary fiber.

22. A method for improving the quality of animal feed, which comprises treating plant material with the cellulase fusion protein of claim 1.

23. The process for biofinishing of claim 16, herein said textile material is fabric, garment or yarn.

24. The detergent composition of claim 19, wherein said auxiliaries are selected from the group consisting of surface active agents, surfactants, bleaching agents and builders.

* * * * *

SEQUENCE LISTING

```
<160> NUMBER OF SEQ ID NOS: 85

<210> SEQ ID NO 1
<211> LENGTH: 936
<212> TYPE: DNA
<213> ORGANISM: Melanocarpus albomyces

<400> SEQUENCE: 1 tcgccctaa  ccgagaacca  aagactccaa  gaatgcgctc  tactcccgtt  ctccgcgccc      60
tcctggccgc  agcattgccc  ctcggggccc  tcgccgccaa  cggtcagtcc  acgaggtaac    120
tgatcacccg  cctcattacg  cgtgccgacc  ggaccgcgtt  cagggctcac  tgctcaccgc    180
atccagatac  tgggactgct  gcaagccgtc  gtgcggctgg  gccggaaagg  gccccgtgaa    240
ccagcccgtc  tactcgtgcg  acgccaactt  ccagcgcatc  cacgacttcg  atgccgtctc    300
gggctgcgag  ggcggccccg  ccttctcgtg  cgccgaccac  agccctggg   ccattaatga    360 caacctctcg  tacggcttcg  cggcgactgc  actcagcggc  cagaccgagg  agtcgtggtg    420
ctgtgcctgc  tacgcgtgag  tgtgcttggg  cccaacgtcg  gtgattccgg  agttcagacc    480
```

```
actgacccag cgacccgctc gccagtctga cctttacatc gggtcccgtg gccggcaaga        540
ccatggtcgt ccagtcgacc agcacgggcg gcgacctcgg cagcaaccac ttcgacctca        600
acatccccgg cggcggcgtc ggcctcttcg acggctgcac tccccagttc ggcggcctcc        660
cgggcgcacg gtacggcggc atctcgtcgc gccaggagtg cgactcgttc cccgagccgc        720
tcaagcccgg ctgccagtgg cgcttcgact ggttccagaa cgccgacaac ccgtcctttta       780 ccttcgagcg ggtccagtgc cccgaggagc tggtcgctcg gaccggctgc aggcgccacg        840
acgacggcgg cttcgccgtc ttcaaggccc cagcgcctg atccgttttt gggcagtgtc         900
cgtgtgacgg cagctacgtg gaacgacctg gagctc                                   936

<210> SEQ ID NO 2
<211> LENGTH: 214
<212> TYPE: PRT
<213> ORGANISM: Melanocarpus albomyces

<400> SEQUENCE: 2

Ala Asn Gly Gln Ser Thr Arg Tyr Trp Asp Cys Cys Lys Pro Ser Cys
1               5                   10                  15

Gly Trp Ala Gly Lys Gly Pro Val Asn Gln Pro Val Tyr Ser Cys Asp
            20                  25                  30

Ala Asn Phe Gln Arg Ile His Asp Phe Asp Ala Val Ser Gly Cys Glu
        35                  40                  45

Gly Gly Pro Ala Phe Ser Cys Ala Asp His Ser Pro Trp Ala Ile Asn
    50                  55                  60

Asp Asn Leu Ser Tyr Gly Phe Ala Ala Thr Ala Leu Ser Gly Gln Thr
65                  70                  75                  80

Glu Glu Ser Trp Cys Cys Ala Cys Tyr Ala Leu Thr Phe Thr Ser Gly
                85                  90                  95

Pro Val Ala Gly Lys Thr Met Val Val Gln Ser Thr Ser Thr Gly Gly
            100                 105                 110

Asp Leu Gly Ser Asn His Phe Asp Leu Asn Ile Pro Gly Gly Gly Val
        115                 120                 125

Gly Leu Phe Asp Gly Cys Thr Pro Gln Phe Gly Gly Leu Pro Gly Ala
    130                 135                 140

Arg Tyr Gly Gly Ile Ser Ser Arg Gln Glu Cys Asp Ser Phe Pro Glu
145                 150                 155                 160

Pro Leu Lys Pro Gly Cys Gln Trp Arg Phe Asp Trp Phe Gln Asn Ala
                165                 170                 175

Asp Asn Pro Ser Phe Thr Phe Glu Arg Val Gln Cys Pro Glu Glu Leu
            180                 185                 190

Val Ala Arg Thr Gly Cys Arg Arg His Asp Asp Gly Gly Phe Ala Val
        195                 200                 205

Phe Lys Ala Pro Ser Ala
    210

<210> SEQ ID NO 3
<211> LENGTH: 1820
<212> TYPE: DNA
<213> ORGANISM: Trichoderma reesei

<400> SEQUENCE: 3
ccgcggactg cgcatcatgt atcggaagtt ggccgtcatc tcggccttct tggccacagc         60
tcgtgctcag tcggctgca ctctccaatc ggagactcac ccgcctctga catggcagaa        120
atgctcgtct ggtggcactt gcactcaaca gacaggctcc gtggtcatcg acgccaactg       180
```

```
gcgctggact cacgctacga acagcagcac gaactgctac gatggcaaca cttggagctc    240
gaccctatgt cctgacaacg agacctgcgc gaagaactgc tgtctggacg gtgccgccta    300
cgcgtccacg tacggagtta ccacgagcgg taacagcctc tccattggct ttgtcaccca    360
gtctgcgcag aagaacgttg cgctcgcct ttaccttatg ggcagcgaca cgacctacca     420
ggaattcacc ctgcttggca acgagttctc tttcgatgtt gatgtttcgc agctgccgta    480
agtgacttac catgaacccc tgacgtatct tcttgtgggc tcccagctga ctggccaatt    540
taaggtgcgg cttaacgga gctctctact tcgtgtccat ggacgcggat ggtggcgtga     600
gcaagtatcc caccaacacc gctggcgcca agtacggcac ggggtactgt gacagccagt    660
gtccccgcga tctgaagttc atcaatggcc aggccaacgt tgagggctgg agccgtcat     720 ccaacaacgc aaacacgggc attggaggac acggaagctg ctgctctgag atggatatct    780
gggaggccaa ctccatctcc gaggctctta cccccaccc ttgcacgact gtcggccagg     840
agatctgcga gggtgatggg tgcggcggaa cttactccga taacagatat ggcggcactt    900
gcgatcccga tggctgcgac tggaacccat accgcctggg caacaccagc ttctacggcc    960
ctggctcaag ctttaccctc gataccacca gaaaattgac cgttgtcacc cagtccgaga    1020
cgtcgggtgc catcaaccga tactatgtcc agaatggcgt cactttccag cagcccaacg    1080
ccgagcttgg tagttactct ggcaacgagc tcaacgatga ttactgcaca gctgaggagg    1140
cagaattcgg cggatcctct ttctcagaca agggcggcct gactcagttc aagaaggcta    1200
cctctggcgg catggttctg gtcatgagtc tgtgggatga tgtgagtttg atggacaaac    1260
atgcgcgttg acaaagagtc aagcagctga ctgagatgtt acagtactac gccaacatgc    1320
tgtggctgga ctccacctac ccgacaaacg agacctcctc cacacccggt gccgtgcgcg    1380
gaagctgctc caccagctcc ggtgtccctg ctcaggtcga atctcagtct cccaacgcca    1440
aggtcacctt ctccaacatc aagttcggac ccattggcag caccggcaac cctagcggcg    1500
gcaaccctcc cggcggaaac ccgcctggca ccaccaccac ccgccgccca gccactacca    1560
ctggaagctc tcccggacct acccagtctc actacggcca gtgcggcggt attggctaca    1620
gcggccccac ggtctgcgcc agcggcacaa cttgccaggt cctgaaccct tactactctc    1680
agtgcctgta aagctccgtg cgaaagcctg acgcaccggt agattcttgg tgagcccgta    1740
tcatgacggc ggcgggagct acatggcccc gggtgattta tttttttgt atctacttct     1800 gaccctttc aaatatacgg                                                1820
```

<210> SEQ ID NO 4
<211> LENGTH: 497
<212> TYPE: PRT
<213> ORGANISM: Trichoderma reesei

<400> SEQUENCE: 4

```
Gln Ser Ala Cys Thr Leu Gln Ser Glu Thr His Pro Pro Leu Thr Trp
  1               5                  10                  15

Gln Lys Cys Ser Ser Gly Gly Thr Cys Thr Gln Gln Thr Gly Ser Val
              20                  25                  30

Val Ile Asp Ala Asn Trp Arg Trp Thr His Ala Thr Asn Ser Ser Thr
          35                  40                  45

Asn Cys Tyr Asp Gly Asn Thr Trp Ser Ser Thr Leu Cys Pro Asp Asn
      50                  55                  60

Glu Thr Cys Ala Lys Asn Cys Cys Leu Asp Gly Ala Ala Tyr Ala Ser
 65                  70                  75                  80
```

```
Thr Tyr Gly Val Thr Thr Ser Gly Asn Ser Leu Ser Ile Gly Phe Val
            85                  90                  95

Thr Gln Ser Ala Gln Lys Asn Val Gly Ala Arg Leu Tyr Leu Met Gly
                100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
                195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Ser Glu Thr Ser Gly Ala Ile Asn Arg Tyr Tyr
290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
        355                 360                 365

Asp Tyr Tyr Ala Asn Met Leu Trp Leu Asp Ser Thr Tyr Pro Thr Asn
370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asn Pro
            420                 425                 430

Ser Gly Gly Asn Pro Pro Gly Gly Asn Pro Pro Gly Thr Thr Thr Thr
        435                 440                 445

Arg Arg Pro Ala Thr Thr Thr Gly Ser Ser Pro Gly Pro Thr Gln Ser
450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
                485                 490                 495

Leu
```

<210> SEQ ID NO 5
<211> LENGTH: 1895
<212> TYPE: DNA
<213> ORGANISM: Melanocarpus albomyces

<400> SEQUENCE: 5

```
gaattcgggg gttgccaggg agtcgtacag gggtgggtgg aggggatgg gggatggaag      60
ggggatggag aagaaagcat atatgggacg tttgtgctcg ccggctcccc tctgccacgt    120
tcccttgcct ccttgcctgg gttgttgttg gtcttccctt caccatccga caaaccaacc    180
tgctgcgggt gaactcgcag agcgccttcg gacgacgaca gacagacgca ccatgactcg    240
caacatcgcc ctgctcggcg ccgcgtcggc gctcctgggc ctcgcccacg ccagaagcc    300
gggcgagacg cccgaggtgc acccgcagct gacgacgttc cggtgcacca aggcggacgg    360
gtgccagccg cggaccaact acattgtgct ggactcgctg tcgcacccgg tgcaccaggt    420
ggacaacgac tacaactgcg cgactgggg gcagaagccc aacgcgacgg cgtgcccgga    480
cgtcgagtcg tgcgcgcgca actgcatcat ggagggcgtg cccgactaca gccagcacgg    540
cgtcacgacg agcgacacgt cgctgcgcct gcagcagctc gtcgacggcc gcctcgtcac    600
gccgcgcgtc tacctgctcg acgagaccga gcaccgctac gagatgatgc acctgaccgg    660
ccaggagttc acctttgagg tcgacgccac caagctgccc tgcggcatga acagcgccct    720
ctacctgtcc gagatggacc cgaccggcgc ccggagcgag ctcaaccccg gcggtgccta    780
ctacggcacc ggctactgcg acgcccagtg cttcgtgacg ccattcatca acggcattgt    840
gagtgttccc ctttggcccc ccccctgaaa atagatgtac ctgggtgcta accccggggt    900
gtcgcaccaa acagggcaa catcgagggc aagggctcgt gctgcaacga gatggacatc    960
tgggaggcca actcgcgggc gacgcacgtg gcgccgcaca cgtgcaacca gacgggtctg   1020
tacatgtgcg agggcgccga gtgcgagtac gacggcgtgt gcgacaagga cgggtgcggg   1080
tggaacccgt accgggtcaa catcaccgac tactacggca actcggacgc gttccgcgtc   1140
gacacgcggc ggccccttcac cgtggtgacg cagttcccgg ccgacgccga gggccggctc   1200
gagagcatcc accggctgta cgtgcaggac ggcaaggtga tcgagtcgta cgtcgtcgac   1260
gcgccggggcc tgccccggac cgactcgctc aacgacgagt tctgcgccgc cacgggcgcc   1320
gcgcgctacc tcgacctcgg cggcaccgcg ggcatgggcg acgccatgac gcgcggcatg   1380
gtgctggcca tgagcatctg gtgggacgag tccggcttca tgaactggct cgacagcggc   1440
gaggccggcc cctgcctgcc cgacgagggc gaccccaaga acattgtcaa ggtcgagccc   1500
agccccgagg tcacctacag caacctgcgc tggggcgaga tcgggtcgac ctttgaggcc   1560
gagtccgacg acgacggcga cggcgacgac tgctagataa ctaactagtg ggcggaaagg   1620
gcggggatg cgtaacttac atacagcccg gagttgtttt gagtgtagag tattgagctt   1680
tcgatgtgtt agttgagtgg aatgaaaat tcgcgtcttt gccccggtgg ttgcgataaa   1740
caatagtcgg ctggtgcatt tgtgacactt caattgcgct gttggcttgg tgacagacac   1800
ggcagcgtcg atgacccgac acccagaata attcgcatgg ttgattattg ttattgtgct   1860
ttaaatcgga ggctgatgct catctcttcg aattc                             1895
```

<210> SEQ ID NO 6
<211> LENGTH: 408
<212> TYPE: PRT
<213> ORGANISM: Melanocarpus albomyces

<400> SEQUENCE: 6

```
Gln Lys Pro Gly Glu Thr Pro Glu Val His Pro Gln Leu Thr Thr Phe
1               5                   10                  15

Arg Cys Thr Lys Ala Asp Gly Cys Gln Pro Arg Thr Asn Tyr Ile Val
            20                  25                  30

Leu Asp Ser Leu Ser His Pro Val His Gln Val Asp Asn Asp Tyr Asn
                35                  40                  45

Cys Gly Asp Trp Gly Gln Lys Pro Asn Ala Thr Ala Cys Pro Asp Val
50                  55                  60

Glu Ser Cys Ala Arg Asn Cys Ile Met Glu Gly Val Pro Asp Tyr Ser
65                  70                  75                  80

Gln His Gly Val Thr Thr Ser Asp Thr Ser Leu Arg Leu Gln Gln Leu
                85                  90                  95

Val Asp Gly Arg Leu Val Thr Pro Arg Val Tyr Leu Leu Asp Glu Thr
                100                 105                 110

Glu His Arg Tyr Glu Met Met His Leu Thr Gly Gln Glu Phe Thr Phe
                115                 120                 125

Glu Val Asp Ala Thr Lys Leu Pro Cys Gly Met Asn Ser Ala Leu Tyr
                130                 135                 140

Leu Ser Glu Met Asp Pro Thr Gly Ala Arg Ser Glu Leu Asn Pro Gly
145                 150                 155                 160

Gly Ala Tyr Tyr Gly Thr Gly Tyr Cys Asp Ala Gln Cys Phe Val Thr
                165                 170                 175

Pro Phe Ile Asn Gly Ile Gly Asn Ile Glu Gly Lys Gly Ser Cys Cys
                180                 185                 190

Asn Glu Met Asp Ile Trp Glu Ala Asn Ser Arg Ala Thr His Val Ala
                195                 200                 205

Pro His Thr Cys Asn Gln Thr Gly Leu Tyr Met Cys Glu Gly Ala Glu
210                 215                 220

Cys Glu Tyr Asp Gly Val Cys Asp Lys Asp Gly Cys Gly Trp Asn Pro
225                 230                 235                 240

Tyr Arg Val Asn Ile Thr Asp Tyr Tyr Gly Asn Ser Asp Ala Phe Arg
                245                 250                 255

Val Asp Thr Arg Arg Pro Phe Thr Val Val Thr Gln Phe Pro Ala Asp
                260                 265                 270

Ala Glu Gly Arg Leu Glu Ser Ile His Arg Leu Tyr Val Gln Asp Gly
                275                 280                 285

Lys Val Ile Glu Ser Tyr Val Val Asp Ala Pro Gly Leu Pro Arg Thr
290                 295                 300

Asp Ser Leu Asn Asp Glu Phe Cys Ala Ala Thr Gly Ala Ala Arg Tyr
305                 310                 315                 320

Leu Asp Leu Gly Gly Thr Ala Gly Met Gly Asp Ala Met Thr Arg Gly
                325                 330                 335

Met Val Leu Ala Met Ser Ile Trp Trp Asp Glu Ser Gly Phe Met Asn
                340                 345                 350

Trp Leu Asp Ser Gly Glu Ala Gly Pro Cys Leu Pro Asp Glu Gly Asp
                355                 360                 365

Pro Lys Asn Ile Val Lys Val Glu Pro Ser Pro Glu Val Thr Tyr Ser
                370                 375                 380

Asn Leu Arg Trp Gly Glu Ile Gly Ser Thr Phe Glu Ala Glu Ser Asp
385                 390                 395                 400

Asp Asp Gly Asp Gly Asp Asp Cys
                405
```

<210> SEQ ID NO 7

<211> LENGTH: 2100
<212> TYPE: DNA
<213> ORGANISM: Melanocarpus albomyces

<400> SEQUENCE: 7

```
cccggtctgg agacggggag cgcgccagcg acgcaggata agaaggcgac gaccgcgcct      60
ccgagccagg cccaggacag caggagaact cgccacgcgc aagcagcacg cccgatcgac     120
agtgtcccgc tctgcccaca gcactctgca accatgatga tgaagcagta cctccagtac     180
ctcgcggccg cgctgccgct cgtcggcctc gccgccggcc agcgcgctgg taacgagacg     240
cccgagaacc accccccgct cacctggcag aggtgcacgg ccccgggcaa ctgccagacc     300
gtgaacgccg aggtcgtcat tgacgccaac tggcgctggc tgcacgacga caacatgcag     360
aactgctacg acggcaacca gtggaccaac gcctgcagca ccgccaccga ctgcgctgag     420
aagtgcatga tcgagggtgc cggcgactac ctgggcacct acggcgcctc gaccagcggc     480
gacgccctga cgctcaagtt cgtcaccaag acgagtacg  gcaccaacgt cggctcgcgc     540
ttctacctca tgaacggccc ggacaagtac cagatgttca acctcatggg caacgagctt     600
gcctttgacg tcgacctctc gaccgtcgag tgcggcatca cagcgccct  gtacttcgtc     660
gccatggagg aggacggcgg catggccagc tacccgagca accaggccgg cgcccggtac     720
ggcactgggt tgagttgagc tccgctttgt ttcgagtcgc aacgaggcac tttctgggcg     780
ccggctaact ctctcgattc ctccgacagt actgcgatgc caatgcgct  cgtgatctca     840
agttcgttgg cggcaaggcc aacattgagg gctggaagtc gtccaccagc gaccccaacg     900
ctggcgtcgg cccgtacggc agctgctgcg ctgagatcga cgtctggtga gtgcgagacc     960
gtccacccag gttcggatgc ggggtggaaa tttcgcggct aacggagcac ccccagggga    1020
gtcgaatgcc tatgccttcg ctttcacgcc gcacgcgtgc acgaccaacg agtaccacgt    1080
ctgcgagacc accaactgcg gtggcaccta ctcggaggac cgcttcgccg gcaagtgcga    1140
cgccaacggc tgcgactaca accctaccg  catgggcaac cccgacttct acggcaaggg    1200
caagacgctc gacaccagcc gcaagttcac gtgcgtgacc ccttgtggcg caacctttct    1260
ctgcctgcct ggacacactg aaactgacac gtcgttttcg gctgcagcgt cgtctcccgc    1320
ttcgaggaga acaagctctc ccagtacttc atccaggacg gccgcaagat cgagatcccg    1380
ccgccgacgt gggagggcat gcccaacagc agcgagatca ccccgagct  ctgctccacc    1440
atgttcgatg tgttcaacga ccgcaaccgc ttcgaggagg tcggcggctt cgagcagctg    1500
aacaacgccc tccgggttcc catggtcctc gtcatgtcca tctgggacga cgtaagtacc    1560
cgccgacctc cctagccaca caagccgcat ccggcgaggc acgccatcgc tgctgctaac    1620
acgagaccgt tcgtagcact acgccaacat gctctggctc gactccatct acccgccgga    1680
gaaggagggc cagcccggcg ccgcccgtgg cgactgcccc acggactcgg tgtccccgc     1740
cgaggtcgag gctcagttcc ccgacgcgta agacttgccc ccgacccaa  gcttccactt    1800
ctggatgccg aatgctaaca cgcgaaacag ccaggtcgtc tggtccaaca tccgcttcgg    1860
ccccatcggc tcgacctacg acttctaagc cggtccatgc actcgcagcc ctgggcccgt    1920
cacgcccgcc acctcccctc gcggaaactc tccgtgcgtc gcgggctcca aagcattttg    1980
gcctcaagtt ttttcgttc atgtttcagt tctttccgca tgtatcctaa gctccgatag    2040
caagagaaat tgccagtctg agtttgggaa acctgtgatc cacatcatgg acgcataatg    2100
```

<210> SEQ ID NO 8
<211> LENGTH: 430
<212> TYPE: PRT

<213> ORGANISM: Melanocarpus albomyces

<400> SEQUENCE: 8

```
Gln Arg Ala Gly Asn Glu Thr Pro Glu Asn His Pro Pro Leu Thr Trp
1               5                   10                  15

Gln Arg Cys Thr Ala Pro Gly Asn Cys Gln Thr Val Asn Ala Glu Val
            20                  25                  30

Val Ile Asp Ala Asn Trp Arg Trp Leu His Asp Asp Asn Met Gln Asn
        35                  40                  45

Cys Tyr Asp Gly Asn Gln Trp Thr Asn Ala Cys Ser Thr Ala Thr Asp
    50                  55                  60

Cys Ala Glu Lys Cys Met Ile Glu Gly Ala Gly Asp Tyr Leu Gly Thr
65                  70                  75                  80

Tyr Gly Ala Ser Thr Ser Gly Asp Ala Leu Thr Leu Lys Phe Val Thr
                85                  90                  95

Lys His Glu Tyr Gly Thr Asn Val Gly Ser Arg Phe Tyr Leu Met Asn
            100                 105                 110

Gly Pro Asp Lys Tyr Gln Met Phe Asn Leu Met Gly Asn Glu Leu Ala
        115                 120                 125

Phe Asp Val Asp Leu Ser Thr Val Glu Cys Gly Ile Asn Ser Ala Leu
130                 135                 140

Tyr Phe Val Ala Met Glu Glu Asp Gly Gly Met Ala Ser Tyr Pro Ser
145                 150                 155                 160

Asn Gln Ala Gly Ala Arg Tyr Gly Thr Gly Tyr Cys Asp Ala Gln Cys
                165                 170                 175

Ala Arg Asp Leu Lys Phe Val Gly Gly Lys Ala Asn Ile Glu Gly Trp
            180                 185                 190

Lys Ser Ser Thr Ser Asp Pro Asn Ala Gly Val Gly Pro Tyr Gly Ser
        195                 200                 205

Cys Cys Ala Glu Ile Asp Val Trp Glu Ser Asn Ala Tyr Ala Phe Ala
210                 215                 220

Phe Thr Pro His Ala Cys Thr Thr Asn Glu Tyr His Val Cys Glu Thr
225                 230                 235                 240

Thr Asn Cys Gly Gly Thr Tyr Ser Glu Asp Arg Phe Ala Gly Lys Cys
                245                 250                 255

Asp Ala Asn Gly Cys Asp Tyr Asn Pro Tyr Arg Met Gly Asn Pro Asp
            260                 265                 270

Phe Tyr Gly Lys Gly Lys Thr Leu Asp Thr Ser Arg Lys Phe Thr Val
        275                 280                 285

Val Ser Arg Phe Glu Glu Asn Lys Leu Ser Gln Tyr Phe Ile Gln Asp
290                 295                 300

Gly Arg Lys Ile Glu Ile Pro Pro Pro Thr Trp Glu Gly Met Pro Asn
305                 310                 315                 320

Ser Ser Glu Ile Thr Pro Glu Leu Cys Ser Thr Met Phe Asp Val Phe
                325                 330                 335

Asn Asp Arg Asn Arg Phe Glu Glu Val Gly Gly Phe Glu Gln Leu Asn
            340                 345                 350

Asn Ala Leu Arg Val Pro Met Val Leu Val Met Ser Ile Trp Asp Asp
        355                 360                 365

His Tyr Ala Asn Met Leu Trp Leu Asp Ser Ile Tyr Pro Pro Glu Lys
370                 375                 380

Glu Gly Gln Pro Gly Ala Ala Arg Gly Asp Cys Pro Thr Asp Ser Gly
385                 390                 395                 400

Val Pro Ala Glu Val Glu Ala Gln Phe Pro Asp Ala Gln Val Val Trp
```

```
                405                 410                 415
Ser Asn Ile Arg Phe Gly Pro Ile Gly Ser Thr Tyr Asp Phe
            420                 425                 430
```

<210> SEQ ID NO 9
<211> LENGTH: 3459
<212> TYPE: DNA
<213> ORGANISM: Thermoascus aurantiacus

<400> SEQUENCE: 9

```
gaattctaga cctttatcct ttcatccgac cagacttccc tttttgacct tggcgccctg      60
ttgactacct acctacctag gtagtaacgt cgtcgaccct cttgaatgat ccttgtcaca     120
ctgcaaacat ccgaaaacat acggcaaaag atgattgggc atggatgcag agacatcga     180
atgagggctt agaaggaaat gaaaacctgg gaccaggacg ctaggtacga tgaaatccgc     240
caatggtgaa actttaagtc gtgcctacag cacaggctct gtgaagattg cgctgttcag     300
acttaatctt ctcatcacag tccaagtctt tatgaaaagg aaaaagagag ggaagagcgc     360
tatttcgagc tgttggcctc atagggagac agtcgagcat accagcggta tcgacgttag     420
actcaaccaa gaataatgac gagaataaac acagaagtca accttgaact ggatagcagg     480
gttccagcag cagatagtta cttgcataaa acaactccc cgagggctct ctgcatacac     540
caggatgttc cggaattatt cactgctcgt ttccgacgtg cgtcagtga tccgtctcca     600
cagaactcta cctgggaata acccagggga ggaatctgca agtaagaact taataccaat     660
cccccggggct gccgaggtga atcgaatctc ccgcgggaaa ttaaacccat acgatgtttt     720
tgcaccacat gcatgcttag cacgatttct ccgcaaggga gtcacagaga aagacatatt     780
tcgcatacta ctgtgactct gcagagttac atatcactca ggatacattg cagatcattg     840
tccgggcatc aaaaatggac ctgcaggatc aacggcccga caaaacacaa gtggctaaag     900
ctggggatg cccgaaaccc tctggtgcaa tatcatttga tggatgttcc ccccgcattt     960
ctaagacatc gacggatcgg cccgcatact aatccttta tcaaccaaaa gttccactcg    1020
actagagaaa aaaaaggcca aggcactag ttgcagtcgg atactggtct tttcgccgtc    1080
caacaccttc atccatgatc cccttagcca ccaatgcccc acataataca tgttgacata    1140
ggtacgtagc tctgttatcc aatcggatcc gaacctcttt aacggacccc tcctacacac    1200
cttatcctaa cttcagaaga ctgttgccca ttggggattg aggaggtccg ggtcgcagga    1260
tgcgttctag gctaaattct cggccggtag ccatctcgaa tctctcgtga agccttcatc    1320
tgaacggttg gcggcccgtc aagccgatga ccatgggttc ctgatagagc ttgtgcctga    1380
ccggccttgg cggcatagac gagctgaaca catcaggtat gaacagatca gatataaagt    1440
cggattgagt cctagtacga agcaatccgc caccaccaaa tcaagcaacg agcgacacga    1500
ataacaatat caatcgaatc gcaatgtatc agcgcgctct tctcttctct ttcttcctcg    1560
ccgccgcccg cgcgcacgag gccggtaccg taaccgcaga gaatcaccct tccctgacct    1620
ggcagcaatg ctccagcggc ggtagttgta ccacgcagaa tggaaaagtc gttatcgatg    1680
cgaactggcg ttgggtccat accacctctg gatacaccaa ctgctacacg ggcaatacgt    1740
gggacaccag tatctgtccc gacgacgtga cctgcgctca gaattgtgcc ttggatggag    1800
cggattacag tggcacctat ggtgttacga ccagtggcaa cgccctgaga ctgaactttg    1860
tcacccaaag ctcagggaag aacattggct cgcgcctgta cctgctgcag gacgacacca    1920
cttatcagat cttcaagctg ctgggtcagg agtttacctt cgatgtcgac gtctccaatc    1980
tcccttgcgg gctgaacggc gccctctact ttgtggccat ggacgccgac ggcaatttgt    2040
```

```
ccaaataccc tggcaacaag gcaggcgcta agtatggcac tggttactgc gactctcagt      2100
gccctcggga tctcaagttc atcaacggtc aggtacgtca gaagtgataa ctagccagca      2160
gagcccatga atcattaact aacgctgtca aatacaggcc aacgttgaag ctggcagcc       2220 gtctgccaac gacccaaatg ccggcgttgg taaccacggt tcctcgtgcg ctgagatgga      2280
tgtctgggaa gccaacagca tctctactgc ggtgacgcct cacccatgcg acaccccgg       2340 ccagaccatg tgccagggag acgactgtgg tggaacctac tcctccactc gatatgctgg      2400
tacctgcgac cctgatggct gcgacttcaa tccttaccag ccaggcaacc actcgttcta      2460
cggcccgggg aagatcgtcg acactagctc caaattcacc gtcgtcaccc agttcatcac      2520
cgacgacggg acaccctccg gcaccctgac ggagatcaaa cgcttctacg tccagaacgg      2580
caaggtgatc ccccagtcgg agtcgacgat cagcggcgtc accggcaact caatcaccac      2640
cgagtattgc acggcccaga aggcagcctt cggcgacaac accggcttct tcacgcacgg      2700
cgggcttcag aagatcagtc aggctctggc tcagggcatg gtcctcgtca tgagcctgtg      2760
ggacgatcac gccgccaaca tgctctggct ggacagcacc tacccgactg atgcggaccc      2820
ggacacccct ggcgtcgcgc gcggtacctg ccccacgacc tccggcgtcc cggccgacgt      2880
tgagtcgcag aaccccaatt catatgttat ctactccaac atcaaggtcg acccatcaa       2940 ctcgaccttc accgccaact aagtaagtaa cgggcactct accaccgaga gcttcgtgaa      3000
gatacagggg tagttgggag attgtcgtgt acagggaca tgcgatgctc aaaaatctac       3060
atcagtttgc caattgaacc atgaagaaaa ggggagatc aaagaagtct gtcagaagag       3120
aggggctgtg gcagcttaag ccttgttgta gatcgttcag agaaaaaaaa agtttgcgta     3180
cttattatat taggtcgatc attatccgat tgactccgtg acaagaatta aaagagtac       3240 tgcttgcttg cctatttaaa ttgttatata cgccgtagcg cttgcggacc acccctcaca      3300
gtatatcggt tcgcctcttc ttgtctcttc atctcacatc acaggtccag gtccagcccg      3360
gcccggtccg ggtgccatgc atgcacaggg ggactaatat attaatcgtg accctgtvcc      3420
taagctaggg tccctgcatt ttgaacctgt ggacgtctg                             3459
```

<210> SEQ ID NO 10
<211> LENGTH: 440
<212> TYPE: PRT
<213> ORGANISM: Thermoascus aurantiacus

<400> SEQUENCE: 10

```
Gln Gln Ala Gly Thr Val Thr Ala Glu Asn His Pro Ser Leu Thr Trp
1               5                   10                  15

Gln Gln Cys Ser Ser Gly Gly Ser Cys Thr Thr Gln Asn Gly Lys Val
            20                  25                  30

Val Ile Asp Ala Asn Trp Arg Trp Val His Thr Thr Ser Gly Tyr Thr
        35                  40                  45

Asn Cys Tyr Thr Gly Asn Thr Trp Asp Thr Ser Ile Cys Pro Asp Asp
    50                  55                  60

Val Thr Cys Ala Gln Asn Cys Ala Leu Asp Gly Ala Asp Tyr Ser Gly
65                  70                  75                  80

Thr Tyr Gly Val Thr Thr Ser Gly Asn Ala Leu Arg Leu Asn Phe Val
                85                  90                  95

Thr Gln Ser Ser Gly Lys Asn Ile Gly Ser Arg Leu Tyr Leu Leu Gln
            100                 105                 110

Asp Asp Thr Thr Tyr Gln Ile Phe Lys Leu Leu Gly Gln Glu Phe Thr
        115                 120                 125
```

```
Phe Asp Val Asp Val Ser Asn Leu Pro Cys Gly Leu Asn Gly Ala Leu
130                 135                 140

Tyr Phe Val Ala Met Asp Ala Asp Gly Gly Leu Ser Lys Tyr Pro Gly
145                 150                 155                 160

Asn Lys Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
                180                 185                 190

Gln Pro Ser Ala Asn Asp Pro Asn Ala Gly Val Gly Asn His Gly Ser
                195                 200                 205

Cys Cys Ala Glu Met Asp Val Trp Glu Ala Asn Ser Ile Ser Thr Ala
210                 215                 220

Val Thr Pro His Pro Cys Asp Thr Pro Gly Gln Thr Met Cys Gln Gly
225                 230                 235                 240

Asp Asp Cys Gly Gly Thr Tyr Ser Ser Thr Arg Tyr Ala Gly Thr Cys
                245                 250                 255

Asp Pro Asp Gly Cys Asp Phe Asn Pro Tyr Arg Gln Gly Asn His Ser
                260                 265                 270

Phe Tyr Gly Pro Gly Gln Ile Val Asp Thr Ser Ser Lys Phe Thr Val
                275                 280                 285

Val Thr Gln Phe Ile Thr Asp Asp Gly Thr Pro Ser Gly Thr Leu Thr
290                 295                 300

Glu Ile Lys Arg Phe Tyr Val Gln Asn Gly Lys Val Ile Pro Gln Ser
305                 310                 315                 320

Glu Ser Thr Ile Ser Gly Val Thr Gly Asn Ser Ile Thr Thr Glu Tyr
                325                 330                 335

Cys Thr Ala Gln Lys Ala Ala Phe Gly Asp Thr Gly Phe Phe Thr
                340                 345                 350

His Gly Gly Leu Gln Lys Ile Ser Gln Ala Leu Ala Gln Gly Met Val
                355                 360                 365

Leu Val Met Ser Leu Trp Asp Asp His Ala Ala Asn Met Leu Trp Leu
370                 375                 380

Asp Ser Thr Tyr Pro Thr Asp Ala Asp Pro Asp Thr Pro Gly Val Ala
385                 390                 395                 400

Arg Gly Thr Cys Pro Thr Thr Ser Gly Val Pro Ala Asp Val Glu Ser
                405                 410                 415

Gln Tyr Pro Asn Ser Tyr Val Ile Tyr Ser Asn Ile Lys Val Gly Pro
                420                 425                 430

Ile Asn Ser Thr Phe Thr Ala Asn
                435                 440

<210> SEQ ID NO 11
<211> LENGTH: 27
<212> TYPE: DNA
<213> ORGANISM: Artificial sequence
<220> FEATURE:
<223> OTHER INFORMATION: PCR primer

<400> SEQUENCE: 11
tacgccatgg tcgtccagtc gaccagc                                         27

<210> SEQ ID NO 12
<211> LENGTH: 35
<212> TYPE: DNA
<213> ORGANISM: Artificial sequence
<220> FEATURE:
<223> OTHER INFORMATION: PCR primer
```

```
<400> SEQUENCE: 12
tacgccatgg tcgtccagtc gaccagcacg ggcgg                              35

<210> SEQ ID NO 13
<211> LENGTH: 46
<212> TYPE: DNA
<213> ORGANISM: Artificial sequence
<220> FEATURE:
<223> OTHER INFORMATION: PCR primer

<400> SEQUENCE: 13
tacgccatgg tcgtccagtc gaccagcacg ggcggcgacc tcggca                 46

<210> SEQ ID NO 14
<211> LENGTH: 40
<212> TYPE: DNA
<213> ORGANISM: Artificial sequence
<220> FEATURE:
<223> OTHER INFORMATION: PCR primer

<400> SEQUENCE: 14
cgtactcgag tcatcgcgag ggggccttga agacggcgaa                        40

<210> SEQ ID NO 15
<211> LENGTH: 30
<212> TYPE: DNA
<213> ORGANISM: Artificial sequence
<220> FEATURE:
<223> OTHER INFORMATION: PCR primer

<400> SEQUENCE: 15
tgactcgaga ccggtgcgtc aggctttcgc                                   30

<210> SEQ ID NO 16
<211> LENGTH: 34
<212> TYPE: DNA
<213> ORGANISM: Artificial sequence
<220> FEATURE:
<223> OTHER INFORMATION: PCR primer

<400> SEQUENCE: 16
taggatccga gtcccattgg cagcaccggc aacc                              34

<210> SEQ ID NO 17
<211> LENGTH: 36
<212> TYPE: DNA
<213> ORGANISM: Artificial sequence
<220> FEATURE:
<223> OTHER INFORMATION: PCR primer

<400> SEQUENCE: 17
taggatccga gtcctagcgg cggcaaccct cccggc                            36

<210> SEQ ID NO 18
<211> LENGTH: 34
<212> TYPE: DNA
<213> ORGANISM: Artificial sequence
<220> FEATURE:
<223> OTHER INFORMATION: PCR primer

<400> SEQUENCE: 18
taggatccga gtcccattac cggcaaccct agcg                              34

<210> SEQ ID NO 19
<211> LENGTH: 55
```

```
<212> TYPE: DNA
<213> ORGANISM: Artificial sequence
<220> FEATURE:
<223> OTHER INFORMATION: PCR primer

<400> SEQUENCE: 19
cgtactcgag tcatcgcgag ccgatggggc cgaaggcgaa gccgccgtcg tcgtg        55

<210> SEQ ID NO 20
<211> LENGTH: 52
<212> TYPE: DNA
<213> ORGANISM: Artificial sequence
<220> FEATURE:
<223> OTHER INFORMATION: PCR primer

<400> SEQUENCE: 20
cgtactcgag tcatcgcgag ccgatctcgc cccagaagcc gccgtcgtcg tg           52

<210> SEQ ID NO 21
<211> LENGTH: 58
<212> TYPE: DNA
<213> ORGANISM: Artificial sequence
<220> FEATURE:
<223> OTHER INFORMATION: PCR primer

<400> SEQUENCE: 21
cgtactcgag tcatcgcgac gaggggatct ggacggcggg gaagccgccg tcgtcgtg     58

<210> SEQ ID NO 22
<211> LENGTH: 52
<212> TYPE: DNA
<213> ORGANISM: Artificial sequence
<220> FEATURE:
<223> OTHER INFORMATION: PCR primer

<400> SEQUENCE: 22
cgtactcgag tcatcgcgag ccgatctcgc cccaggcgaa gccgccgtcg tc           52

<210> SEQ ID NO 23
<211> LENGTH: 37
<212> TYPE: DNA
<213> ORGANISM: Artificial sequence
<220> FEATURE:
<223> OTHER INFORMATION: PCR primer

<400> SEQUENCE: 23
tcgtctcgag tcgcgatggg gccgaagcgg atgttgg                            37

<210> SEQ ID NO 24
<211> LENGTH: 31
<212> TYPE: DNA
<213> ORGANISM: Artificial sequence
<220> FEATURE:
<223> OTHER INFORMATION: PCR primer

<400> SEQUENCE: 24
ggagggcatg cccaacagca gcgagatcac c                                  31

<210> SEQ ID NO 25
<211> LENGTH: 38
<212> TYPE: DNA
<213> ORGANISM: Artificial sequence
<220> FEATURE:
<223> OTHER INFORMATION: PCR primer

<400> SEQUENCE: 25
cggcactagt tcgcgacccg atctcgcccc agcgcagg                           38
```

```
<210> SEQ ID NO 26
<211> LENGTH: 26
<212> TYPE: DNA
<213> ORGANISM: Artificial sequence
<220> FEATURE:
<223> OTHER INFORMATION: PCR primer

<400> SEQUENCE: 26
cgccgagggc cggctcgaga gcatcc                                            26

<210> SEQ ID NO 27
<211> LENGTH: 69
<212> TYPE: DNA
<213> ORGANISM: Artificial sequence
<220> FEATURE:
<223> OTHER INFORMATION: PCR primer

<400> SEQUENCE: 27
tgactcgaga ccggtgcgtc aggctttcgc acggagcttt acaggcactg agagtaggca       60
gggttcagg                                                               69

<210> SEQ ID NO 28
<211> LENGTH: 69
<212> TYPE: DNA
<213> ORGANISM: Artificial sequence
<220> FEATURE:
<223> OTHER INFORMATION: PCR primer

<400> SEQUENCE: 28
tgactcgaga ccggtgcgtc aggctttcgc acggagcttt acaggcactg agaggcgtaa       60
gggttcagg                                                               69

<210> SEQ ID NO 29
<211> LENGTH: 69
<212> TYPE: DNA
<213> ORGANISM: Artificial sequence
<220> FEATURE:
<223> OTHER INFORMATION: PCR primer

<400> SEQUENCE: 29
tgactcgaga ccggtgcgtc aggctttcgc acggagcttt acaggcactg agagtaccaa       60
gggttcagg                                                               69

<210> SEQ ID NO 30
<211> LENGTH: 69
<212> TYPE: DNA
<213> ORGANISM: Artificial sequence
<220> FEATURE:
<223> OTHER INFORMATION: PCR primer

<400> SEQUENCE: 30
tgactcgaga ccggtgcgtc aggctttcgc acggagcttt acaggcactg agaggcggca       60
gggttcagg                                                               69

<210> SEQ ID NO 31
<211> LENGTH: 57
<212> TYPE: DNA
<213> ORGANISM: Artificial sequence
<220> FEATURE:
<223> OTHER INFORMATION: PCR primer

<400> SEQUENCE: 31
taggatccga gtcccattac cggcaaccct agcaccacca ccacccgccg cccagcc          57
```

<210> SEQ ID NO 32
<211> LENGTH: 60
<212> TYPE: DNA
<213> ORGANISM: Artificial sequence
<220> FEATURE:
<223> OTHER INFORMATION: PCR primer

<400> SEQUENCE: 32
taggatccga gtcccattac cggcaaccct agccctaccc agtctcacta cggccagtgc    60

<210> SEQ ID NO 33
<211> LENGTH: 45
<212> TYPE: DNA
<213> ORGANISM: Artificial sequence
<220> FEATURE:
<223> OTHER INFORMATION: PCR primer

<400> SEQUENCE: 33
tgactcgaga ccggtgcgtc aggctttcgc acggagcttt acagg    45

<210> SEQ ID NO 34
<211> LENGTH: 67
<212> TYPE: DNA
<213> ORGANISM: Artificial sequence
<220> FEATURE:
<223> OTHER INFORMATION: PCR primer

<400> SEQUENCE: 34
ttaaacatat gttatctact ccaacatcaa ggtcggaccc attggcagca ccggcaaccc    60
tagcggc    67

<210> SEQ ID NO 35
<211> LENGTH: 50
<212> TYPE: DNA
<213> ORGANISM: Artificial sequence
<220> FEATURE:
<223> OTHER INFORMATION: PCR primer

<400> SEQUENCE: 35
tatatgcggc cgcaccggtg cgtcaggctt tcgcacggag ctttacaggc    50

<210> SEQ ID NO 36
<211> LENGTH: 34
<212> TYPE: DNA
<213> ORGANISM: Artificial sequence
<220> FEATURE:
<223> OTHER INFORMATION: PCR primer

<400> SEQUENCE: 36
ttggatccga gtcgcagcac cggcaaccct agcg    34

<210> SEQ ID NO 37
<211> LENGTH: 208
<212> TYPE: PRT
<213> ORGANISM: Melanocarpus albomyces

<400> SEQUENCE: 37

Ala Asn Gly Gln Ser Thr Arg Tyr Trp Asp Cys Cys Lys Pro Ser Cys
1               5                   10                  15

Gly Trp Ala Gly Lys Gly Pro Val Asn Gln Pro Val Tyr Ser Cys Asp
            20                  25                  30

Ala Asn Phe Gln Arg Ile His Asp Phe Asp Ala Val Ser Gly Cys Glu
        35                  40                  45

Gly Gly Pro Ala Phe Ser Cys Ala Asp His Ser Pro Trp Ala Ile Asn
            50                  55                  60

Asp Asn Leu Ser Tyr Gly Phe Ala Ala Thr Ala Leu Ser Gly Gln Thr
 65                  70                  75                  80

Glu Glu Ser Trp Cys Cys Ala Cys Tyr Ala Leu Thr Phe Thr Ser Gly
                 85                  90                  95

Pro Val Ala Gly Lys Thr Met Val Val Gln Ser Thr Ser Thr Gly Gly
            100                 105                 110

Asp Leu Gly Ser Asn His Phe Asp Leu Asn Ile Pro Gly Gly Gly Val
            115                 120                 125

Gly Leu Phe Asp Gly Cys Thr Pro Gln Phe Gly Gly Leu Pro Gly Ala
            130                 135                 140

Arg Tyr Gly Gly Ile Ser Ser Arg Gln Glu Cys Asp Ser Phe Pro Glu
145                 150                 155                 160

Pro Leu Lys Pro Gly Cys Gln Trp Arg Phe Asp Trp Phe Gln Asn Ala
                165                 170                 175

Asp Asn Pro Ser Phe Thr Phe Glu Arg Val Gln Cys Pro Glu Glu Leu
            180                 185                 190

Val Ala Arg Thr Gly Cys Arg Arg His Asp Asp Gly Gly Phe Ala Phe
            195                 200                 205

<210> SEQ ID NO 38
<211> LENGTH: 207
<212> TYPE: PRT
<213> ORGANISM: Melanocarpus albomyces

<400> SEQUENCE: 38

Ala Asn Gly Gln Ser Thr Arg Tyr Trp Asp Cys Cys Lys Pro Ser Cys
 1               5                  10                  15

Gly Trp Ala Gly Lys Gly Pro Val Asn Gln Pro Val Tyr Ser Cys Asp
             20                  25                  30

Ala Asn Phe Gln Arg Ile His Asp Phe Asp Ala Val Ser Gly Cys Glu
             35                  40                  45

Gly Gly Pro Ala Phe Ser Cys Ala Asp His Ser Pro Trp Ala Ile Asn
            50                  55                  60

Asp Asn Leu Ser Tyr Gly Phe Ala Ala Thr Ala Leu Ser Gly Gln Thr
 65                  70                  75                  80

Glu Glu Ser Trp Cys Cys Ala Cys Tyr Ala Leu Thr Phe Thr Ser Gly
                 85                  90                  95

Pro Val Ala Gly Lys Thr Met Val Val Gln Ser Thr Ser Thr Gly Gly
            100                 105                 110

Asp Leu Gly Ser Asn His Phe Asp Leu Asn Ile Pro Gly Gly Gly Val
            115                 120                 125

Gly Leu Phe Asp Gly Cys Thr Pro Gln Phe Gly Gly Leu Pro Gly Ala
            130                 135                 140

Arg Tyr Gly Gly Ile Ser Ser Arg Gln Glu Cys Asp Ser Phe Pro Glu
145                 150                 155                 160

Pro Leu Lys Pro Gly Cys Gln Trp Arg Phe Asp Trp Phe Gln Asn Ala
                165                 170                 175

Asp Asn Pro Ser Phe Thr Phe Glu Arg Val Gln Cys Pro Glu Glu Leu
            180                 185                 190

Val Ala Arg Thr Gly Cys Arg Arg His Asp Asp Gly Gly Phe Trp
            195                 200                 205

<210> SEQ ID NO 39
<211> LENGTH: 208

<212> TYPE: PRT
<213> ORGANISM: Melanocarpus albomyces

<400> SEQUENCE: 39

```
Ala Asn Gly Gln Ser Thr Arg Tyr Trp Asp Cys Cys Lys Pro Ser Cys
1               5                   10                  15

Gly Trp Ala Gly Lys Gly Pro Val Asn Gln Pro Val Tyr Ser Cys Asp
            20                  25                  30

Ala Asn Phe Gln Arg Ile His Asp Phe Asp Ala Val Ser Gly Cys Glu
        35                  40                  45

Gly Gly Pro Ala Phe Ser Cys Ala Asp His Ser Pro Trp Ala Ile Asn
    50                  55                  60

Asp Asn Leu Ser Tyr Gly Phe Ala Ala Thr Ala Leu Ser Gly Gln Thr
65                  70                  75                  80

Glu Glu Ser Trp Cys Cys Ala Cys Tyr Ala Leu Thr Phe Thr Ser Gly
                85                  90                  95

Pro Val Ala Gly Lys Thr Met Val Val Gln Ser Thr Ser Thr Gly Gly
            100                 105                 110

Asp Leu Gly Ser Asn His Phe Asp Leu Asn Ile Pro Gly Gly Gly Val
        115                 120                 125

Gly Leu Phe Asp Gly Cys Thr Pro Gln Phe Gly Gly Leu Pro Gly Ala
    130                 135                 140

Arg Tyr Gly Gly Ile Ser Ser Arg Gln Glu Cys Asp Ser Phe Pro Glu
145                 150                 155                 160

Pro Leu Lys Pro Gly Cys Gln Trp Arg Phe Asp Trp Phe Gln Asn Ala
                165                 170                 175

Asp Asn Pro Ser Phe Thr Phe Glu Arg Val Gln Cys Pro Glu Glu Leu
            180                 185                 190

Val Ala Arg Thr Gly Cys Arg Arg His Asp Asp Gly Phe Pro Ala
        195                 200                 205
```

<210> SEQ ID NO 40
<211> LENGTH: 208
<212> TYPE: PRT
<213> ORGANISM: Melanocarpus albomyces

<400> SEQUENCE: 40

```
Ala Asn Gly Gln Ser Thr Arg Tyr Trp Asp Cys Cys Lys Pro Ser Cys
1               5                   10                  15

Gly Trp Ala Gly Lys Gly Pro Val Asn Gln Pro Val Tyr Ser Cys Asp
            20                  25                  30

Ala Asn Phe Gln Arg Ile His Asp Phe Asp Ala Val Ser Gly Cys Glu
        35                  40                  45

Gly Gly Pro Ala Phe Ser Cys Ala Asp His Ser Pro Trp Ala Ile Asn
    50                  55                  60

Asp Asn Leu Ser Tyr Gly Phe Ala Ala Thr Ala Leu Ser Gly Gln Thr
65                  70                  75                  80

Glu Glu Ser Trp Cys Cys Ala Cys Tyr Ala Leu Thr Phe Thr Ser Gly
                85                  90                  95

Pro Val Ala Gly Lys Thr Met Val Val Gln Ser Thr Ser Thr Gly Gly
            100                 105                 110

Asp Leu Gly Ser Asn His Phe Asp Leu Asn Ile Pro Gly Gly Gly Val
        115                 120                 125

Gly Leu Phe Asp Gly Cys Thr Pro Gln Phe Gly Gly Leu Pro Gly Ala
    130                 135                 140

Arg Tyr Gly Gly Ile Ser Ser Arg Gln Glu Cys Asp Ser Phe Pro Glu
```

```
                   145                 150                 155                 160
Pro Leu Lys Pro Gly Cys Gln Trp Arg Phe Asp Trp Phe Gln Asn Ala
                165                 170                 175

Asp Asn Pro Ser Phe Thr Phe Glu Arg Val Gln Cys Pro Glu Glu Leu
                180                 185                 190

Val Ala Arg Thr Gly Cys Arg Arg His Asp Asp Gly Phe Ala Trp
                195                 200                 205

<210> SEQ ID NO 41
<211> LENGTH: 388
<212> TYPE: PRT
<213> ORGANISM: Melanocarpus albomyces

<400> SEQUENCE: 41

Gln Lys Pro Gly Glu Thr Pro Glu Val His Pro Gln Leu Thr Thr Phe
1               5                   10                  15

Arg Cys Thr Lys Ala Asp Gly Cys Gln Pro Arg Thr Asn Tyr Ile Val
                20                  25                  30

Leu Asp Ser Leu Ser His Pro Val His Gln Val Asp Asn Asp Tyr Asn
            35                  40                  45

Cys Gly Asp Trp Gly Gln Lys Pro Asn Ala Thr Ala Cys Pro Asp Val
50                  55                  60

Glu Ser Cys Ala Arg Asn Cys Ile Met Glu Gly Val Pro Asp Tyr Ser
65                  70                  75                  80

Gln His Gly Val Thr Thr Ser Asp Thr Ser Leu Arg Leu Gln Gln Leu
                85                  90                  95

Val Asp Gly Arg Leu Val Thr Pro Arg Val Tyr Leu Leu Asp Glu Thr
                100                 105                 110

Glu His Arg Tyr Glu Met Met His Leu Thr Gly Gln Glu Phe Thr Phe
            115                 120                 125

Glu Val Asp Ala Thr Lys Leu Pro Cys Gly Met Asn Ser Ala Leu Tyr
130                 135                 140

Leu Ser Glu Met Asp Pro Thr Gly Ala Arg Ser Glu Leu Asn Pro Gly
145                 150                 155                 160

Gly Ala Tyr Tyr Gly Thr Gly Tyr Cys Asp Ala Gln Cys Phe Val Thr
                165                 170                 175

Pro Phe Ile Asn Gly Ile Gly Asn Ile Glu Gly Lys Gly Ser Cys Cys
                180                 185                 190

Asn Glu Met Asp Ile Trp Glu Ala Asn Ser Arg Ala Thr His Val Ala
            195                 200                 205

Pro His Thr Cys Asn Gln Thr Gly Leu Tyr Met Cys Glu Gly Ala Glu
210                 215                 220

Cys Glu Tyr Asp Gly Val Cys Asp Lys Asp Gly Cys Gly Trp Asn Pro
225                 230                 235                 240

Tyr Arg Val Asn Ile Thr Asp Tyr Tyr Gly Asn Ser Asp Ala Phe Arg
                245                 250                 255

Val Asp Thr Arg Arg Pro Phe Thr Val Val Thr Gln Phe Pro Ala Asp
                260                 265                 270

Ala Glu Gly Arg Leu Glu Ser Ile His Arg Leu Tyr Val Gln Asp Gly
            275                 280                 285

Lys Val Ile Glu Ser Tyr Val Asp Ala Pro Gly Leu Pro Arg Thr
290                 295                 300

Asp Ser Leu Asn Asp Glu Phe Cys Ala Ala Thr Gly Ala Ala Arg Tyr
305                 310                 315                 320

Leu Asp Leu Gly Gly Thr Ala Gly Met Gly Asp Ala Met Thr Arg Gly
```

```
                    325                 330                 335
Met Val Leu Ala Met Ser Ile Trp Trp Asp Glu Ser Gly Phe Met Asn
                340                 345                 350

Trp Leu Asp Ser Gly Glu Ala Gly Pro Cys Leu Pro Asp Glu Gly Asp
            355                 360                 365

Pro Lys Asn Ile Val Lys Val Glu Pro Ser Pro Glu Val Thr Tyr Ser
        370                 375                 380

Asn Leu Arg Trp
385

<210> SEQ ID NO 42
<211> LENGTH: 421
<212> TYPE: PRT
<213> ORGANISM: Melanocarpus albomyces

<400> SEQUENCE: 42

Gln Arg Ala Gly Asn Glu Thr Pro Glu Asn His Pro Pro Leu Thr Trp
1               5                   10                  15

Gln Arg Cys Thr Ala Pro Gly Asn Cys Gln Thr Val Asn Ala Glu Val
            20                  25                  30

Val Ile Asp Ala Asn Trp Arg Trp Leu His Asp Asp Asn Met Gln Asn
        35                  40                  45

Cys Tyr Asp Gly Asn Gln Trp Thr Asn Ala Cys Ser Thr Ala Thr Asp
    50                  55                  60

Cys Ala Glu Lys Cys Met Ile Glu Gly Ala Gly Asp Tyr Leu Gly Thr
65                  70                  75                  80

Tyr Gly Ala Ser Thr Ser Gly Asp Ala Leu Thr Leu Lys Phe Val Thr
                85                  90                  95

Lys His Glu Tyr Gly Thr Asn Val Gly Ser Arg Phe Tyr Leu Met Asn
            100                 105                 110

Gly Pro Asp Lys Tyr Gln Met Phe Asn Leu Met Gly Asn Glu Leu Ala
        115                 120                 125

Phe Asp Val Asp Leu Ser Thr Val Glu Cys Gly Ile Asn Ser Ala Leu
    130                 135                 140

Tyr Phe Val Ala Met Glu Glu Asp Gly Gly Met Ala Ser Tyr Pro Ser
145                 150                 155                 160

Asn Gln Ala Gly Ala Arg Tyr Gly Thr Gly Tyr Cys Asp Ala Gln Cys
                165                 170                 175

Ala Arg Asp Leu Lys Phe Val Gly Gly Lys Ala Asn Ile Glu Gly Trp
            180                 185                 190

Lys Ser Ser Thr Ser Asp Pro Asn Ala Gly Val Gly Pro Tyr Gly Ser
        195                 200                 205

Cys Cys Ala Glu Ile Asp Val Trp Glu Ser Asn Ala Tyr Ala Phe Ala
    210                 215                 220

Phe Thr Pro His Ala Cys Thr Thr Asn Glu Tyr His Val Cys Glu Thr
225                 230                 235                 240

Thr Asn Cys Gly Gly Thr Tyr Ser Glu Asp Arg Phe Ala Gly Lys Cys
                245                 250                 255

Asp Ala Asn Gly Cys Asp Tyr Asn Pro Tyr Arg Met Gly Asn Pro Asp
            260                 265                 270

Phe Tyr Gly Lys Gly Lys Thr Leu Asp Thr Ser Arg Lys Phe Thr Val
        275                 280                 285

Val Ser Arg Phe Glu Glu Asn Lys Leu Ser Gln Tyr Phe Ile Gln Asp
    290                 295                 300

Gly Arg Lys Ile Glu Ile Pro Pro Pro Thr Trp Glu Gly Met Pro Asn
```

```
              305                 310                 315                 320
Ser Ser Glu Ile Thr Pro Glu Leu Cys Ser Thr Met Phe Asp Val Phe
                        325                 330                 335

Asn Asp Arg Asn Arg Phe Glu Glu Val Gly Gly Phe Glu Gln Leu Asn
                        340                 345                 350

Asn Ala Leu Arg Val Pro Met Val Leu Val Met Ser Ile Trp Asp Asp
                        355                 360                 365

His Tyr Ala Asn Met Leu Trp Leu Asp Ser Ile Tyr Pro Pro Glu Lys
                        370                 375                 380

Glu Gly Gln Pro Gly Ala Ala Arg Gly Asp Cys Pro Thr Asp Ser Gly
385                 390                 395                 400

Val Pro Ala Glu Val Glu Ala Gln Phe Pro Asp Ala Gln Val Val Trp
                        405                 410                 415

Ser Asn Ile Arg Phe
                420

<210> SEQ ID NO 43
<211> LENGTH: 430
<212> TYPE: PRT
<213> ORGANISM: Thermoascus aurantiacus

<400> SEQUENCE: 43

Gln Gln Ala Gly Thr Val Thr Ala Glu Asn His Pro Ser Leu Thr Trp
1               5                   10                  15

Gln Gln Cys Ser Ser Gly Gly Ser Cys Thr Thr Gln Asn Gly Lys Val
                20                  25                  30

Val Ile Asp Ala Asn Trp Arg Trp Val His Thr Thr Ser Gly Tyr Thr
            35                  40                  45

Asn Cys Tyr Thr Gly Asn Thr Trp Asp Thr Ser Ile Cys Pro Asp Asp
50                  55                  60

Val Thr Cys Ala Gln Asn Cys Ala Leu Asp Gly Ala Asp Tyr Ser Gly
65                  70                  75                  80

Thr Tyr Gly Val Thr Thr Ser Gly Asn Ala Leu Arg Leu Asn Phe Val
                85                  90                  95

Thr Gln Ser Ser Gly Lys Asn Ile Gly Ser Arg Leu Tyr Leu Leu Gln
                100                 105                 110

Asp Asp Thr Thr Tyr Gln Ile Phe Lys Leu Leu Gly Gln Glu Phe Thr
            115                 120                 125

Phe Asp Val Asp Val Ser Asn Leu Pro Cys Gly Leu Asn Gly Ala Leu
130                 135                 140

Tyr Phe Val Ala Met Asp Ala Asp Gly Gly Leu Ser Lys Tyr Pro Gly
145                 150                 155                 160

Asn Lys Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Gln Pro Ser Ala Asn Asp Pro Asn Ala Gly Val Gly Asn His Gly Ser
                195                 200                 205

Cys Cys Ala Glu Met Asp Val Trp Glu Ala Asn Ser Ile Ser Thr Ala
            210                 215                 220

Val Thr Pro His Pro Cys Asp Thr Pro Gly Gln Thr Met Cys Gln Gly
225                 230                 235                 240

Asp Asp Cys Gly Gly Thr Tyr Ser Ser Thr Arg Tyr Ala Gly Thr Cys
                245                 250                 255

Asp Pro Asp Gly Cys Asp Phe Asn Pro Tyr Arg Gln Gly Asn His Ser
```

```
                      260                 265                 270
        Phe Tyr Gly Pro Gly Gln Ile Val Asp Thr Ser Ser Lys Phe Thr Val
                275                 280                 285

Val Thr Gln Phe Ile Thr Asp Asp Gly Thr Pro Ser Gly Thr Leu Thr
            290                 295                 300

Glu Ile Lys Arg Phe Tyr Val Gln Asn Gly Lys Val Ile Pro Gln Ser
        305                 310                 315                 320

Glu Ser Thr Ile Ser Gly Val Thr Gly Asn Ser Ile Thr Thr Glu Tyr
                        325                 330                 335

Cys Thr Ala Gln Lys Ala Ala Phe Gly Asp Asn Thr Gly Phe Phe Thr
                        340                 345                 350

His Gly Gly Leu Gln Lys Ile Ser Gln Ala Leu Ala Gln Gly Met Val
                        355                 360                 365

Leu Val Met Ser Leu Trp Asp Asp His Ala Ala Asn Met Leu Trp Leu
                        370                 375                 380

Asp Ser Thr Tyr Pro Thr Asp Ala Asp Pro Asp Thr Pro Gly Val Ala
        385                 390                 395                 400

Arg Gly Thr Cys Pro Thr Thr Ser Gly Val Pro Ala Asp Val Glu Ser
                        405                 410                 415

Gln Tyr Pro Asn Ser Tyr Val Ile Tyr Ser Asn Ile Lys Val
                        420                 425                 430

<210> SEQ ID NO 44
<211> LENGTH: 69
<212> TYPE: PRT
<213> ORGANISM: Trichoderma reesei

<400> SEQUENCE: 44

Thr Gly Asn Pro Ser Gly Gly Asn Pro Gly Gly Asn Pro Gly
1               5                   10                  15

Thr Thr Thr Thr Arg Arg Pro Ala Thr Thr Thr Gly Ser Ser Pro Gly
            20                  25                  30

Pro Thr Gln Ser His Tyr Gly Gln Cys Gly Gly Ile Gly Tyr Ser Gly
        35                  40                  45

Pro Thr Val Cys Ala Ser Gly Thr Thr Cys Gln Val Leu Asn Pro Tyr
    50                  55                  60

Tyr Ser Gln Cys Leu
65

<210> SEQ ID NO 45
<211> LENGTH: 69
<212> TYPE: PRT
<213> ORGANISM: Trichoderma reesei

<400> SEQUENCE: 45

Thr Gly Asn Pro Ser Gly Gly Asn Pro Gly Gly Asn Pro Gly
1               5                   10                  15

Thr Thr Thr Thr Arg Arg Pro Ala Thr Thr Thr Gly Ser Ser Pro Gly
            20                  25                  30

Pro Thr Gln Ser His Tyr Gly Gln Cys Gly Gly Ile Gly Tyr Ser Gly
        35                  40                  45

Pro Thr Val Cys Ala Ser Gly Thr Thr Cys Gln Val Leu Asn Pro Ala
    50                  55                  60

Tyr Ser Gln Cys Leu
65

<210> SEQ ID NO 46
```

```
<211> LENGTH: 69
<212> TYPE: PRT
<213> ORGANISM: Trichoderma reesei

<400> SEQUENCE: 46

Thr Gly Asn Pro Ser Gly Gly Asn Pro Pro Gly Gly Asn Pro Pro Gly
 1               5                  10                  15

Thr Thr Thr Thr Arg Arg Pro Ala Thr Thr Thr Gly Ser Ser Pro Gly
             20                  25                  30

Pro Thr Gln Ser His Tyr Gly Gln Cys Gly Gly Ile Gly Tyr Ser Gly
         35                  40                  45

Pro Thr Val Cys Ala Ser Gly Thr Thr Cys Gln Val Leu Asn Pro Tyr
     50                  55                  60

Ala Ser Gln Cys Leu
 65

<210> SEQ ID NO 47
<211> LENGTH: 69
<212> TYPE: PRT
<213> ORGANISM: Trichoderma reesei

<400> SEQUENCE: 47

Thr Gly Asn Pro Ser Gly Gly Asn Pro Pro Gly Gly Asn Pro Pro Gly
 1               5                  10                  15

Thr Thr Thr Thr Arg Arg Pro Ala Thr Thr Thr Gly Ser Ser Pro Gly
             20                  25                  30

Pro Thr Gln Ser His Tyr Gly Gln Cys Gly Gly Ile Gly Tyr Ser Gly
         35                  40                  45

Pro Thr Val Cys Ala Ser Gly Thr Thr Cys Gln Val Leu Asn Pro Trp
     50                  55                  60

Tyr Ser Gln Cys Leu
 65

<210> SEQ ID NO 48
<211> LENGTH: 69
<212> TYPE: PRT
<213> ORGANISM: Trichoderma reesei

<400> SEQUENCE: 48

Thr Gly Asn Pro Ser Gly Gly Asn Pro Pro Gly Gly Asn Pro Pro Gly
 1               5                  10                  15

Thr Thr Thr Thr Arg Arg Pro Ala Thr Thr Thr Gly Ser Ser Pro Gly
             20                  25                  30

Pro Thr Gln Ser His Tyr Gly Gln Cys Gly Gly Ile Gly Tyr Ser Gly
         35                  40                  45

Pro Thr Val Cys Ala Ser Gly Thr Thr Cys Gln Val Leu Asn Pro Ala
     50                  55                  60

Ala Ser Gln Cys Leu
 65

<210> SEQ ID NO 49
<211> LENGTH: 58
<212> TYPE: PRT
<213> ORGANISM: Trichoderma reesei

<400> SEQUENCE: 49

Thr Gly Asn Pro Ser Thr Thr Thr Arg Arg Pro Ala Thr Thr Thr
 1               5                  10                  15

Gly Ser Ser Pro Gly Pro Thr Gln Ser His Tyr Gly Gln Cys Gly Gly
             20                  25                  30
```

```
Ile Gly Tyr Ser Gly Pro Thr Val Cys Ala Ser Gly Thr Thr Cys Gln
        35                  40                  45

Val Leu Asn Pro Tyr Tyr Ser Gln Cys Leu
     50                  55

<210> SEQ ID NO 50
<211> LENGTH: 42
<212> TYPE: PRT
<213> ORGANISM: Trichoderma reesei

<400> SEQUENCE: 50

Thr Gly Asn Pro Ser Pro Thr Gln Ser His Tyr Gly Gln Cys Gly Gly
1               5                   10                  15

Ile Gly Tyr Ser Gly Pro Thr Val Cys Ala Ser Gly Thr Thr Cys Gln
            20                  25                  30

Val Leu Asn Pro Tyr Tyr Ser Gln Cys Leu
        35                  40

<210> SEQ ID NO 51
<211> LENGTH: 6
<212> TYPE: PRT
<213> ORGANISM: Artificial Sequence
<220> FEATURE:
<223> OTHER INFORMATION: Junction Region generated by ligated plasmids
<220> FEATURE:
<221> NAME/KEY: misc_feature
<222> LOCATION: (2)..(2)
<223> OTHER INFORMATION: Xaa is Pro, Gln or Glu
<220> FEATURE:
<221> NAME/KEY: misc_feature
<222> LOCATION: (4)..(4)
<223> OTHER INFORMATION: Xaa is Gly or Pro
<220> FEATURE:
<221> NAME/KEY: misc_feature
<222> LOCATION: (6)..(6)
<223> OTHER INFORMATION: Xaa is Ser or no amino acid

<400> SEQUENCE: 51

Gly Xaa Ile Xaa Ser Xaa
1               5

<210> SEQ ID NO 52
<211> LENGTH: 6
<212> TYPE: PRT
<213> ORGANISM: Artificial Sequence
<220> FEATURE:
<223> OTHER INFORMATION: Junction Region generated by ligated plasmids

<400> SEQUENCE: 52

Val Gln Ile Pro Ser Ser
1               5

<210> SEQ ID NO 53
<211> LENGTH: 5
<212> TYPE: PRT
<213> ORGANISM: Artificial Sequence
<220> FEATURE:
<223> OTHER INFORMATION: Junction Region generated by ligated plasmids

<400> SEQUENCE: 53

Gly Glu Ile Gly Ser
1               5

<210> SEQ ID NO 54
<211> LENGTH: 5
<212> TYPE: PRT
<213> ORGANISM: Artificial Sequence
```

```
<220> FEATURE:
<223> OTHER INFORMATION: Junction Region generated by ligated plasmids

<400> SEQUENCE: 54

Gly Pro Ile Gly Ser
1               5

<210> SEQ ID NO 55
<211> LENGTH: 18
<212> TYPE: PRT
<213> ORGANISM: Artificial Sequence
<220> FEATURE:
<223> OTHER INFORMATION: Core-Linker Junction generated by ligated
      plasmids

<400> SEQUENCE: 55

His Asp Asp Gly Gly Phe Ala Val Phe Lys Ala Pro Ser Gly Ser Thr
1               5                   10                  15

Gly Asn

<210> SEQ ID NO 56
<211> LENGTH: 19
<212> TYPE: PRT
<213> ORGANISM: Artificial Sequence
<220> FEATURE:
<223> OTHER INFORMATION: Core-Linker Junction generated by ligated
      plasmids

<400> SEQUENCE: 56

His Asp Asp Gly Gly Phe Ala Val Phe Lys Ala Pro Ser Gly Gly Asn
1               5                   10                  15

Pro Pro Gly

<210> SEQ ID NO 57
<211> LENGTH: 16
<212> TYPE: PRT
<213> ORGANISM: Artificial Sequence
<220> FEATURE:
<223> OTHER INFORMATION: Core-Linker Junction generated by ligated
      plasmids

<400> SEQUENCE: 57

His Asp Asp Gly Gly Phe Ala Phe Gly Pro Ile Gly Ser Thr Gly Asn
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Core-Linker Junction generated by ligated
      plasmids

<400> SEQUENCE: 58

His Asp Asp Gly Gly Phe Trp Gly Glu Ile Gly Ser Thr Gly Asn
1               5                   10                  15

<210> SEQ ID NO 59
<211> LENGTH: 17
<212> TYPE: PRT
<213> ORGANISM: Artificial Sequence
<220> FEATURE:
<223> OTHER INFORMATION: Core-Linker Junction generated by ligated
      plasmids

<400> SEQUENCE: 59

His Asp Asp Gly Gly Phe Pro Ala Val Gln Ile Pro Ser Ser Thr Gly
```

```
1               5                   10                  15
Asn

<210> SEQ ID NO 60
<211> LENGTH: 16
<212> TYPE: PRT
<213> ORGANISM: Artificial Sequence
<220> FEATURE:
<223> OTHER INFORMATION: Core-Linker Junction generated by ligated
      plasmids

<400> SEQUENCE: 60

His Asp Asp Gly Gly Phe Ala Trp Gly Glu Ile Gly Ser Thr Gly Asn
1               5                   10                  15

<210> SEQ ID NO 61
<211> LENGTH: 18
<212> TYPE: PRT
<213> ORGANISM: Melanocarpus albomyces

<400> SEQUENCE: 61

Asp Gly Gly Phe Ala Val Phe Lys Ala Pro Ser Gly Ser Thr Gly Asn
1               5                   10                  15

Pro Ser

<210> SEQ ID NO 62
<211> LENGTH: 14
<212> TYPE: PRT
<213> ORGANISM: Melanocarpus albomyces

<400> SEQUENCE: 62

Asp Gly Gly Phe Ala Val Phe Lys Ala Pro Ser Gly Gly Asn
1               5                   10

<210> SEQ ID NO 63
<211> LENGTH: 6
<212> TYPE: PRT
<213> ORGANISM: Trichoderma reesei

<400> SEQUENCE: 63

Tyr Tyr Ser Gln Cys Leu
1               5

<210> SEQ ID NO 64
<211> LENGTH: 16
<212> TYPE: PRT
<213> ORGANISM: Melanocarpus Albomyces

<400> SEQUENCE: 64

Asp Gly Gly Phe Ala Phe Gly Pro Ile Gly Ser Thr Gly Asn Pro Ser
1               5                   10                  15

<210> SEQ ID NO 65
<211> LENGTH: 15
<212> TYPE: PRT
<213> ORGANISM: Melanocarpus albomyces

<400> SEQUENCE: 65

Asp Gly Gly Phe Trp Gly Glu Ile Gly Ser Thr Gly Asn Pro Ser
1               5                   10                  15

<210> SEQ ID NO 66
<211> LENGTH: 17
<212> TYPE: PRT
<213> ORGANISM: Melanocarpus albomyces
```

```
<400> SEQUENCE: 66

Asp Gly Gly Phe Pro Ala Val Gln Ile Pro Ser Ser Thr Gly Asn Pro
1               5                   10                  15

Ser

<210> SEQ ID NO 67
<211> LENGTH: 16
<212> TYPE: PRT
<213> ORGANISM: Melanocarpus albomyces

<400> SEQUENCE: 67

Asp Gly Gly Phe Ala Trp Gly Glu Ile Gly Ser Thr Gly Asn Pro Ser
1               5                   10                  15

<210> SEQ ID NO 68
<211> LENGTH: 17
<212> TYPE: PRT
<213> ORGANISM: Melanocarpus albomyces

<400> SEQUENCE: 68

Asp Gly Gly Phe Pro Ala Val Gln Ile Pro Ser Ser Thr Gly Asn Pro
1               5                   10                  15

Ser

<210> SEQ ID NO 69
<211> LENGTH: 5
<212> TYPE: PRT
<213> ORGANISM: Trichoderma reesei

<400> SEQUENCE: 69

Thr Gln Ser His Tyr
1               5

<210> SEQ ID NO 70
<211> LENGTH: 8
<212> TYPE: PRT
<213> ORGANISM: Trichoderma reesei

<400> SEQUENCE: 70

Asn Pro Tyr Tyr Ser Gln Cys Leu
1               5

<210> SEQ ID NO 71
<211> LENGTH: 8
<212> TYPE: PRT
<213> ORGANISM: Trichoderma reesei

<400> SEQUENCE: 71

Asn Pro Ala Tyr Ser Gln Cys Leu
1               5

<210> SEQ ID NO 72
<211> LENGTH: 8
<212> TYPE: PRT
<213> ORGANISM: Trichoderma reesei

<400> SEQUENCE: 72

Asn Pro Tyr Ala Ser Gln Cys Leu
1               5

<210> SEQ ID NO 73
<211> LENGTH: 8
<212> TYPE: PRT
```

<213> ORGANISM: Trichoderma reesei

<400> SEQUENCE: 73

Asn Pro Trp Tyr Ser Gln Cys Leu
1               5

<210> SEQ ID NO 74
<211> LENGTH: 8
<212> TYPE: PRT
<213> ORGANISM: Trichoderma reesei

<400> SEQUENCE: 74

Asn Pro Ala Ala Ser Gln Cys Leu
1               5

<210> SEQ ID NO 75
<211> LENGTH: 36
<212> TYPE: PRT
<213> ORGANISM: Artificial Sequence
<220> FEATURE:
<223> OTHER INFORMATION: 20K-junction-linker region generated by
      ligated plasmids

<400> SEQUENCE: 75

Asp Gly Gly Phe Pro Ala Val Gln Ile Pro Ser Ser Thr Gly Asn Pro
1               5                   10                  15

Ser Thr Thr Thr Thr Arg Arg Pro Ala Thr Thr Thr Gly Ser Ser Pro
            20                  25                  30

Gly Pro Thr Gln
        35

<210> SEQ ID NO 76
<211> LENGTH: 7
<212> TYPE: PRT
<213> ORGANISM: Trichoderma reesei

<400> SEQUENCE: 76

Pro Tyr Tyr Ser Gln Cys Leu
1               5

<210> SEQ ID NO 77
<211> LENGTH: 20
<212> TYPE: PRT
<213> ORGANISM: Artificial Sequence
<220> FEATURE:
<223> OTHER INFORMATION: 20K-junction-linker region generated by
      ligated plasmids

<400> SEQUENCE: 77

Asp Gly Gly Phe Pro Ala Val Gln Ile Pro Ser Ser Thr Gly Asn Pro
1               5                   10                  15

Ser Pro Thr Gln
        20

<210> SEQ ID NO 78
<211> LENGTH: 7
<212> TYPE: PRT
<213> ORGANISM: Trichoderma reesei

<400> SEQUENCE: 78

Pro Ala Ala Ser Gln Cys Leu
1               5

<210> SEQ ID NO 79
<211> LENGTH: 46

```
<212> TYPE: PRT
<213> ORGANISM: Artificial Sequence
<220> FEATURE:
<223> OTHER INFORMATION: 20K-junction-linker-CBD region generated by
      ligated plasmids

<400> SEQUENCE: 79

Phe Gly Pro Ile Gly Ser Thr Gly Asn Pro Ser Gly Gly Asn Pro Pro
1               5                   10                  15

Gly Gly Asn Pro Pro Gly Thr Thr Thr Thr Arg Arg Pro Ala Thr Thr
            20                  25                  30

Thr Gly Ser Ser Pro Gly Pro Thr Gln Ser His Tyr Gly Gln
        35                  40                  45

<210> SEQ ID NO 80
<211> LENGTH: 14
<212> TYPE: PRT
<213> ORGANISM: Artificial Sequence
<220> FEATURE:
<223> OTHER INFORMATION: 50K-linker region generated by ligated
      plasmids

<400> SEQUENCE: 80

Asn Leu Arg Trp Gly Glu Ile Gly Ser Thr Gly Asn Pro Ser
1               5                   10

<210> SEQ ID NO 81
<211> LENGTH: 5
<212> TYPE: PRT
<213> ORGANISM: Trichoderma reesei

<400> SEQUENCE: 81

Thr Gln Ser His Tyr
1               5

<210> SEQ ID NO 82
<211> LENGTH: 8
<212> TYPE: PRT
<213> ORGANISM: Trichoderma reesei

<400> SEQUENCE: 82

Asn Pro Tyr Tyr Ser Gln Cys Leu
1               5

<210> SEQ ID NO 83
<211> LENGTH: 14
<212> TYPE: PRT
<213> ORGANISM: Artificial Sequence
<220> FEATURE:
<223> OTHER INFORMATION: 50K-linker region generated by ligated
      plasmids

<400> SEQUENCE: 83

Asn Ile Arg Phe Gly Pro Ile Gly Ser Thr Gly Asn Pro Ser
1               5                   10

<210> SEQ ID NO 84
<211> LENGTH: 14
<212> TYPE: PRT
<213> ORGANISM: Artificial Sequence
<220> FEATURE:
<223> OTHER INFORMATION: CBHI-junction-linker region generated by
      ligated plasmids

<400> SEQUENCE: 84

Asn Ile Lys Val Gly Pro Ile Gly Ser Thr Gly Asn Pro Ser
1               5                   10
```

```
<210> SEQ ID NO 85
<211> LENGTH: 6
<212> TYPE: PRT
<213> ORGANISM: Artificial Sequence
<220> FEATURE:
<223> OTHER INFORMATION: Junction Region generated by ligated plasmids
<220> FEATURE:
<221> NAME/KEY: misc_feature
<222> LOCATION: (1)..(1)
<223> OTHER INFORMATION: Xaa is Gly or Val
<220> FEATURE:
<221> NAME/KEY: misc_feature
<222> LOCATION: (2)..(2)
<223> OTHER INFORMATION: Xaa is Pro, Gln or Glu
<220> FEATURE:
<221> NAME/KEY: misc_feature
<222> LOCATION: (4)..(4)
<223> OTHER INFORMATION: Xaa is Gly or Pro
<220> FEATURE:
<221> NAME/KEY: misc_feature
<222> LOCATION: (6)..(6)
<223> OTHER INFORMATION: Xaa is Ser or no amino acid

<400> SEQUENCE: 85

Xaa Xaa Ile Xaa Ser Xaa
1               5
```